United States Patent
Miyagi et al.

(10) Patent No.: US 11,718,704 B2
(45) Date of Patent: *Aug. 8, 2023

(54) CATALYST FOR DISSOCIATION OF BLOCKING AGENT FOR BLOCKED ISOCYANATES, AND THERMOSETTING COMPOSITION CONTAINING SAID CATALYST FOR DISSOCIATION OF BLOCKING AGENT

(71) Applicant: KOEI CHEMICAL COMPANY, LIMITED, Chiba (JP)

(72) Inventors: Motoyoshi Miyagi, Chiba (JP); Hitomi Tsuboi, Chiba (JP); Shingo Nitta, Chiba (JP)

(73) Assignee: KOEI CHEMICAL COMPANY, LIMITED, Chiba (JP)

( * ) Notice: Subject to any disclaimer, the term of this patent is extended or adjusted under 35 U.S.C. 154(b) by 639 days.

This patent is subject to a terminal disclaimer.

(21) Appl. No.: 16/647,593

(22) PCT Filed: Sep. 28, 2018

(86) PCT No.: PCT/JP2018/036224
§ 371 (c)(1),
(2) Date: Mar. 16, 2020

(87) PCT Pub. No.: WO2019/065953
PCT Pub. Date: Apr. 4, 2019

(65) Prior Publication Data
US 2020/0216600 A1   Jul. 9, 2020

(30) Foreign Application Priority Data

Sep. 29, 2017   (JP) .................. 2017-190846

(51) Int. Cl.
| | | |
|---|---|---|
| *C08G 18/20* | (2006.01) | |
| *C08G 18/80* | (2006.01) | |
| *C08G 18/18* | (2006.01) | |
| *C07D 233/90* | (2006.01) | |
| *C08G 18/48* | (2006.01) | |
| *C08G 18/73* | (2006.01) | |
| *C08G 18/32* | (2006.01) | |
| *B01J 31/02* | (2006.01) | |

(52) U.S. Cl.
CPC ....... *C08G 18/2081* (2013.01); *C07D 233/90* (2013.01); *C08G 18/18* (2013.01); *C08G 18/1858* (2013.01); *C08G 18/2027* (2013.01); *C08G 18/3231* (2013.01); *C08G 18/4829* (2013.01); *C08G 18/73* (2013.01); *C08G 18/80* (2013.01); *C08G 18/807* (2013.01); *C08G 18/8074* (2013.01); *C08G 18/8077* (2013.01); *B01J 31/0235* (2013.01); *B01J 31/0245* (2013.01); *B01J 31/0247* (2013.01); *B01J 31/0249* (2013.01)

(58) Field of Classification Search
CPC ............... C08G 18/2081; C08G 18/2027; C08G 18/80; C08G 18/3231; C08G 18/4829; C08G 18/807; C08G 18/8074; C08G 18/73; C08G 18/18; C08G 18/8077; C08G 18/1858; B01J 31/0235; B01J 31/0245; B01J 31/0247; B01J 31/0249; C07D 233/90
See application file for complete search history.

(56) References Cited

U.S. PATENT DOCUMENTS 10,689,478 B2 *   6/2020   Miyagi .............. C08G 18/1858
2012/0288632 A1   11/2012   Neu et al.

FOREIGN PATENT DOCUMENTS

| CN | 101012300 | 8/2007 |
|---|---|---|
| CN | 102712734 | 10/2012 |
| CN | 103420915 | 12/2013 |
| EP | 3 495 353 | 6/2019 |

(Continued)

OTHER PUBLICATIONS

International Search Report dated Nov. 13, 2018 in International (PCT) Application No. PCT/JP2018/036224.

(Continued)

*Primary Examiner* — Rabon A Sergent
(74) *Attorney, Agent, or Firm* — Wenderoth, Lind & Ponack, L.L.P.

(57) ABSTRACT

A blocking agent dissociation catalyst for blocked isocyanates comprising a nitrogen-containing compound represented by Formula (1a):

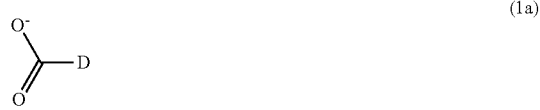

wherein D is represented by Formula (2):

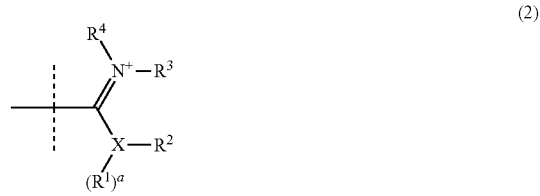

wherein $R^1$, $R^2$, $R^3$, $R^4$, and a are as described in the specification.

5 Claims, 10 Drawing Sheets

(56) References Cited

FOREIGN PATENT DOCUMENTS

| EP | 3 604 287 | 2/2020 | | |
|----|-----------|--------|---|---|
| JP | 2006-255928 | 9/2006 | | |
| JP | 2009-269306 | 11/2009 | | |
| JP | 2016-102182 | 6/2016 | | |
| JP | 2017-155203 | 9/2017 | | |
| WO | 2009/021095 | 2/2009 | | |
| WO | WO-2018025970 A1 * | 2/2018 | ........... | C07D 233/90 |
| WO | WO-2018181753 A1 * | 10/2018 | ........... | C07D 233/90 |

OTHER PUBLICATIONS

"Case Studies of Polyurethane Material Selection, Structure Control and Modification", Technical Information Institute Co., Ltd., 2014, pp. 40-41, with partial English translation.
"Latest Application Technology of Liquid Polyurethane", Chunichisha Co., Ltd., 1989, pp. 262-265, with partial English translation.
Gao et al., Handbook of Adhesion and Bonding Techniques, 1990, p. 404, with English language translation.
Xie et al., "Catalytic Synthesis of 2-Methylthiobenzothiazole with Dimethyl Carbonate as Methylating Reagent", Chemical Reagent, 32(9), pp. 779-782, cited in CC.
Office Action dated Aug. 30, 2021 in corresponding Chinese Patent Application No. 201880059626.6, with English-language translation.
Extended European Search Report dated May 12, 2021 in corresponding European Patent Application No. 18862008.2.

* cited by examiner

CATALYST FOR DISSOCIATION OF BLOCKING AGENT FOR BLOCKED ISOCYANATES, AND THERMOSETTING COMPOSITION CONTAINING SAID CATALYST FOR DISSOCIATION OF BLOCKING AGENT

TECHNICAL FIELD

The present invention relates to a blocking agent dissociation catalyst for blocked isocyanates and a thermosetting composition comprising the blocking agent dissociation catalyst.

BACKGROUND ART

Blocked isocyanates are compounds obtained by reaction of polyisocyanates with a blocking agent containing active hydrogen groups that are capable of reacting with the isocyanate groups. Blocked isocyanates have properties of being inactive at ordinary temperatures since the isocyanate groups of polyisocyanate are blocked by the blocking agent; when heated, the blocking agent dissociates to regenerate the isocyanate groups. Blocked isocyanates having such properties have been widely used for applications such as paints and adhesives, and as a raw material or a cross-linking agent for the production of one-component polyurethane.

Compounds known to be used as polyisocyanate blocking agents include phenols, alcohols, lactams, oximes, pyrazoles, and active methylenes. However, blocked isocyanates obtained by using these blocking agents require heating to dissociate the blocking agents as described above (Non-Patent Literature (NPL) 1). In order to reduce the heat energy required for the heating, attempts have been made to lower the dissociation temperature of the blocking agent of blocked isocyanate. As an attempt to lower the dissociation temperature of blocking agents of blocked isocyanates, it is known to use various metal organic acid salts, tertiary amines, or the like as a blocking agent dissociation catalyst (NPL 2).

As a metal organic acid salt, an organotin catalyst, such as dibutyltin dilaurate, is often used (NPL 2). However, organotin catalysts are highly toxic and pose a problem in terms of toxicity in environment and human body. There has already been a movement mainly in Europe to regulate the use of organotin catalysts in the production of polyurethane resin, and there has been a demand for a catalyst that can replace the organotin catalysts.

In contrast, the catalytic effect of tertiary amines is known to be proportional to its basicity. For example, a method that uses a cyclic guanidine compound, which is a strong base, as a blocking agent dissociation catalyst has been proposed (Patent Literature (PTL) 1). However, when the present inventors used a cyclic guanidine compound as a blocking agent dissociation catalyst for blocked isocyanates, the results were unsatisfactory since a thermosetting composition comprising the cyclic guanidine compound had poor storage stability although the cyclic guanidine compound exhibited excellent low-temperature dissociation (see the Examples described later).

CITATION LIST

Non-Patent Literature

NPL 1: "Case Studies of Polyurethane Material Selection, Structure Control and Modification" published by Technical Information Institute Co., Ltd., 2014, pp. 40-41

NPL 2: "Latest Application Technology of Liquid Polyurethane" published by Chunichisha Co., Ltd., 1989, pp. 262-265

Patent Literature

PTL 1: WO 2009/021095

SUMMARY OF INVENTION

Technical Problem

The present invention has been accomplished in view of the background art described above. An object of the present invention is to provide a blocking agent dissociation catalyst for blocked isocyanates that achieves excellent low-temperature dissociation of a blocking agent of blocked isocyanate. Another object is to provide a thermosetting composition comprising the blocking agent dissociation catalyst and exhibiting excellent storage stability.

Solution to Problem

The present inventors conducted extensive research to solve the above problems and found that a nitrogen-containing compound represented by Formula (1a) or Formula (1b) used as a blocking agent dissociation catalyst for blocked isocyanates achieved excellent low-temperature dissociation, and that a thermosetting composition comprising the blocking agent dissociation catalyst exhibited excellent storage stability. The present invention has thus been completed.

More specifically, the present invention relates to the following [1] to [12].

[1] A blocking agent dissociation catalyst for blocked isocyanates comprising a nitrogen-containing compound represented by Formula (1a):

Formula (1a)

wherein D is a nitrogen-containing organic group represented by Formula (2):

wherein $R^1$, $R^2$, $R^3$, and $R^4$ are the same or different, and each represents a hydrocarbon group that may contain a heteroatom; some or all of $R^1$, $R^2$, $R^3$, and $R^4$ may be bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom.

[2] A blocking agent dissociation catalyst for blocked isocyanates comprising a nitrogen-containing compound represented by Formula (1b):

Formula (1b)

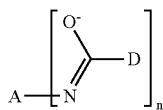

(1b)

wherein A represents a substituted or unsubstituted hydrocarbon group, n is an integer of 1 or more, and D is a nitrogen-containing organic group represented by Formula (2):

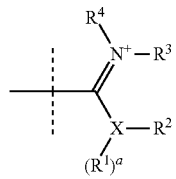

(2)

wherein $R^1$, $R^2$, $R^3$, and $R^4$ are the same or different, and each represents a hydrocarbon group that may contain a heteroatom; some or all of $R^1$, $R^2$, $R^3$, and $R^4$ may be bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom.

[3] The blocking agent dissociation catalyst according to [2], wherein A is an unsubstituted hydrocarbon group, or a hydrocarbon group having at least one substituent selected from a halogen atom, an alkylamino group, a dialkylamino group, an alkoxy group, an aryloxy group, a nitro group, a cyano group, a sulfonyl group, or an isocyanate group.

[4] The blocking agent dissociation catalyst for blocked isocyanates according to [2] or [3], wherein n is an integer of 1 to 6.

[5] The blocking agent dissociation catalyst for blocked isocyanates according to [2], wherein the nitrogen-containing compound represented by Formula (1b) is a nitrogen-containing compound represented by the following Formula (1b-1), (1b-2), or (1b-3):

Formula (1b-1)

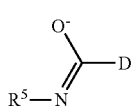

(1b-1)

wherein $R^5$ represents a substituted or unsubstituted hydrocarbon group, and D is as defined above;

Formula (1b-2)

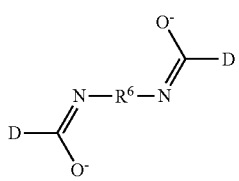

(1b-2)

wherein $R^6$ represents a substituted or unsubstituted hydrocarbon group, and D is as defined above; or Formula (1b-3)

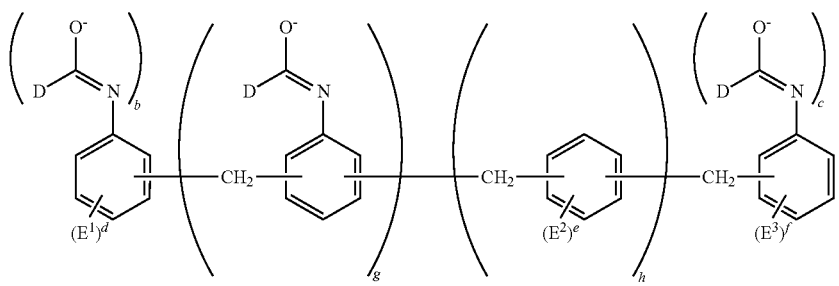

(1b-3)

wherein $E^1$, $E^2$, and $E^3$ each independently represent a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; g and h each independently represent an integer of 0 to 4, b and c are 0 or 1, and d, e, and f each independently represent an integer of 0 to 4, provided that at least one of b and c is 1 when g is 0; and D is as defined above.

[6] The blocking agent dissociation catalyst for blocked isocyanates according to any one of [1] to [5], wherein the nitrogen-containing organic group represented by Formula (2) is a nitrogen-containing organic group represented by the following Formula (2-1), (2-2), or (2-3):

Formula (2-1)

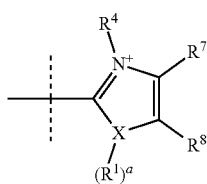

(2-1)

wherein $R^1$, $R^4$, X, and a are as defined above; and $R^7$ and $R^8$ are the same or different, and each represents a hydrogen atom or a $C_1$-$C_6$ hydrocarbon group that may contain a heteroatom;

Formula (2-2)

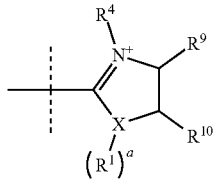

(2-2)

wherein $R^1$, $R^4$, X, and a are as defined as above; and $R^9$ and $R^{10}$ are the same or different, and each represents a hydrogen atom or a $C_1$-$C_6$ hydrocarbon group that may contain a heteroatom; or Formula (2-3)

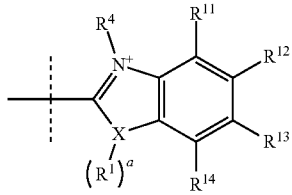

(2-3)

wherein $R^1$, $R^4$, X, and a are as defined above; and $R^{11}$, $R^{12}$, $R^{13}$, and $R^{14}$ are the same or different, and each represents a hydrogen atom or a $C_1$-$C_6$ hydrocarbon group that may contain a heteroatom.

[7] The blocking agent dissociation catalyst for blocked isocyanates according to any one of [1] to [6], wherein X is a nitrogen atom.

[8] A thermosetting composition comprising the blocking agent dissociation catalyst for blocked isocyanates according to any one of [1] to [7], a blocked isocyanate, and a compound having an isocyanate-reactive group.

[9] The thermosetting composition according to [8], wherein the blocked isocyanate is a blocked isocyanate sealed with at least one blocking agent selected from the group consisting of alcohols, phenols, amines, lactams, oximes, ketoenols, and pyrazoles.

[10] The thermosetting composition according to [8], wherein the blocked isocyanate is a blocked isocyanate sealed with at least one blocking agent selected from the group consisting of lactams, oximes, and pyrazoles.

[11] A method for dissociating a blocking agent, comprising heating a blocked isocyanate in the presence of the blocking agent dissociation catalyst for blocked isocyanates according to any one of [1] to [7].

[12] A modified isocyanate represented by the following Formula (1b-3):

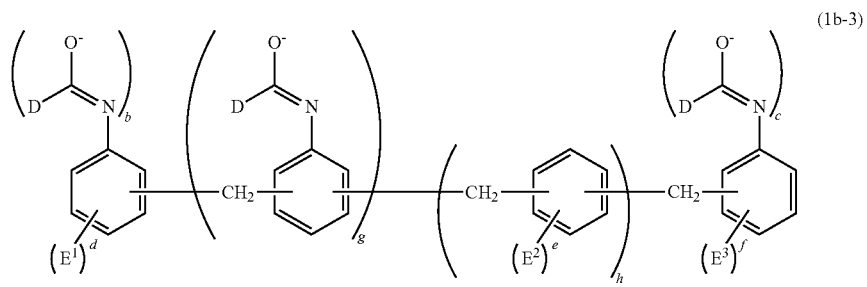

(1b-3)

wherein $E^1$, $E^2$, and $E^3$ each independently represent a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; g and h each independently represent an integer of 0 to 4, b and c are 0 or 1, d and f each independently represent an integer of 0 to 4, and e is an integer of 1 to 4, provided that at least one of b and c is 1 when g is 0, and at least one of d and f is 1 when h is 0; and D is as defined above.

The present invention also includes the following embodiments.

A nitrogen-containing compound represented by Formula (1a), (1b), (1b-1), (1b-2), or (1b-3) for use as a blocking agent dissociation catalyst for blocked isocyanates.

A nitrogen-containing compound represented by Formula (1a), (1b), (1b-1), (1b-2), or (1b-3) for producing a blocking agent dissociation catalyst for blocked isocyanates.

Advantageous Effects of Invention

The present invention can provide a blocking agent dissociation catalyst for blocked isocyanates that achieves excellent low-temperature dissociation of a blocking agent of blocked isocyanate. The present invention also provides a thermosetting composition comprising the blocking agent dissociation catalyst and exhibiting excellent storage stability.

DESCRIPTION OF EMBODIMENTS

Figure 1:
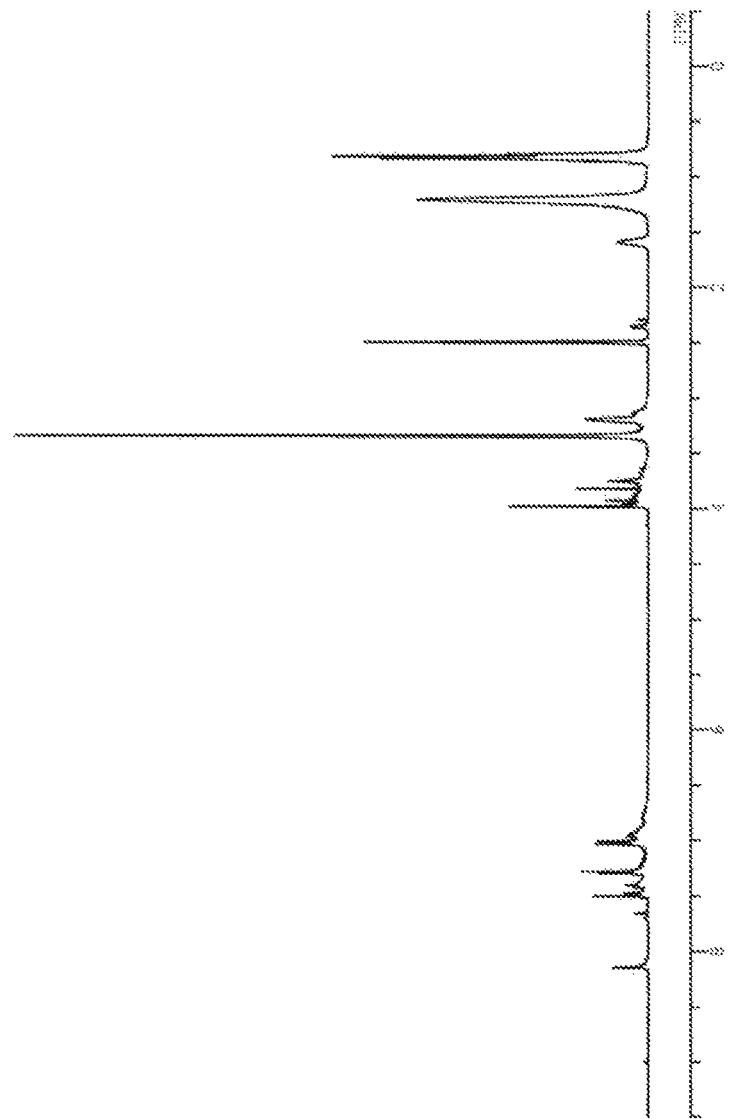
FIG. 1 is a graph showing the $^1$H-NMR analysis results of the blocking agent dissociation catalyst (C16) of the Examples of the present application.

Embodiments of the present invention are described in detail below.

The blocking agent dissociation catalyst for blocked isocyanates of the present invention (hereinafter also referred to as the blocking agent dissociation catalyst (A)) comprises a nitrogen-containing compound represented by Formula (1a) (hereinafter also referred to as the nitrogen-containing compound (1a)) or a nitrogen-containing compound represented by Formula (1b) (hereinafter also referred to as the nitrogen-containing compound (1b)) as an active ingredient. Hereinafter, the nitrogen-containing compound represented by Formula (1a) and the nitrogen-containing compound represented by Formula (1b) are also collectively referred to as the nitrogen-containing compound (1).

In Formula (1a), D is a nitrogen-containing organic group represented by Formula (2).

In Formula (1b), A is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group.

When A is a substituted hydrocarbon group, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group A may be substituted with a heteroatom, such as oxygen, nitrogen, or sulfur. When the hydrocarbon group A is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, n-propyl, isopropyl, n-butyl, isobutyl, sec-butyl, tert-butyl, and n-pentyl. The number of carbon atoms in the alkyl group is preferably 1 to 3, and more preferably 1 or 2.

Examples of the aryl moiety of the above aryloxy groups include $C_6$-$C_{10}$ aryl groups. Specific examples include a phenyl group, a naphthyl group, and the like.

The number of substituents is 1 to 5, preferably 1 to 3, and more preferably 1 or 2.

In Formula (1b), n is an integer of 1 or more, preferably 1 to 6, more preferably 1 to 4, and particularly preferably 1 or 2.

In Formula (1b), D is a nitrogen-containing organic group represented by Formula (2).

In the present invention, the nitrogen-containing compound represented by Formula (1b) is preferably a nitrogen-containing compound represented by Formula (1b-1), (1b-2), or (1b-3); and particularly preferably a nitrogen-containing compound represented by Formula (1b-1).

In Formula (1b-1), $R^5$ is a substituted or unsubstituted hydrocarbon group, preferably a substituted or unsubstituted $C_1$-$C_{50}$ hydrocarbon group, more preferably a substituted or unsubstituted $C_1$-$C_{30}$ hydrocarbon group, even more preferably a substituted or unsubstituted $C_1$-$C_{14}$ hydrocarbon group, and particularly preferably a substituted or unsubstituted $C_1$-$C_{12}$ hydrocarbon group. Specific examples include a methyl group, an ethyl group, an n-propyl group, an isopropyl group, an n-butyl group, a sec-butyl group, a tert-butyl group, an n-pentyl group, an n-hexyl group, an n-heptyl group, an n-decyl group, an n-dodecyl group, an n-octadecyl group, a cyclopropyl group, a cyclopentyl group, a cyclohexyl group, a phenyl group, a naphthyl group, a benzyl group, a phenethyl group, a tolyl group, an allyl group, and the like; and preferably a benzyl group and a phenyl group.

When $R^5$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group $R^5$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, n-propyl, isopropyl, n-butyl, isobutyl, sec-butyl, tert-butyl, and n-pentyl. The number of carbon atoms in the alkyl group is preferably 1 to 3, and more preferably 1 or 2.

Examples of the aryl moiety of the above aryloxy groups include $C_5$-$C_{10}$ aryl groups. Specific examples include a phenyl group, a naphthyl group, and the like.

The number of substituents is 1 to 5, preferably 1 to 3, and more preferably 1 or 2.

In Formula (1b-1), D is as defined above.

In Formula (1b-2), $R^6$ is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group. Specific examples include alkylene groups, such as a methylene group, a dimethylmethylene group, an ethylene group, an n-propylene group, an n-butylene group, an n-pentylene group, an n-hexylene group, an n-heptylene group, an n-octylene group, an n-nonylene group, an n-decylene group, an n-dodecylene group, an n-octadecylene group, and a cyclohexylene group; arylene groups, such as a phenylene group, a 2-methylphenylene group, a 2,6-dimethylphenylene group, a 2,4-dimethylphenylene group, a 2,3-dimethylphenylene group, and a naphthylene group; arylalkylene groups, such as a phenylmethylene group, a phenylethylene group, a 1-phenylpropylene group, a 2-phenylpropylene group, a 1-phenylbutylene group, a 2-phenylbutylene group, a naphthylmethylene group, and a naphthylethylene group; arylenealkylene groups obtained by suitably combining the above alkylene groups and arylene groups; and the like. These divalent hydrocarbon groups may be repeated or combined to constitute one divalent hydrocarbon group.

When $R^6$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group $R^6$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, n-propyl, isopropyl, n-butyl, isobutyl, sec-butyl, tert-butyl, and n-pentyl. The number of carbon atoms in the alkyl group is preferably 1 to 3, and more preferably 1 or 2.

Examples of the aryl moiety of the above aryloxy groups include $C_6$-$C_{10}$ aryl groups. Specific examples include a phenyl group, a naphthyl group, and the like.

The number of substituents is 1 to 5, preferably 1 to 3, and more preferably 1 or 2.

In Formula (1b-2), D is as defined above.

In Formula (1b-3), $E^1$, $E^2$, and $E^3$ each independently represent a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; preferably a substituted or unsubstituted hydrocarbon group, an (alkylamino)carbonylamino group, a (dialkylamino)carbonylamino group, or an isocyanate group; and more preferably an (alkylamino)carbonylamino group or a (dialkylamino)carbonylamino group.

g and h each independently represent an integer of 0 to 4. b and c are 0 or 1, and d, e, and f each independently represent an integer of 0 to 4. However, at least one of b and c is 1 when g is 0. D is as defined above.

In another embodiment of the present invention, d and f each independently represent an integer of 0 to 4, and e represents an integer of 1 to 4. However, at least one of b and c is 1 when g is 0, and at least one of d and f is 1 when h is 0.

The nitrogen-containing organic group represented by Formula (2) is explained.

In Formula (2), $R^1$, R, $R^3$, and $R^4$ are hydrocarbon groups that may contain a heteroatom. Some or all of $R^1$, $R^2$, $R^3$, and $R^4$ may be bonded together to form a ring structure. For example, $R^1$ and $R^2$, $R^2$ and $R^3$, $R^3$ and $R^4$, $R^2$, $R^3$, and $R^4$, or $R^1$, $R^2$, $R^3$, and $R^4$, may be bonded together to form a ring structure. Examples of the hydrocarbon group that may contain a heteroatom include a methyl group, an ethyl group, an n-propyl group, an isopropyl group, an n-butyl group, an s-butyl group, a t-butyl group, an n-pentyl group, an n-hexyl group, an n-octyl group, an n-decyl group, an n-dodecyl group, an allyl group, a benzyl group, a cyclohexyl group, an adamantyl group, a phenyl group, a 2,6-diisopropylphenyl group, a 2,4,6-trimethylphenyl group, a 2-methoxyethyl group, a 2-ethoxyethyl group, 2-(dimethylamino)ethyl group, and the like; preferably a methyl group, an ethyl group, an n-propyl group, an isopropyl group, a t-butyl group, an n-octyl group, a cyclopentyl group, a cyclohexyl group, a phenyl group, and a 2,4,6-trimethylphenyl group; more preferably a methyl group, an ethyl group, an isopropyl group, a t-butyl group, an n-octyl group, and a phenyl group; and particularly preferably a methyl group, an isopropyl group, a t-butyl group, an n-octyl group, and a phenyl group. X is a nitrogen atom, an oxygen atom, or a sulfur atom; and preferably a nitrogen atom.

In Formula (2), a is 0 or 1. a is 1 when X is a nitrogen atom, and a is 0 when X is an oxygen atom or a sulfur atom. That is, Formula (2) represents a nitrogen-containing organic group represented by the following Formula (2a), (2b), or (2c). In other words, when X represents an oxygen atom or a sulfur atom, a is 0 and $R^1$ does not exist.

(2a)

-continued

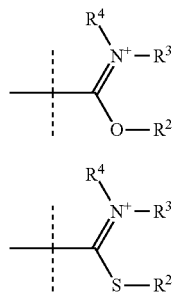

(2b)

(2c)

wherein $R^1$, $R^2$, $R^3$, and $R^4$ are as defined above.

In the present invention, $R^2$ and $R^3$ of the nitrogen-containing organic group represented by Formula (2) are preferably bonded together to form a ring structure. The nitrogen-containing organic group represented by Formula (2) wherein a ring is formed is preferably a nitrogen-containing organic group represented by Formula (2-1), (2-2), or (2-3); and particularly preferably a nitrogen-containing organic group represented by Formula (2-1).

In Formula (2-1), $R^1$, $R^4$, X, and a are as defined above. $R^7$ and $R^8$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, an n-propyl group, an isopropyl group, an n-butyl group, an s-butyl group, a t-butyl group, a pentyl group, a hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylimidazolium group, a 1-ethyl-3-methylimidazolium group, a 1-methyl-3-propylimidazolium group, a 1-methyl-3-isopropylimidazolium group, a 1-butyl-3-methylimidazolium group, a 1-tert-butyl-3-methylimidazolium group, a 1-hexyl-3-methylimidazolium group, a 1-methyl-3-octylimidazolium group, a 1-methyl-3-(2-ethylhexyl)imidazolium group, a 1-dodecyl-3-methylimidazolium group, a 1-allyl-3-methylimidazolium group, a 1-benzyl-3-methylimidazolium group, a 1-methyl-3-phenylimidazolium group, a 1-methyl-3-(2,6-diisopropylphenyl)imidazolium group, a 1-mesityl-3-methylimidazolium group, a 1,3-diethylimidazolium group, a 1,3-dipropylimidazolium group, a 1,3-diisopropylimidazolium group, a 1,3-dibutylimidazolium group, a 1,3-di-tert-butylimidazolium group, a 1,3-dioctylimidazolium group, a 1,3-diphenylimidazolium group, a 1,3-bis(2,6-diisopropylphenyl)imidazolium group, a 1,3-dimesitylimidazolium group, a 1,3,4,5-tetramethylimidazolium group, a 3-methyloxazolium group, a 3-ethyloxazolium group, a 3-propyloxazolium group, a 3-isopropyloxazolium group, a 3-butyloxazolium group, a 3-tert-butyloxazolium group, a 3-octyloxazolium group, a 3-(2-ethylhexyl)oxazolium group, a 3-dodecyloxazolium group, a 3-phenyloxazolium group, a 3-(2,6-diisopropylphenyl)oxazolium group, a 3-mesityloxazolium group, a 3,5-dimethyloxazolium group, a 3,4,5-trimethyloxazolium group, a 3-methylthiazolium group, a 3-ethylthiazolium group, a 3-propylthiazolium group, a 3-isopropylthiazolium group, a 3-butylthiazolium group, a 3-tert-butylthiazolium group, a 3-octylthiazolium group, a 3-(2-ethylhexyl)thiazolium group, a 3-dodecylthiazolium group, a 3-phenylthiazolium group, a 3-(2,6-diisopropylphenyl)thiazolium group, a 3-mesitylthiazolium group, a 3,4-dimethylthiazolium group, a 3,5-dimethylthiazolium group, a 3,4,5-trimethylthiazolium group, and the like; preferably a 1,3-dimethylimidazolium group, a 1-ethyl-3-methylimidazolium group, a 1-methyl-3-propylimidazolium group, a 1-butyl-3-methylimidazolium group, and a 1-methyl-3-octylimidazolium group; and particularly preferably a 1,3-dimethylimidazolium group, a 1-butyl-3-methylimidazolium group, and a 1-methyl-3-octylimidazolium group.

In the present specification, the terms propyl, butyl, pentyl, hexyl, heptyl, octyl, nonyl, dodecyl, etc., refer to linear alkyl groups, such as n-propyl, n-butyl, n-pentyl, n-hexyl, n-heptyl, n-octyl, n-nonyl, and n-dodecyl, respectively, unless otherwise specified.

In Formula (2-2), $R^1$, $R^4$, X, and a are as defined above. $R^9$ and $R^{10}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, an n-propyl group, an isopropyl group, an n-butyl group, an s-butyl group, a t-butyl group, an n-pentyl group, an n-hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylimidazolinium group, a 1-ethyl-3-methylimidazolinium group, a 1-methyl-3-propylimidazolinium group, a 1-butyl-3-methylimidazolinium group, a 1-hexyl-3-methylimidazolinium group, a 1-methyl-3-octylimidazolinium group, a 1-dodecyl-3-methylimidazolinium group, a 1-allyl-3-methylimidazolinium group, a 1-benzyl-3-methylimidazolinium group, a 1-methyl-3-phenylimidazolinium group, a 1-methyl-3-(2,6-diisopropylphenyl)imidazolinium group, a 1-mesityl-3-methylimidazolinium group, a 1,3-diethylimidazolinium group, a 1,3-dipropylimidazolinium group, a 1,3-diisopropylimidazolinium group, a 1,3-dibutylimidazolinium group, a 1,3-di-tert-butylimidazolinium group, a 1,3-dioctylimidazolinium group, a 1,3-diphenylimidazolinium group, a 1,3-bis(2,6-diisopropylphenyl)imidazolinium group, a 1,3-dimesitylimidazolinium group, a 1,3,4,5-tetramethylimidazolinium group, a 3-methyloxazolinium group, a 3-ethyloxazolinium group, a 3-propyloxazolinium group, a 3-isopropyloxazolinium group, a 3-butyloxazolinium group, a 3-tert-butyloxazolinium group, a 3-octyloxazolinium group, a 3-dodecyloxazolinium group, a 3-phenyloxazolinium group, a 3-(2,6-diisopropylphenyl)oxazolinium group, a 3-mesityloxazolinium group, a 3,4-dimethyloxazolinium group, a 3,5-dimethyloxazolinium group, a 3,4,5-trimethyloxazolinium group, a 3-methylthiazolinium group, a 3-ethylthiazolinium group, a 3-propyithiazolinium group, a 3-isopropylthiazolinium group, a 3-butylthiazolinium group, a 3-tert-butylthiazolinium group, a 3-octylthiazolinium group, a 3-dodecylthiazolinium group, a 3-phenylthiazolinium group, a 3-(2,6-diisopropylphenyl)thiazolinium group, a 3-mesitylthiazolinium group, a 3,4-dimethylthiazolinium group, a 3,5-dimethylthiazolinium group, a 3,4,5-trimethylthiazolinium group, and the like; preferably a 1,3-dimethylimidazolinium group, a 1-ethyl-3-methylimidazolinium group, a 1-methyl-3-propylimidazolinium group, a 1-butyl-3-methylimidazolinium group, and a 1-methyl-3-octylimidazolinium group; and particularly preferably a 1,3-dimethylimidazolinium group, a 1-butyl-3-methylimidazolinium group, and a 1-methyl-3-octylimidazolinium group.

In Formula (2-3), $R^1$, $R^4$, X, and a are as defined above. $R^{11}$, $R^{12}$, $R^{13}$, and $R^{14}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, an n-propyl group, an isopropyl group, an n-butyl group, an s-butyl group, a t-butyl group, an n-pentyl group, an n-hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylbenzimidazolium group, a 1-ethyl-3-methylbenzimidazolium group, a 1-methyl-3-propylbenzimidazolium group, a 1-methyl-3-isopropylbenzimidazolium group, a 1-butyl-3-methylbenzimidazolium group, a 1-tert-butyl-3-methylbenzimidazolium group, a 1-hexyl-3-methylbenzimidazolium group, a 1-methyl-3-octylbenzimidazolium group, a 1-dodecyl-3-methylbenzimidazolium group, a 1-allyl-3-methylbenzimidazolium group, a 1-benzyl-3-methylbenzimidazolium group, a 1,3-diethylbenzimidazolium group, a 1,3-dipropylbenzimidazolium group, a 1,3-diisopropylbenzimidazolium group, a 1,3-dibutylbenzimidazolium group, a 1,3-di-tert-butylbenzimidazolium group a 1,3-dioctylbenzimidazolium group, a 1,3-diphenylbenzimidazolium group, a 1,3-bis(2,6-diisopropylphenyl)benzimidazolium group, a 1,3-dimesitylbenzimidazolium group, a 1,3,6-trimethylbenzimidazolium group, a 1-acetyl-3,6-dimethylbenzimidazolium group, a 1,3,6,7-tetramethylbenzimidazolium group, a 1,3-dibenzyl-6,7-dimethylbenzimidazolium group, a 3-methylbenzoxazolium group, a 3-methylbenzothiazolium group, and the like; preferably a
- 1,3-dimethylbenzimidazolium group, a 1-ethyl-3-methylbenzimidazolium group, a 1-methyl-3-propylbenzimidazolium group, and a 1-butyl-3-methylbenzimidazolium group; and particularly preferably a 1,3-dimethylbenzimidazolium group.

Next, specific examples of the nitrogen-containing compound (1a) are shown below. However, the present invention is not limited thereto.

Specific examples of the nitrogen-containing compound (1a) include 1,3-dimethylimidazolium-2-carboxylate, 1-ethyl-3-methylimidazolium-2-carboxylate, 1-methyl-3-propylimidazolium-2-carboxylate, 1-methyl-3-isopropylimidazolium-2-carboxylate, 1-butyl-3-methylimidazolium-2-carboxylate, 1-tert-butyl-3-methylimidazolium-2-carboxylate, 1-hexyl-3-methylimidazolium-2-carboxylate, 1-methyl-3-octylimidazolium-2-carboxylate, 1-(2-ethylhexyl)-3-methylimidazolium-2-carboxylate, 1-dodecyl-3-methylimidazolium-2-carboxylate, 1-allyl-3-methylimidazolium-2-carboxylate, 1-methyl-3-phenylimidazolium-2-carboxylate, 1-methyl-3-(p-tolyl)imidazolium-2-carboxylate, 1-methyl-3-(2,6-diisopropylphenyl)imidazolium-2-carboxylate, 1-benzyl-3-methylimidazolium-2-carboxylate, 1-methyl-3-(2-phenylethyl) imidazolium-2-carboxylate, 1-mesityl-3-methylimidazolium-2-carboxylate, 1,3-diethylimidazolium-2-carboxylate, 1,3-dipropylimidazolium-2-carboxylate, 1,3-diisopropylimidazolium-2-carboxylate, 1,3-dibutylimidazolium-2-carboxylate, 1,3-di-tert-butylimidazolium-2-carboxylate, 1,3-dihexylimidazolium-2-carboxylate, 1,3-dicyclohexylimidazolium-2-carboxylate, 1,3-dioctylimidazolium-2-carboxylate, 1,3-bis(2-ethylhexyl)imidazolium-2-carboxylate, 1,3-diadamantylimidazolium-2-carboxylate, 1,3-didodecylimidazolium-2-carboxylate, 1,3-diphenylimidazolium-2-carboxylate, 1,3-bis(p-tolyl)imidazolium-2-carboxylate, 1,3-bis(m-tolyl)imidazolium-2-carboxylate, 1,3-bis(o-tolyl)imidazolium-2-carboxylate, 1,3-bis(2,6-dimethylphenyl)imidazolium-2-carboxylate, 1,3-bis(2,6-diisopropylphenyl)imidazolium-2-carboxylate, 1,3-dimesitylimidazolium-2-carboxylate, 1,3-dibenzylimidazolium-2-carboxylate, 1,3-bis(2-ethylphenyl) imidazolium-2-carboxylate, 1,3,4,5-tetramethylimidazolium-2-carboxylate, 1,3-diethyl-4,5-dimethylimidazolium-2-carboxylate, 4,5-dimethyl-1,3-diisopropylimidazolium-2-carboxylate, 1,3-dibutyl-4,5-dimethylimidazolium-2-carboxylate, 1,3-di-tert-butyl-4,5-dimethylimidazolium-2-carboxylate, 4,5-dimethyl-1,3-diphenylimidazolium-2-carboxylate, 4,5-dimethyl-1,3-bis(2,6-diisopropylphenyl) imidazolium-2-carboxylate, 1,3-dimesityl-4,5-dimethylimidazolium-2-carboxylate, 4,5-dichloro-1,3-dimethylimidazolium-2-carboxylate, 4,5-dicyano-1,3-dimethylimidazolium-2-carboxylate, 4,5-dimethoxy-1,3-dimethylimidazolium-2-carboxylate, 1,3-dimethyl-4,5-dinitroimidazolium-2-carboxylate, 3-methyloxazolium-2-carboxylate, 3-ethyloxazolium-2-carboxylate, 3-propyloxazolium-2-carboxylate, 3-isopropyloxazolium-2-carboxylate, 3-butyloxazolium-2-carboxylate, 3-tert-butyloxazolium-2-carboxylate, 3-octyloxazolium-2-carboxylate, 3-(2-ethylhexyl) oxazolium-2-carboxylate, 3-dodecyloxazolium-2-carboxylate, 3-allyloxazolium-2-carboxylate, 3-benzyloxazolium-2-carboxylate, 3-cyclohexyloxazolium-2-carboxylate, 3-phenyloxazolium-2-carboxylate, 3-(2,6-diisopropylphenyl) oxazolium-2-carboxylate, 3-mesityloxazolium-2-carboxylate, 3,4-dimethyloxazolium-2-carboxylate, 3,5-dimethyloxazolium-2-carboxylate, 3,4,5-trimethyloxazolium-2-carboxylate, 3-methylthiazolium-2-carboxylate, 3-ethylthiazolium-2-carboxylate, 3-propylthiazolium-2-carboxylate, 3-isopropylthiazolium-2-carboxylate, 3-butylthiazolium-2-carboxylate, 3-tert-butylthiazolium-2-carboxylate, 3-octylthiazolium-2-carboxylate, 3-(2-ethylhexyl) thiazolium-2-carboxylate, 3-dodecylthiazolium-2-carboxylate, 3-allylthiazolium-2-carboxylate, 3-benzylthiazolium-2-carboxylate, 3-cyclohexylthiazolium-2-carboxylate, 3-phenylthiazolium-2-carboxylate, 3-(2,6-diisopropylphenyl) thiazolium-2-carboxylate, 3-mesitylthiazolium-2-carboxylate, 3,4-dimethylthiazolium-2-carboxylate, 3,5-dimethylthiazolium-2-carboxylate, 3,4,5-trimethylthiazolium-2-carboxylate, 3-methyl-5-(2-hydroxyethyl)-4-methylthiazolium-2-carboxylate, 3-benzyl-5-(2-hydroxyethyl)-4-methylthiazolium-2-carboxylate, 1,3-dimethylimidazolinium-2-carboxylate, 1-ethyl-3-methylimidazolinium-2-carboxylate, 1-methyl-3-propylimidazolinium-2-carboxylate, 1-methyl-3-isopropylimidazolinium-2-carboxylate, 1-butyl-3-methylimidazolinium-2-carboxylate, 1-tert-butyl-3-methylimidazolinium-2-carboxylate, 1-methyl-3-octylimidazolinium-2-carboxylate, 1-methyl-3-(2-ethylhexyl) imidazolinium-2-carboxylate, 1-dodecyl-3-methylimidazolinium-2-carboxylate, 1-allyl-3-methylimidazolinium-2-carboxylate, 1-benzyl-3-methylimidazolinium-2-carboxylate, 1-(2-dimethylaminoethyl)-3-methylimidazolinium-2-carboxylate, 1,3-diisopropylimidazolinium-2-carboxylate, 1,3-dibutylimidazolinium-2-carboxylate, 1,3-di-tert-butylimidazolinium-2-carboxylate, 1,3-dioctylimidazolinium-2-carboxylate, 1,3-bis(2-ethylhexyl) imidazolinium-2-carboxylate, 1,3-dodecylimidazolinium-2-carboxylate, 1,3-diadamantylimidazolinium-2-carboxylate, 1,3-diphenylimidazolinium-2-carboxylate, 1,3-bis(2,6- diisopropylphenyl) imidazolinium-2-carboxylate, 1,3-dimesityl imidazolinium-2-carboxylate, 3-methyloxazolinium-2-carboxylate, 3-ethyloxazolinium-2-carboxylate, 3-propyloxazolinium-2-carboxylate, 3-isopropyloxazolinium-2-carboxylate, 3-butyloxazolinium-2-carboxylate, 3-octyloxazolinium-2-carboxylate, 3-(2-ethylhexyl) oxazolinium-2-carboxylate, 3-dodecyloxazolinium-2-carboxylate, 3-allyloxazolinium-2-carboxylate, 3-benzyloxazolinium-2-carboxylate, 3-phenyloxazolinium-2-carboxylate, 3-(2,6-diisopropylphenyl) oxazolinium-2-carboxylate, 3-mesityloxazolinium-2-carboxylate, 3,4-dimethyloxazolinium-2-carboxylate, 3,5-dimethyloxazolinium-2-carboxylate, 3,4,5-trimethyloxazolinium-2-carboxylate, 3-methylthiazolinium-2-carboxylate, 3-ethylthiazolinium-2-carboxylate, 3-propylthiazolinium-2-carboxylate, 3-isopropylthiazolinium-2-carboxylate, 3-butylthiazolinium-2-carboxylate, 3-tert-butylthiazolinium-2-carboxylate, 3-octylthiazolinium-2-carboxylate, 3-(2-ethyihexyl) thiazolinium-2-carboxylate, 3-dodecylthiazolinium-2-carboxylate, 3-allylthiazolinium-2-carboxylate, 3-benzylthiazolinium-2-carboxylate, 3-phenylthiazolinium-2-carboxylate, 3-(2,6-diisopropylphenyl) thiazolinium-2-carboxylate, 3-mesitylthiazolinium-2-carboxylate, 3,4-dimethylthiazolinium-2-carboxylate, 3,5-dimethylthiazolinium-2-carboxylate, 3,4,5-trimethyithiazolinium-2-carboxylate, 1,3-dimethylbenzimidazolium-2-carboxylate, 1-ethyl-3-methylbenzimidazolium-2-carboxylate, 1-methyl-3-propylbenzimidazolium-2-carboxylate, 1-butyl-3-methylbenzimidazolium-2-carboxylate, 1-tert-butyl-3-methylbenzimidazolium-2-carboxylate, 1-methyl-3-octylbenzimidazolium-2-carboxylate, 1-dodecyl-3-methylbenzimidazolium-2-carboxylate, 1-allyl-3-methylbenzimnidazolium-2-carboxylate, 1-benzyl-3-methylbenzimidazolium-2-carboxylate, 1,3-diethylbenzimidazolium-2-carboxylate, 1,3-dibutylbenzimidazolium-2-carboxylate, 1,3-di-tert-butylbenzimidazolium-2-carboxylate, 1,3-dioctylbenzimidazolium-2-carboxylate, 1,3-bis(2-ethylhexyl)benzimidazolium-2-carboxylate, 1,3-diphenylbenzimidazolium-2-carboxylate, 1,3-bis(2,6-diisopropylphenyl)benzimridazolium-2-carboxylate, 1,3-dimesitylbenzimidazolium-2-carboxylate, 1,3,6-trimethylbenzimidazolium-2-carboxylate 1,3,6,7-tetramethylbenzimidazolium-2-carboxylate, 1,3-dibenzyl-6,7-dimethylbenzimidazolium-2-carboxylate, 3-methylbenzoxazolium-2-carboxylate, 3-ethylbenzoxazolium-2-carboxylate, 3-propylbenzoxazolium-2-carboxylate, 3-isopropylbenzoxazolium-2-carboxylate, 3-butylbenzoxazolium-2-carboxylate, 3-tert-butylbenzoxazolium-2-carboxylate, 3-octylbenzoxazolium-2-carboxylate, 3-(2-ethylhexyl)benzoxazolium-2-carboxylate, 3-dodecylbenzoxazolium-2-carboxylate, 3-allylbenzoxazolium-2-carboxylate, 3-benzylbenzoxazolium-2-carboxylate, 3-phenxylbenzoxazolium-2-carboxylate, 3-(2,6-diisopropylphenyl)benzoxazolium-2-carboxylate, 3-mesitylbenzoxazolium-2-carboxylate, 5-hydroxy-3-methylbenzoxazolium-2-carboxylate, 6-amino-3-methylbenzoxazolium-2-carboxylate, 3-methylbenzothiazolium-2-carboxylate, 3-ethylbenzothiazolium-2-carboxylate, 3-propylbenzothiazolium-2-carboxylate, 3-isopropylbenzothiazolium-2-carboxylate, 3-butylbenzothiazolium-2-carboxylate, 3-tert-butylbenzothiazolium-2-carboxylate, 3-octylbenzothiazolium-2-carboxylate, 3-(2-ethyihexyl)benzothiazolium-2-carboxylate, 3-decylbenzothiazolium-2-carboxylate, 3-allylbenzothiazolium-2-carboxylate, 3-benzylbenzothiazolium-2-carboxylate, 3-benzylbenzothiazolium-2-carboxylate, 3-phenylbenzothiazolium-2-carboxylate, 3-(2,6-diisopropylphenyl)benzothiazolium-2-carboxylate, 3-mesitylbenzothiazolium-2-carboxylate, and the like; preferably 1,3-dimethylimidazolium-2-carboxylate, 1-ethyl-3-methylimnidazolium-2-carboxylate, 1-methyl-3-propylimidazolium-2-carboxylate, 1-methyl-3-isopropylimidazolium-2-carboxylate, 1-butyl-3-methylimidazolium-2-carboxylate, 1-tert-butyl-3-methylimidazolium-2-carboxylate, 1-hexyl-3-methylimidazolium-2-carboxylate, 1-methyl-3-octylimidazolium-2-carboxylate, 1-dodecyl-3-methylimidazolium-2-carboxylate, 1-allyl-3-methylimidazolium-2-carboxylate, 1,3-diethylimidazolium-2-carboxylate, 1,3-dipropylimidazolium-2-carboxylate, 1,3-diisopropylimidazolium-2-carboxylate, 1,3-dibutylimidazolium-2-carboxylate, 1,3-di-tert-butylimidazolium-2-carboxylate, 1,3-dihexylimidazolium-2-carboxylate, 1,3-dicyclohexylimidazolium-2-carboxylate, 1,3-dioctylimidazolium-2-carboxylate, 1,3-didodecylimidazolium-2-carboxylate, and 1,3-diphenylimidazolium-2-carboxylate; and particularly preferably 1,3-dimethylimidazolium-2-carboxylate, 1-butyl-3-methylimidazolium-2-carboxylate, and 1-octyl-3-methylimidazolium-2-carboxylate.

Next, specific examples of the nitrogen-containing compound (1b) are shown below. However, the present invention is not limited thereto. In the following specific examples, Et represents an ethyl group, Pr represents an n-propyl group, and Bu represents an n-butyl group.

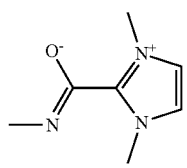

(1b-1-1a)

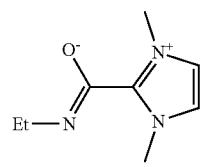

(1b-1-2a)

-continued
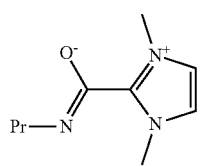
(1b-1-3a)
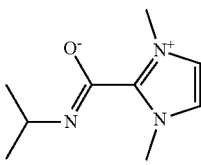
(1b-1-4a)
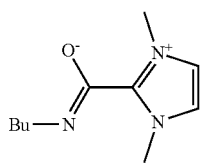
(1b-1-5a)
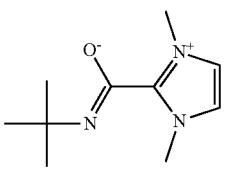
(1b-1-6a)
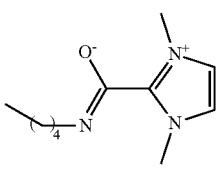
(1b-1-7a)
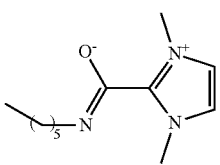
(1b-1-8a)
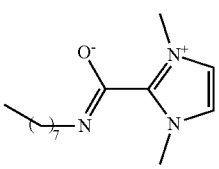
(1b-1-9a)
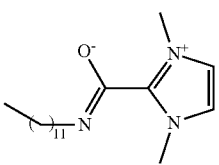
(1b-1-10a)
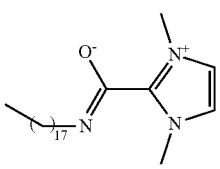
(1b-1-11a)

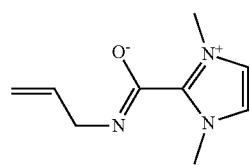
(1b-1-12a)
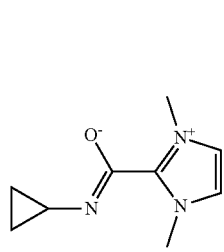
(1b-1-13a)
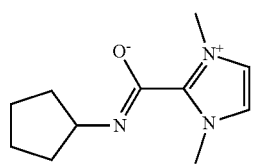
(1b-1-14a)
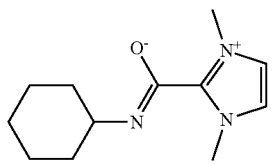 [SMILES: Cn1cc[n+](C)c1/C([O-])=N/C1CCCCC1]
(1b-1-15a)
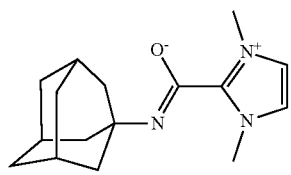 [SMILES: Cn1cc[n+](C)c1/C([O-])=N/C12CC3CC(CC(C3)C1)C2]
(1b-1-16a)
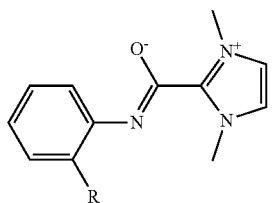
| R = | H | (1b-1-17a) |
|---|---|---|
| | CH₃ | (1b-1-18a) |
| | (CH₂)₃CH₃ | (1b-1-19a) |
| | (CH₂)₇CH₃ | (1b-1-20a) |
| | OCH₃ | (1b-1-21a) |
| | OCH₂CH₃ | (1b-1-22a) |
| | CH(CH₃)₂ | (1b-1-23a) |
| | C(CH₃)₂ | (1b-1-24a) |
| | N(CH₃)₂ | (1b-1-25a) |
| | F | (1b-1-26a) |
| | Cl | (1b-1-27a) |
| | Br | (1b-1-28a) |

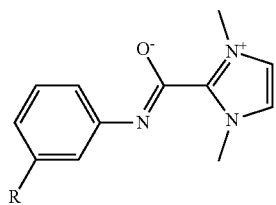
| R = | CH₃ | (1b-1-29a) |
| --- | --- | --- |
| | (CH₂)₃CH₃ | (1b-1-30a) |
| | (CH₂)₇CH₃ | (1b-1-31a) |
| | OCH₃ | (1b-1-32a) |
| | OCH₂CH₃ | (1b-1-33a) |
| | CH(CH₃)₂ | (1b-1-34a) |
| | C(CH₃)₂ | (1b-1-35a) |
| | N(CH₃)₂ | (1b-1-36a) |
| | F | (1b-1-37a) |
| | Cl | (1b-1-38a) |
| | Br | (1b-1-39a) |
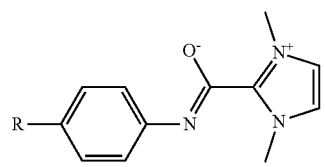
| R = | CH₃ | (1b-1-40a) |
| --- | --- | --- |
| | (CH₂)₃CH₃ | (1b-1-41a) |
| | (CH₂)₇CH₃ | (1b-1-42a) |
| | OCH₃ | (1b-1-43a) |
| | OCH₂CH₃ | (1b-1-44a) |
| | CH(CH₃)₂ | (1b-1-45a) |
| | C(CH₃)₂ | (1b-1-46a) |
| | N(CH₃)₂ | (1b-1-47a) |
| | F | (1b-1-48a) |
| | Cl | (1b-1-49a) |
| | Br | (1b-1-50a) |
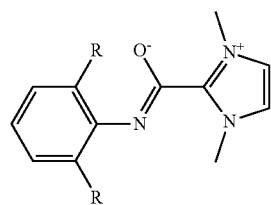
| R = | CH₃ | (1b-1-51a) |
| --- | --- | --- |
| | (CH₂)₃CH₃ | (1b-1-52a) |
| | (CH₂)₇CH₃ | (1b-1-53a) |
| | OCH₃ | (1b-1-54a) |
| | OCH₂CH₃ | (1b-1-55a) |
| | CH(CH₃)₂ | (1b-1-56a) |
| | C(CH₃)₂ | (1b-1-57a) |
| | N(CH₃)₂ | (1b-1-58a) |
| | F | (1b-1-59a) |
| | Cl | (1b-1-60a) |
| | Br | (1b-1-61a) |

-continued
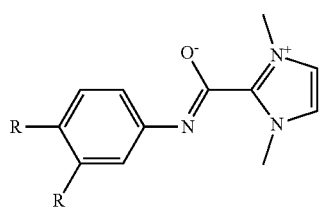
| R = | CH₃ | (1b-1-62a) |
|---|---|---|
| | (CH₂)₃CH₃ | (1b-1-63a) |
| | (CH₂)₇CH₃ | (1b-1-64a) |
| | OCH₃ | (1b-1-65a) |
| | OCH₂CH₃ | (1b-1-66a) |
| | CH(CH₃)₂ | (1b-1-67a) |
| | C(CH₃)₂ | (1b-1-68a) |
| | N(CH₃)₂ | (1b-1-69a) |
| | F | (1b-1-70a) |
| | Cl | (1b-1-71a) |
| | Br | (1b-1-72a) |
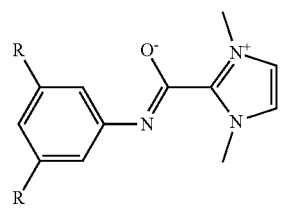
| R = | CH₃ | (1b-1-73a) |
|---|---|---|
| | (CH₂)₃CH₃ | (1b-1-74a) |
| | (CH₂)₇CH₃ | (1b-1-75a) |
| | OCH₃ | (1b-1-76a) |
| | OCH₂CH₃ | (1b-1-77a) |
| | CH(CH₃)₂ | (1b-1-78a) |
| | C(CH₃)₂ | (1b-1-79a) |
| | N(CH₃)₂ | (1b-1-80a) |
| | F | (1b-1-81a) |
| | Cl | (1b-1-82a) |
| | Br | (1b-1-83a) |
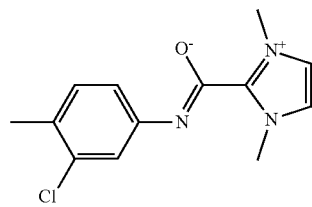 [SMILES: Cc1ccc(/N=C(\[O-])c2n(C)cc[n+]2C)cc1Cl]
(1b-1-84a)
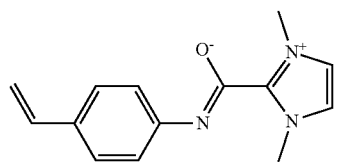 [SMILES: C=Cc1ccc(/N=C(\[O-])c2n(C)cc[n+]2C)cc1]
(1b-1-85a)
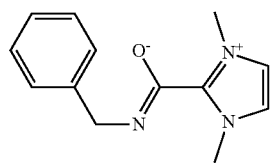 [SMILES: Cn1cc[n+](C)c1/C([O-])=N/Cc1ccccc1]
(1b-1-86a)

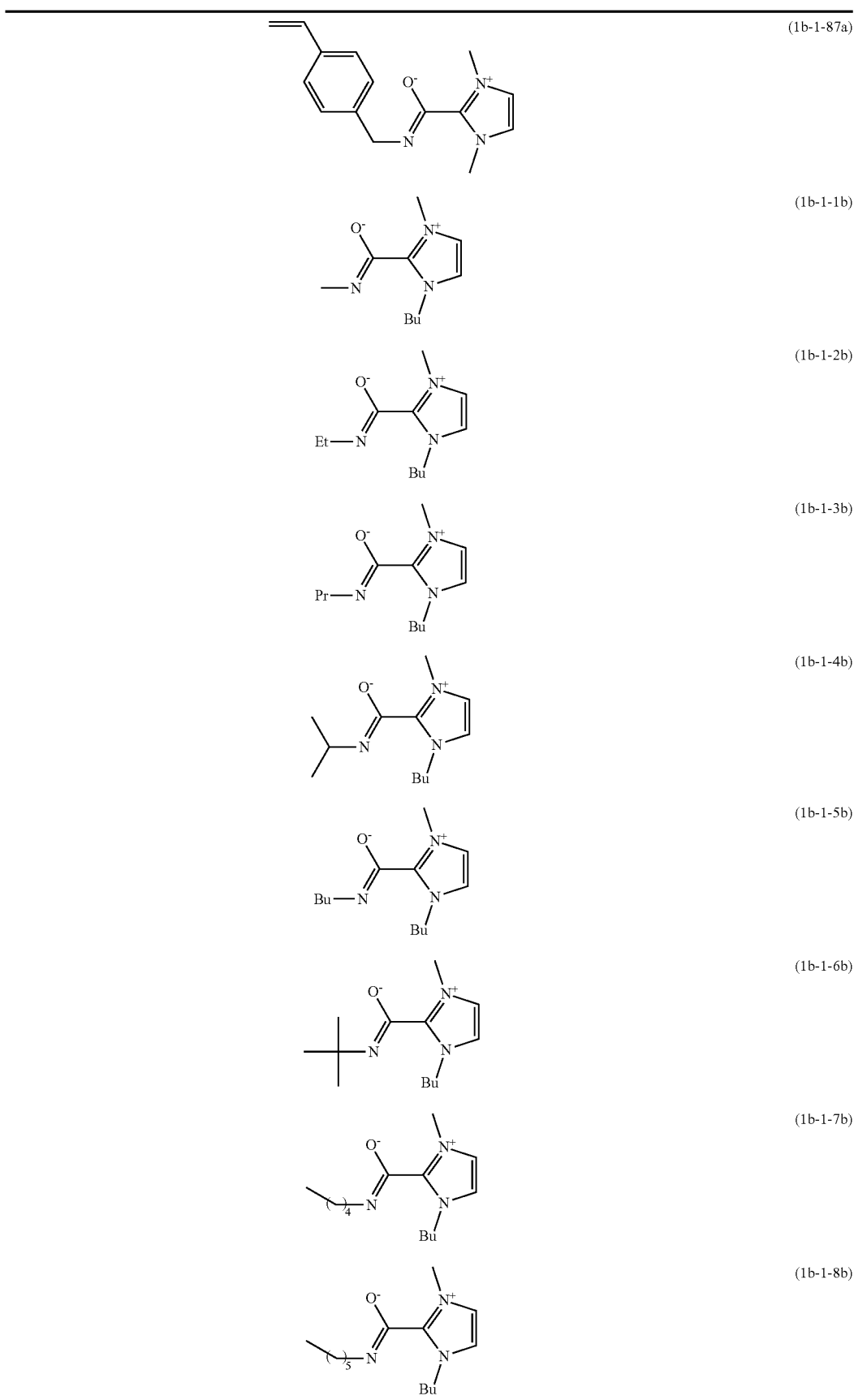

-continued
 (1b-1-9b)
 (1b-1-10b)
 (1b-1-11b)
 (1b-1-12b)
(1b-1-13b)
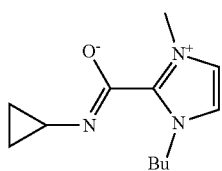
 (1b-1-14b)
(1b-1-15b)
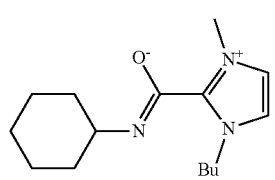
(1b-1-16b)
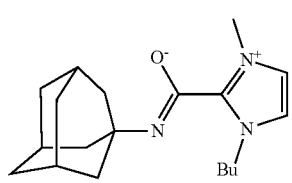

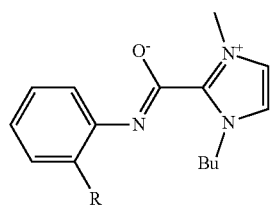
| R = H | (1b-1-17b) |
| CH₃ | (1b-1-18b) |
| (CH₂)₃CH₃ | (1b-1-19b) |
| (CH₂)₇CH₃ | (1b-1-20b) |
| OCH₃ | (1b-1-21b) |
| OCH₂CH₃ | (1b-1-22b) |
| CH(CH₃)₂ | (1b-1-23b) |
| C(CH₃)₂ | (1b-1-24b) |
| N(CH₃)₂ | (1b-1-25b) |
| F | (1b-1-26b) |
| Cl | (1b-1-27b) |
| Br | (1b-1-28b) |
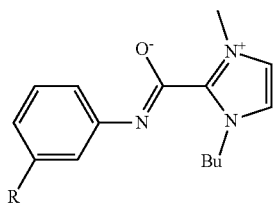
| R = CH₃ | (1b-1-29b) |
| (CH₂)₃CH₃ | (1b-1-30b) |
| (CH₂)₇CH₃ | (1b-1-31b) |
| OCH₃ | (1b-1-32b) |
| OCH₂CH₃ | (1b-1-33b) |
| CH(CH₃)₂ | (1b-1-34b) |
| C(CH₃)₂ | (1b-1-35b) |
| N(CH₃)₂ | (1b-1-36b) |
| F | (1b-1-37b) |
| Cl | (1b-1-38b) |
| Br | (1b-1-39b) |
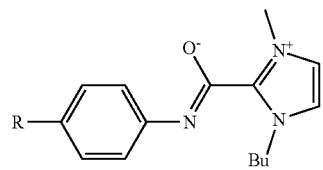
| R = CH₃ | (1b-1-40b) |
| (CH₂)₃CH₃ | (1b-1-41b) |
| (CH₂)₇CH₃ | (1b-1-42b) |
| OCH₃ | (1b-1-43b) |
| OCH₂CH₃ | (1b-1-44b) |
| CH(CH₃)₂ | (1b-1-45b) |
| C(CH₃)₂ | (1b-1-46b) |
| N(CH₃)₂ | (1b-1-47b) |
| F | (1b-1-48b) |
| Cl | (1b-1-49b) |
| Br | (1b-1-50b) |

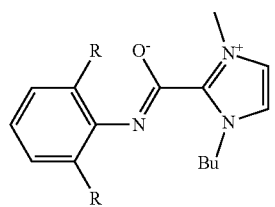
| R = | CH₃ | (1b-1-51b) |
|---|---|---|
| | (CH₂)₃CH₃ | (1b-1-52b) |
| | (CH₂)₇CH₃ | (1b-1-53b) |
| | OCH₃ | (1b-1-54b) |
| | OCH₂CH₃ | (1b-1-55b) |
| | CH(CH₃)₂ | (1b-1-56b) |
| | C(CH₃)₂ | (1b-1-57b) |
| | N(CH₃)₂ | (1b-1-58b) |
| | F | (1b-1-59b) |
| | Cl | (1b-1-60b) |
| | Br | (1b-1-61b) |
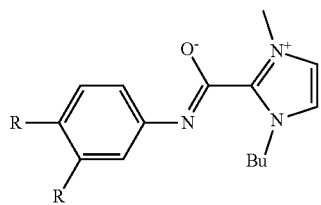
| R = | CH₃ | (1b-1-62b) |
|---|---|---|
| | (CH₂)₃CH₃ | (1b-1-63b) |
| | (CH₂)₇CH₃ | (1b-1-64b) |
| | OCH₃ | (1b-1-65b) |
| | OCH₂CH₃ | (1b-1-66b) |
| | CH(CH₃)₂ | (1b-1-67b) |
| | C(CH₃)₂ | (1b-1-68b) |
| | N(CH₃)₂ | (1b-1-69b) |
| | F | (1b-1-70b) |
| | Cl | (1b-1-71b) |
| | Br | (1b-1-72b) |
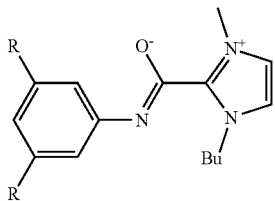
| R = | CH₃ | (1b-1-73b) |
|---|---|---|
| | (CH₂)₃CH₃ | (1b-1-74b) |
| | (CH₂)₇CH₃ | (1b-1-75b) |
| | OCH₃ | (1b-1-76b) |
| | OCH₂CH₃ | (1b-1-77b) |
| | CH(CH₃)₂ | (1b-1-78b) |
| | C(CH₃)₂ | (1b-1-79b) |
| | N(CH₃)₂ | (1b-1-80b) |
| | F | (1b-1-81b) |
| | Cl | (1b-1-82b) |
| | Br | (1b-1-83b) |
(1b-1-84b)
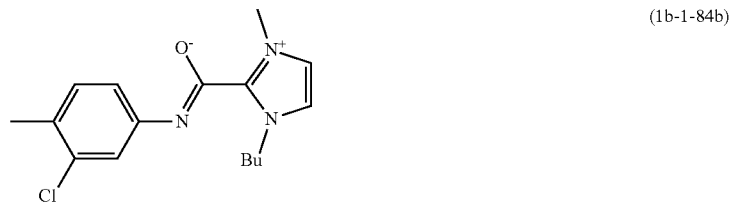

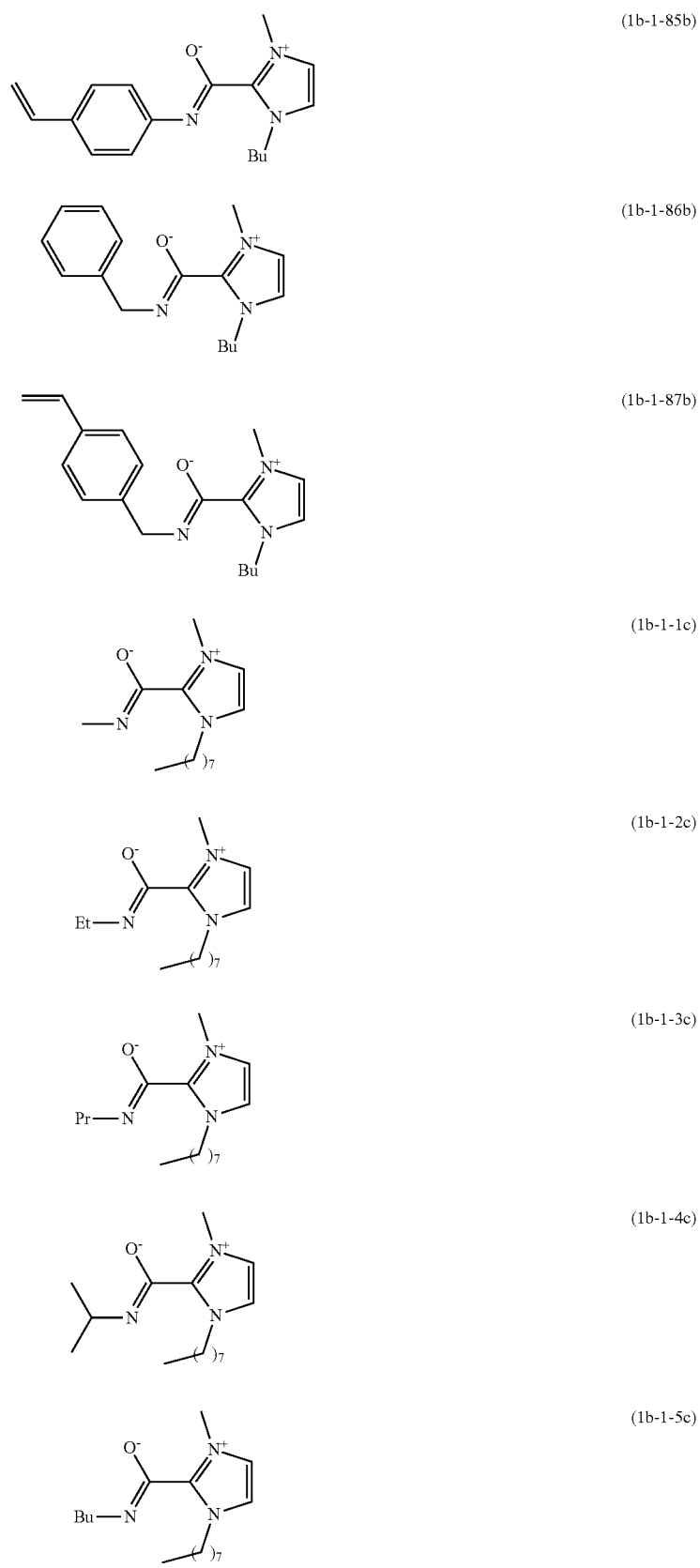

-continued
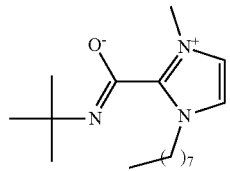
(1b-1-6c)
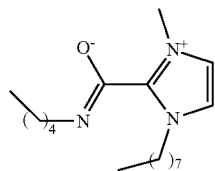
(1b-1-7c)
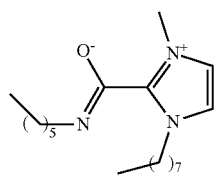
(1b-1-8c)
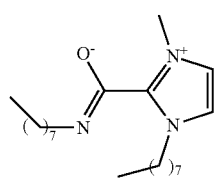
(1b-1-9c)
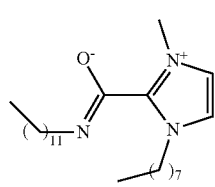
(1b-1-10c)
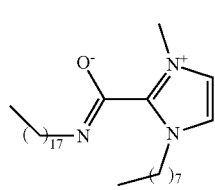
(1b-1-11c)
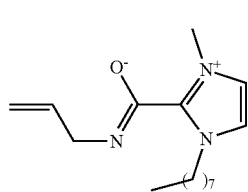
(1b-1-12c)
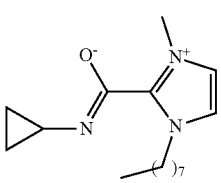
(1b-1-13c)

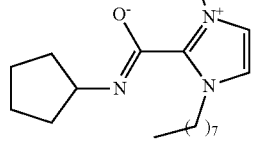
(1b-1-14c)
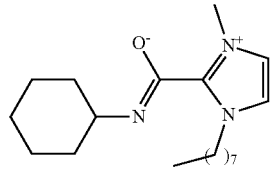
(1b-1-15c)
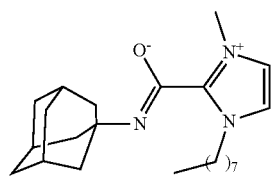
(1b-1-16c)
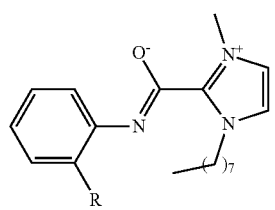
| R = | H | (1b-1-17c) |
|---|---|---|
| | CH$_3$ | (1b-1-18c) |
| | (CH$_2$)$_3$CH$_3$ | (1b-1-19c) |
| | (CH$_2$)$_7$CH$_3$ | (1b-1-20c) |
| | OCH$_3$ | (1b-1-21c) |
| | OCH$_2$CH$_3$ | (1b-1-22c) |
| | CH(CH$_3$)$_2$ | (1b-1-23c) |
| | C(CH$_3$)$_2$ | (1b-1-24c) |
| | N(CH$_3$)$_2$ | (1b-1-25c) |
| | F | (1b-1-26c) |
| | Cl | (1b-1-27c) |
| | Br | (1b-1-28c) |
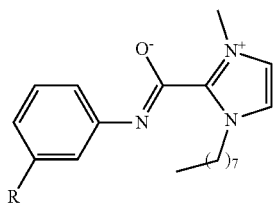
| R = | CH$_3$ | (1b-1-29c) |
|---|---|---|
| | (CH$_2$)$_3$CH$_3$ | (1b-1-30c) |
| | (CH$_2$)$_7$CH$_3$ | (1b-1-31c) |
| | OCH$_3$ | (1b-1-32c) |
| | OCH$_2$CH$_3$ | (1b-1-33c) |
| | CH(CH$_3$)$_2$ | (1b-1-34c) |
| | C(CH$_3$)$_2$ | (1b-1-35c) |
| | N(CH$_3$)$_2$ | (1b-1-36c) |
| | F | (1b-1-37c) |
| | Cl | (1b-1-38c) |
| | Br | (1b-1-39c) |

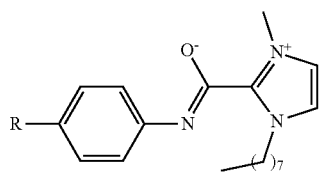
| R = | CH₃ | (1b-1-40c) |
| | (CH₂)₃CH₃ | (1b-1-41c) |
| | (CH₂)₇CH₃ | (1b-1-42c) |
| | OCH₃ | (1b-1-43c) |
| | OCH₂CH₃ | (1b-1-44c) |
| | CH(CH₃)₂ | (1b-1-45c) |
| | C(CH₃)₂ | (1b-1-46c) |
| | N(CH₃)₂ | (1b-1-47c) |
| | F | (1b-1-48c) |
| | Cl | (1b-1-49c) |
| | Br | (1b-1-50c) |
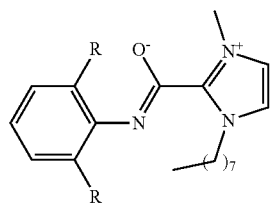
| R = | CH₃ | (1b-1-51c) |
| | (CH₂)₃CH₃ | (1b-1-52c) |
| | (CH₂)₇CH₃ | (1b-1-53c) |
| | OCH₃ | (1b-1-54c) |
| | OCH₂CH₃ | (1b-1-55c) |
| | CH(CH₃)₂ | (1b-1-56c) |
| | C(CH₃)₂ | (1b-1-57c) |
| | N(CH₃)₂ | (1b-1-58c) |
| | F | (1b-1-59c) |
| | Cl | (1b-1-60c) |
| | Br | (1b-1-61c) |
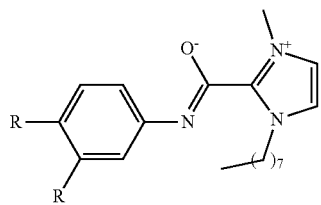
| R = | CH₃ | (1b-1-62c) |
| | (CH₂)₃CH₃ | (1b-1-63c) |
| | (CH₂)₇CH₃ | (1b-1-64c) |
| | OCH₃ | (1b-1-65c) |
| | OCH₂CH₃ | (1b-1-66c) |
| | CH(CH₃)₂ | (1b-1-67c) |
| | C(CH₃)₂ | (1b-1-68c) |
| | N(CH₃)₂ | (1b-1-69c) |
| | F | (1b-1-70c) |
| | Cl | (1b-1-71c) |
| | Br | (1b-1-72c) |

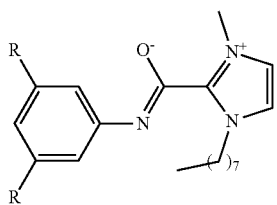
| R = | CH₃ | (1b-1-73c) |
|---|---|---|
| | (CH₂)₃CH₃ | (1b-1-74c) |
| | (CH₂)₇CH₃ | (1b-1-75c) |
| | OCH₃ | (1b-1-76c) |
| | OCH₂CH₃ | (1b-1-77c) |
| | CH(CH₃)₂ | (1b-1-78c) |
| | C(CH₃)₂ | (1b-1-79c) |
| | N(CH₃)₂ | (1b-1-80c) |
| | F | (1b-1-81c) |
| | Cl | (1b-1-82c) |
| | Br | (1b-1-83c) |
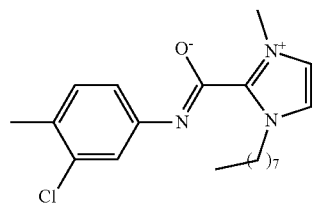
(1b-1-84c)
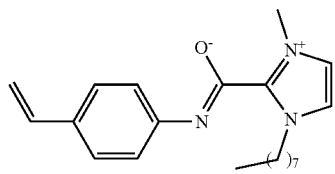
(1b-1-85c)
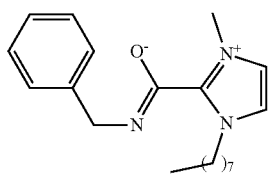
(1b-1-86c)
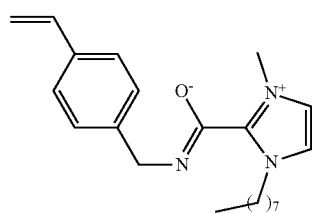
(1b-1-87c)

-continued
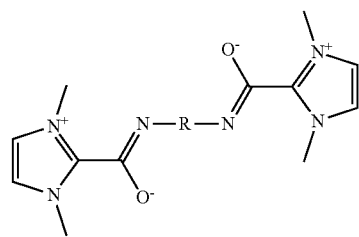
R = —CH₂CH₂— (1b-2-1a)
—CH₂(CH₂)₃CH₂— (1b-2-2a)
—CH₂(CH₂)₄CH₂— (1b-2-3a)
—CH₂(CH₂)₆CH₂— (1b-2-4a)
—CH₂(CH₂)₈CH₂— (1b-2-5a)
—CH₂(CH₂)₁₀CH₂— (1b-2-6a)
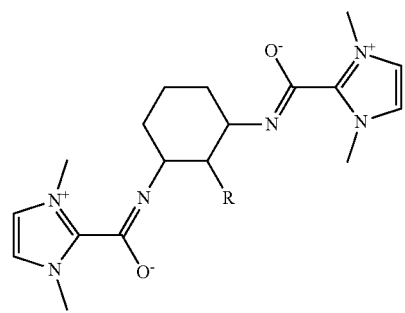
R = H (1b-2-7a)
CH₃ (1b-2-8a)
(1b-2-9a)
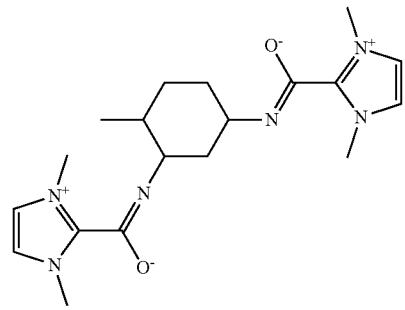 [SMILES: CC1CCC(/N=C(\[O-])c2n(C)cc[n+]2C)CC1N=C([O-])c1n(C)cc[n+]1C]
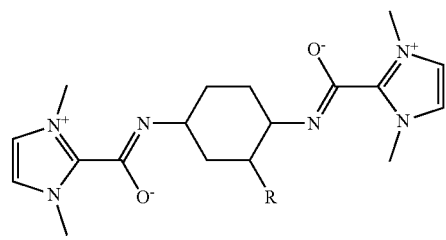
R = H (1b-2-10a)
CH₃ (1b-2-11a)

-continued
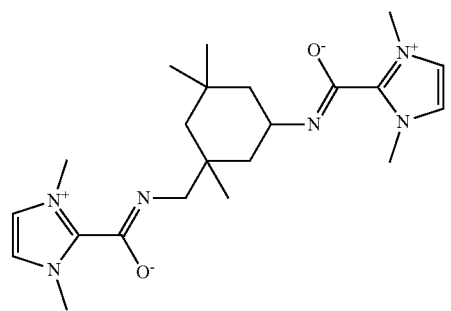 [SMILES: Cn1cc[n+](C)c1/C([O-])=N/CC1(C)CC(/N=C(\[O-])c2n(C)cc[n+]2C)CC(C)(C)C1]
(1b-2-12a)
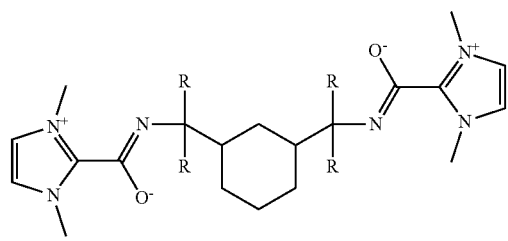
R = H (1b-2-13a)
CH₃ (1b-2-14a)
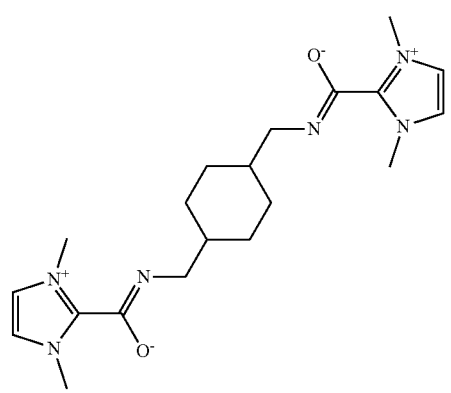 [SMILES: Cn1cc[n+](C)c1/C([O-])=N/CC1CCC(C/N=C(\[O-])c2n(C)cc[n+]2C)CC1]
(1b-2-15a)
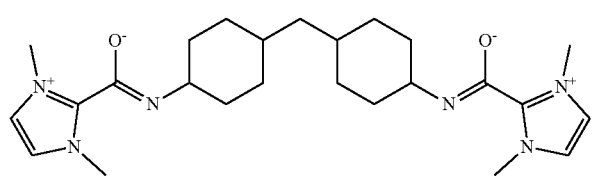 [SMILES: Cn1cc[n+](C)c1/C([O-])=N/C1CCC(CC2CCC(/N=C(\[O-])c3n(C)cc[n+]3C)CC2)CC1]
(1b-2-16a)
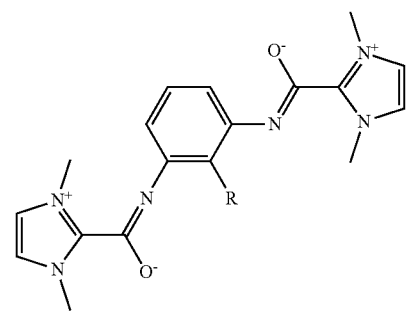
R = H (1b-2-17a)
CH₃ (1b-2-18a)

(1b-2-19a)
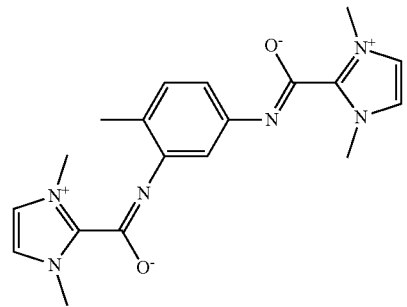 [SMILES: Cc1ccc(/N=C(\[O-])c2n(C)cc[n+]2C)cc1N=C([O-])c1n(C)cc[n+]1C]
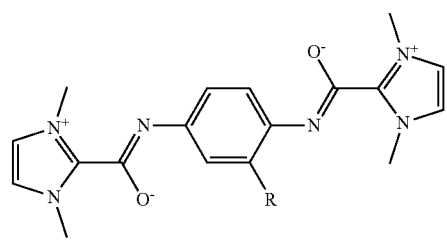
R = H   (1b-2-20a)
CH₃ (1b-2-21a)
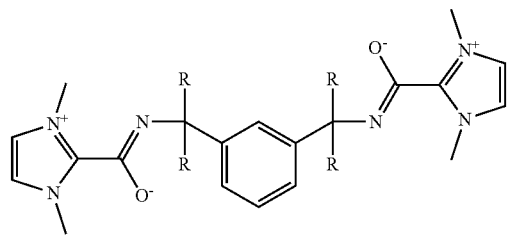
R = H   (1b-2-22a)
CH₃ (1b-2-23a)
(1b-2-24a)
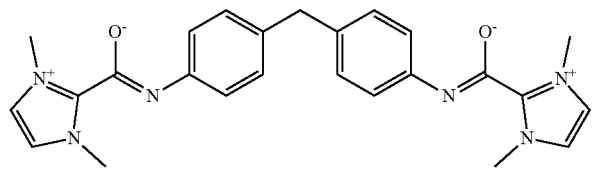 [SMILES: Cn1cc[n+](C)c1/C([O-])=N/c1ccc(Cc2ccc(/N=C(\[O-])c3n(C)cc[n+]3C)cc2)cc1]
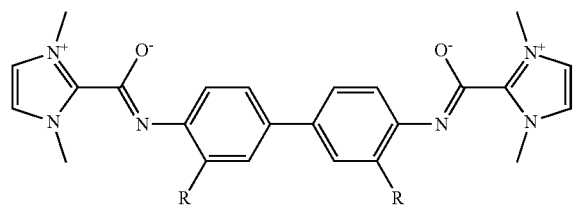
R = CH₃     (1b-2-25a)
CH₂CH₃  (1b-2-26a)
OCH₃     (1b-2-27a)

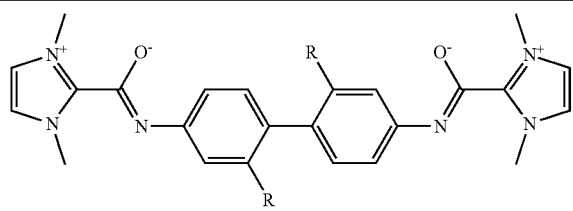
R = CH₃ (1b-2-28a)
CH₂CH₃ (1b-2-29a)
OCH₃ (1b-2-30a)
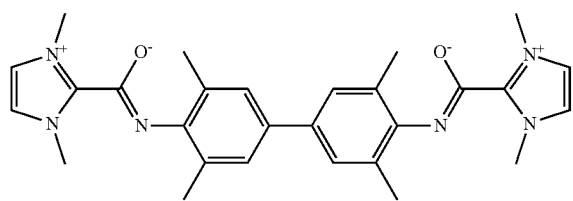 [SMILES: Cc1cc(-c2cc(C)c(/N=C(\[O-])c3n(C)cc[n+]3C)c(C)c2)cc(C)c1/N=C(\[O-])c1n(C)cc[n+]1C]
(1b-2-31a)
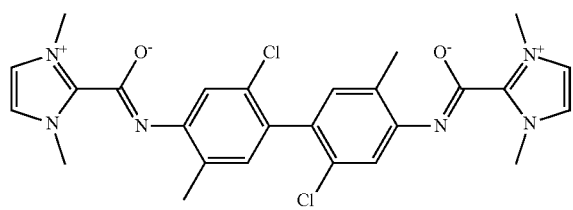 [SMILES: Cc1cc(-c2cc(C)c(/N=C(\[O-])c3n(C)cc[n+]3C)cc2Cl)c(Cl)cc1/N=C(\[O-])c1n(C)cc[n+]1C]
(1b-2-32a)
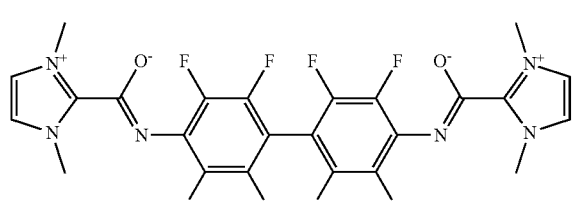
(1b-2-33a)
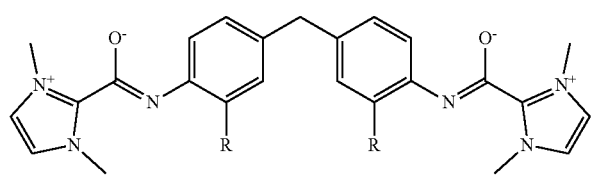
R = CH₃ (1b-2-34a)
Cl (1b-2-35a)
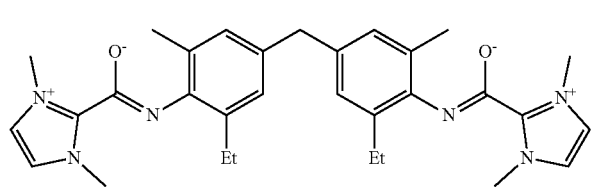 [SMILES: CCc1cc(Cc2cc(C)c(/N=C(\[O-])c3n(C)cc[n+]3C)c(CC)c2)cc(C)c1/N=C(\[O-])c1n(C)cc[n+]1C]
(1b-2-36a)
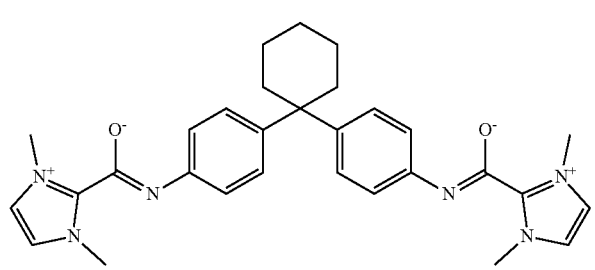 [SMILES: Cn1cc[n+](C)c1/C([O-])=N/c1ccc(C2(c3ccc(/N=C(\[O-])c4n(C)cc[n+]4C)cc3)CCCCC2)cc1]
(1b-2-37a)

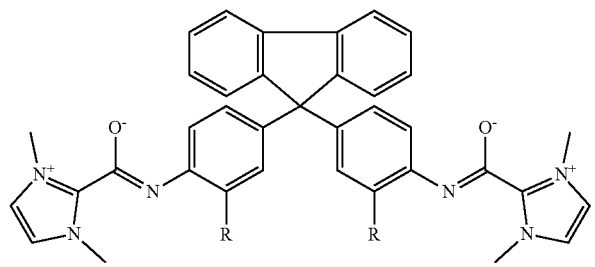
R = H    (1b-2-38a)
    CH₃ (1b-2-39a)
    F    (1b-2-40a)
    Cl   (1b-2-41a)
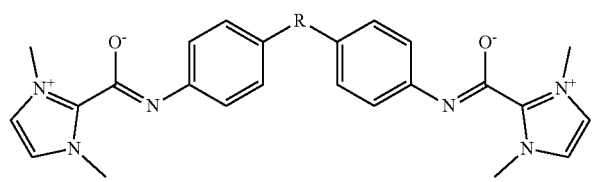
R = O   (1b-2-42a)
    S    (1b-2-43a)
(1b-2-44a)
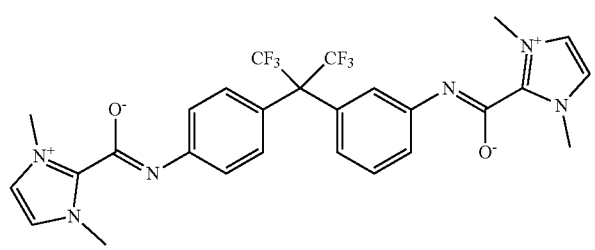 [SMILES: Cn1cc[n+](C)c1/C([O-])=N/c1ccc(C(c2cccc(/N=C(\[O-])c3n(C)cc[n+]3C)c2)(C(F)(F)F)C(F)(F)F)cc1]
(1b-2-45a)
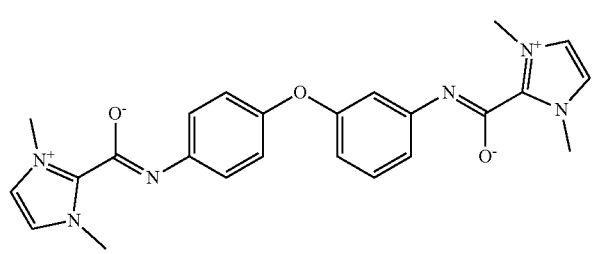 [SMILES: Cn1cc[n+](C)c1/C([O-])=N/c1ccc(Oc2cccc(/N=C(\[O-])c3n(C)cc[n+]3C)c2)cc1]
(1b-2-46a)
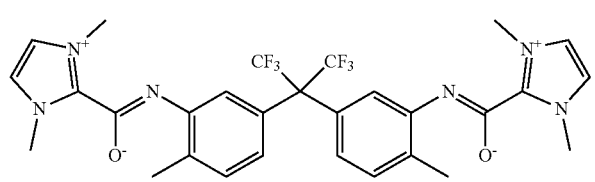 [SMILES: Cc1ccc(C(c2ccc(C)c(/N=C(\[O-])c3n(C)cc[n+]3C)c2)(C(F)(F)F)C(F)(F)F)cc1/N=C(\[O-])c1n(C)cc[n+]1C]
(1b-2-47a)
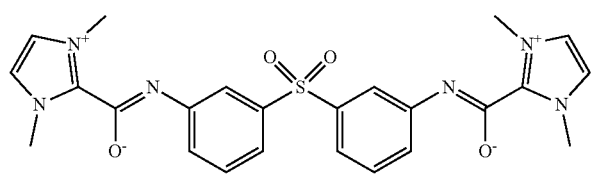 [SMILES: Cn1cc[n+](C)c1/C([O-])=N/c1cccc(S(=O)(=O)c2cccc(/N=C(\[O-])c3n(C)cc[n+]3C)c2)c1]

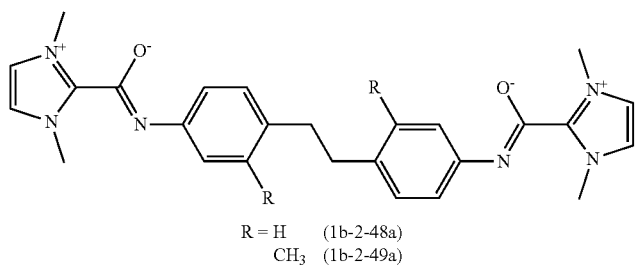
R = H (1b-2-48a)
CH₃ (1b-2-49a)
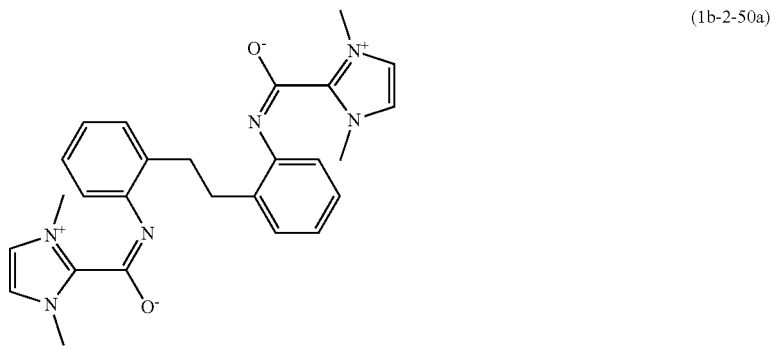
(1b-2-50a)
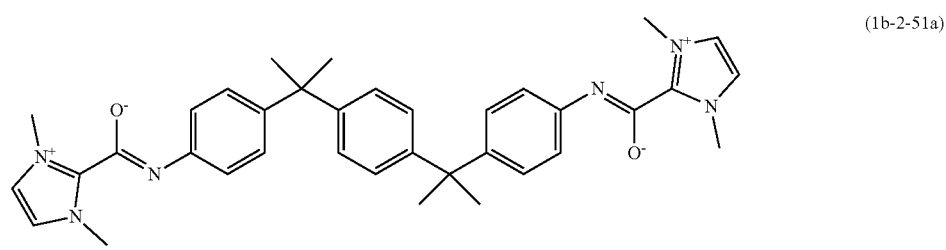
(1b-2-51a)
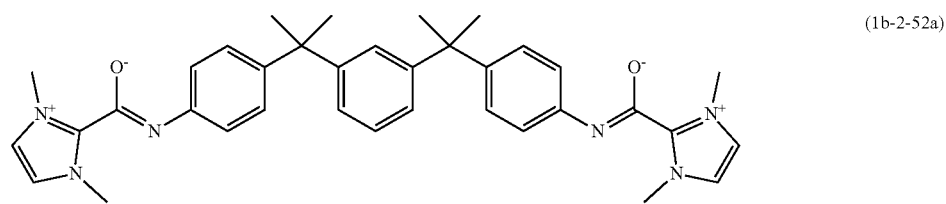
(1b-2-52a)
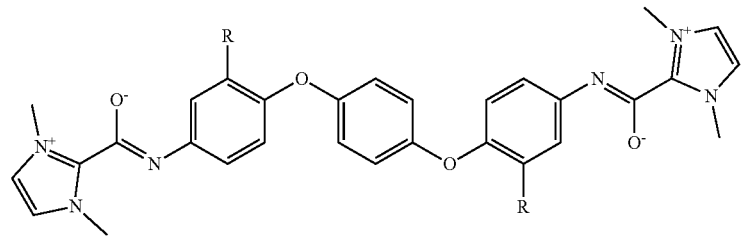 [SMILES: Cn1cc[n+](C)c1/C([O-])=N/c1ccc(C(C)(C)c2ccc(C(C)(C)c3ccc(/N=C(\[O-])c4n(C)cc[n+]4C)cc3)cc2)cc1]
R = H (1b-2-53a)
CF₃ (1b-2-54a)
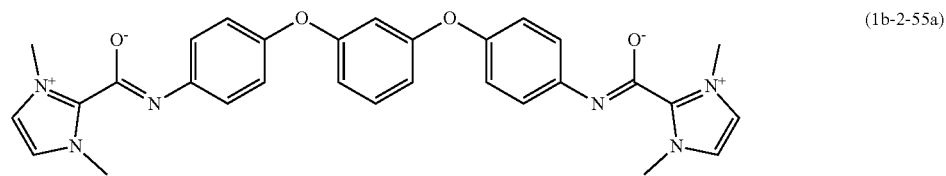
(1b-2-55a)

-continued
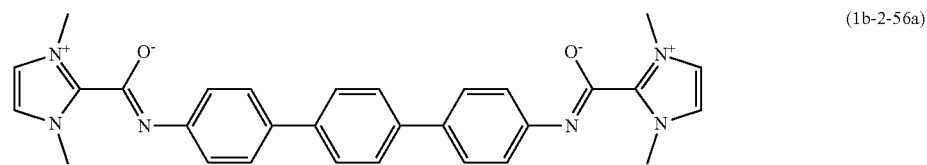
(1b-2-56a)
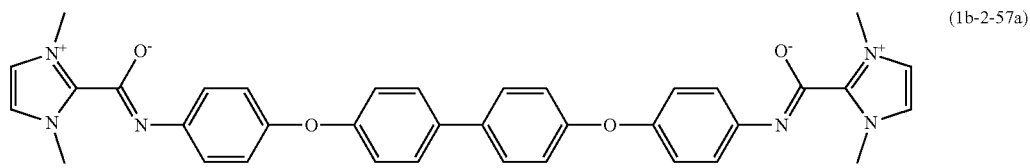
(1b-2-57a)
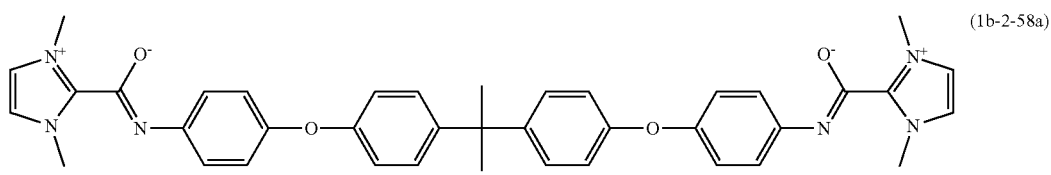
(1b-2-58a)
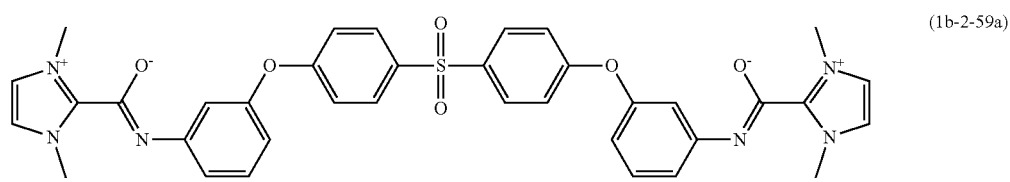
(1b-2-59a)
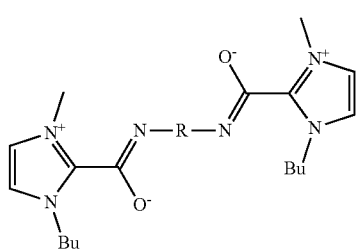
R = —CH$_2$CH$_2$— (1b-2-1b)
—CH$_2$(CH$_2$)$_2$CH$_2$— (1b-2-2b)
—CH$_2$(CH$_2$)$_4$CH$_2$— (1b-2-3b)
—CH$_2$(CH$_2$)$_6$CH$_2$— (1b-2-4b)
—CH$_2$(CH$_2$)$_8$CH$_2$— (1b-2-5b)
—CH$_2$(CH$_2$)$_{10}$CH$_2$— (1b-2-6b)
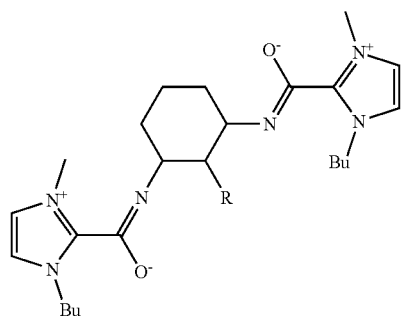
R = H (1b-2-7b)
CH$_3$ (1b-2-8b)

(1b-2-9b)
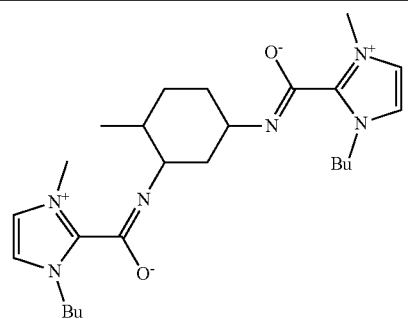
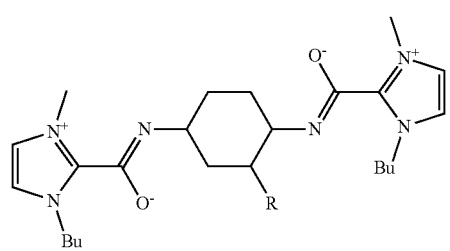
R = H (1b-2-10b)
CH₃ (1b-2-11b)
(1b-2-12b)
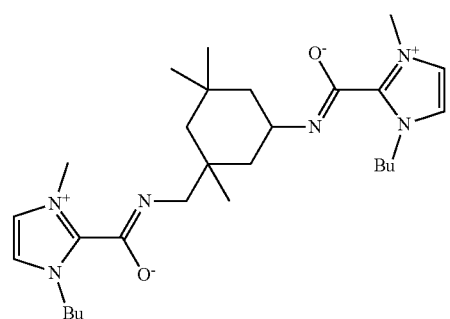
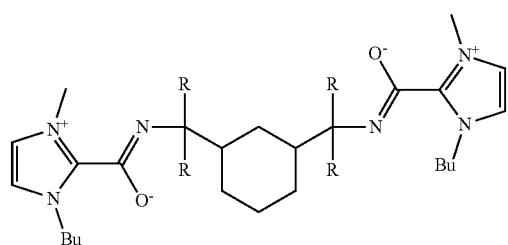
R = H (1b-2-13b)
CH₃ (1b-2-14b)

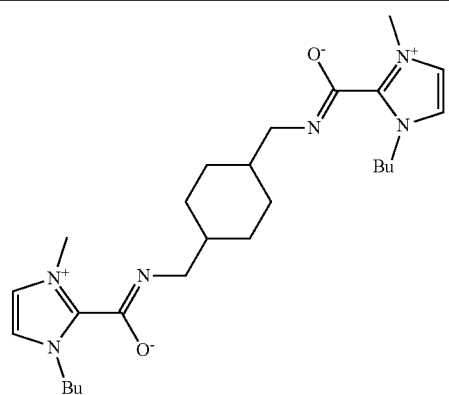
(1b-2-15b)
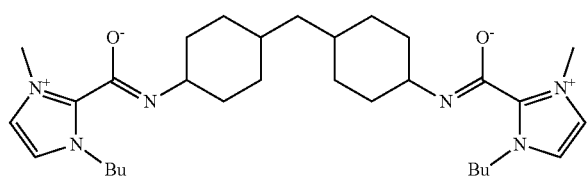
(1b-2-16b)
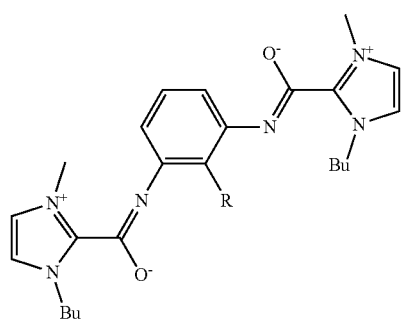
R = H   (1b-2-17b)
CH₃  (1b-2-18b)
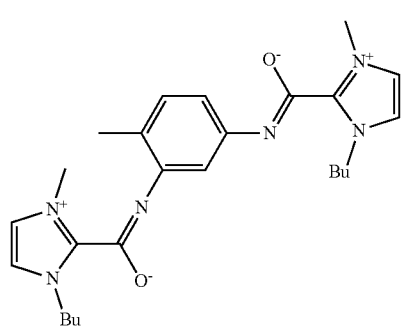
(1b-2-19b)
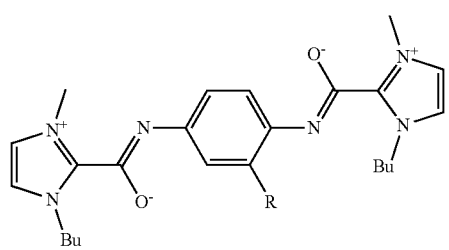
R = H   (1b-2-20b)
CH₃  (1b-2-21b)

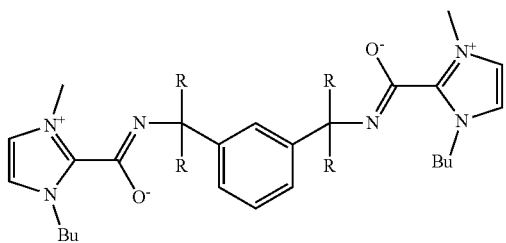
R = H      (1b-2-22b)
CH₃   (1b-2-23b)
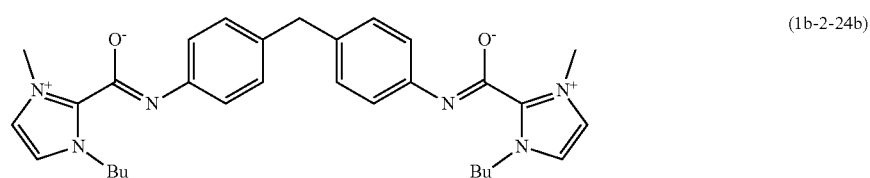
(1b-2-24b)
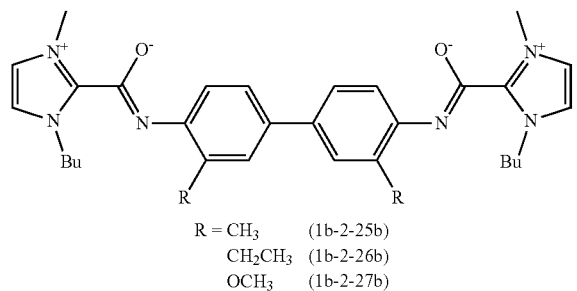
R = CH₃       (1b-2-25b)
CH₂CH₃   (1b-2-26b)
OCH₃       (1b-2-27b)
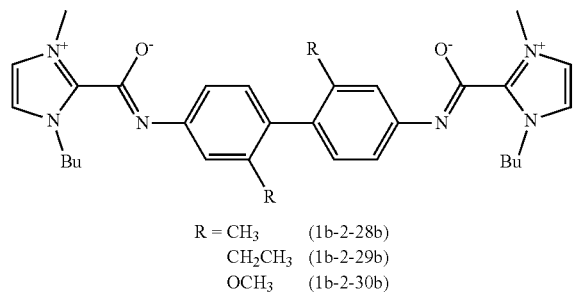
R = CH₃       (1b-2-28b)
CH₂CH₃   (1b-2-29b)
OCH₃       (1b-2-30b)
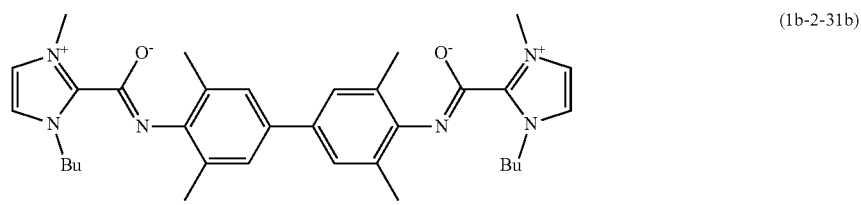
(1b-2-31b)
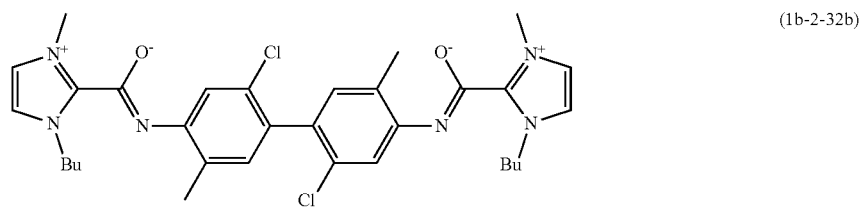
(1b-2-32b)

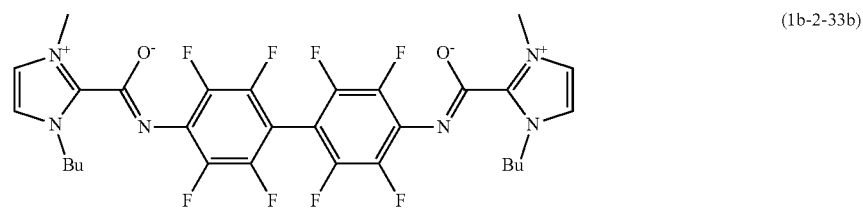
(1b-2-33b)
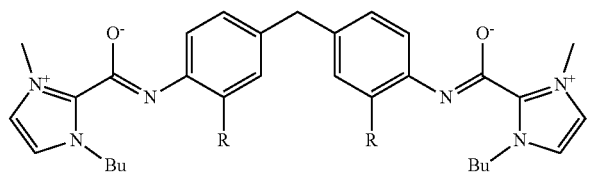
R = CH₃ (1b-2-34b)
Cl (1b-2-35b)
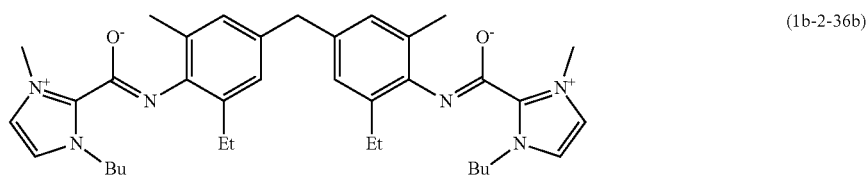
(1b-2-36b)
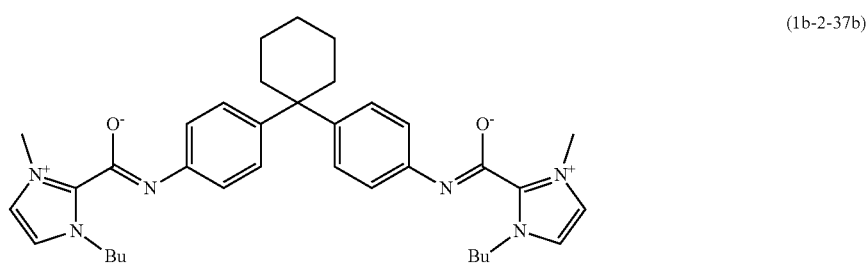
(1b-2-37b)
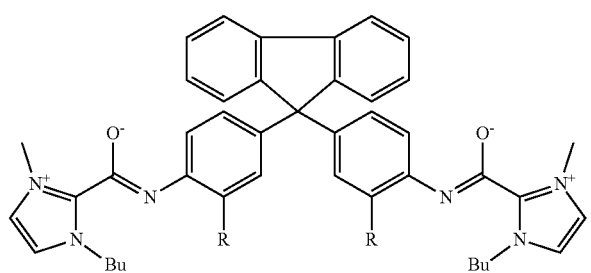
R = H (1b-2-38b)
CH₃ (1b-2-39b)
F (1b-2-40b)
Cl (1b-2-41b)
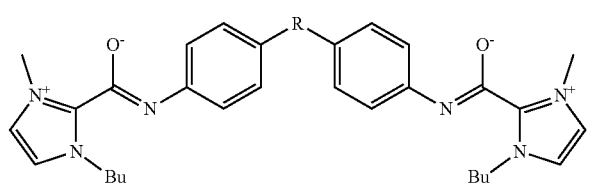
R = O (1b-2-42b)
S (1b-2-43b)

-continued
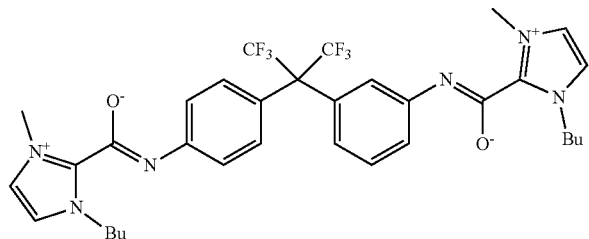 (1b-2-44b)
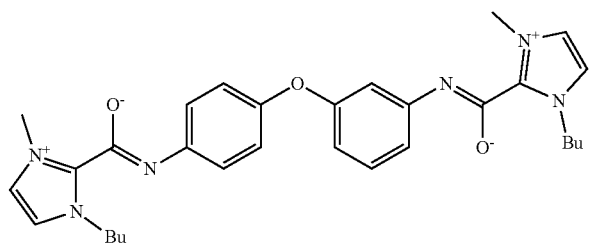 (1b-2-45b)
(1b-2-46b)
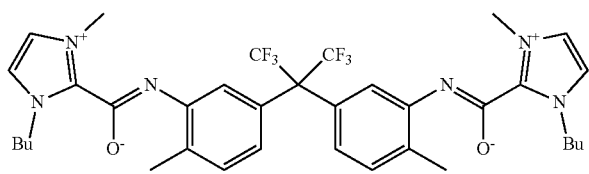
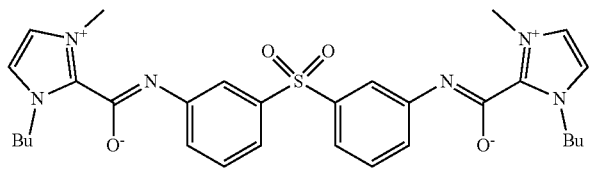 (1b-2-47b)
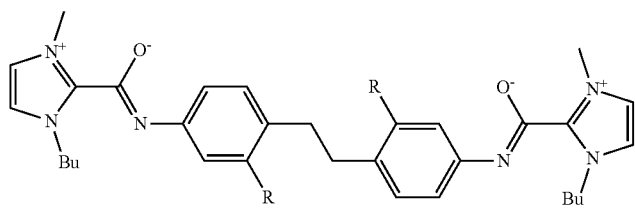
R = H (1b-2-48b)
CH₃ (1b-2-49b)
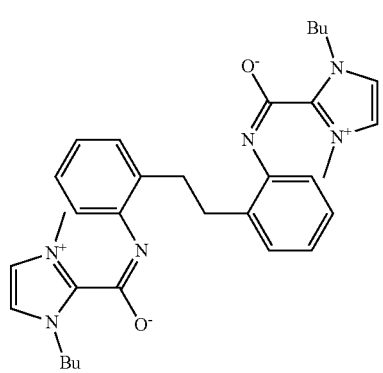 (1b-2-50b)

-continued
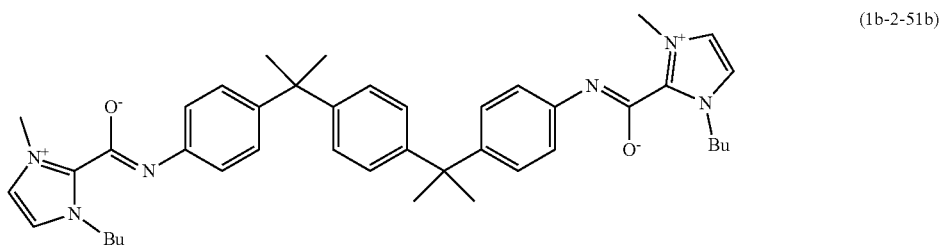
(1b-2-51b)
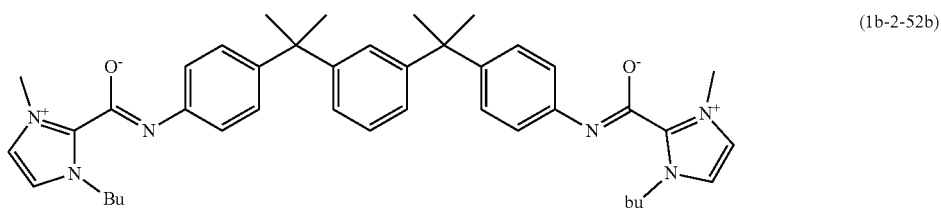
(1b-2-52b)
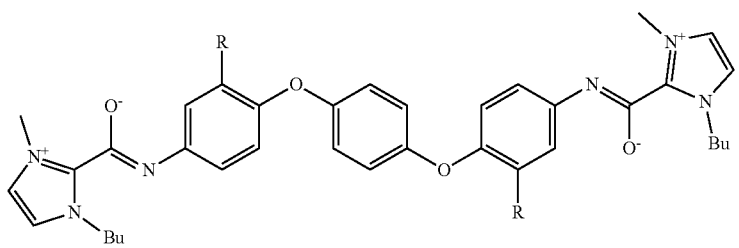
R = H  (1b-2-53b)
CF₃  (1b-2-54b)
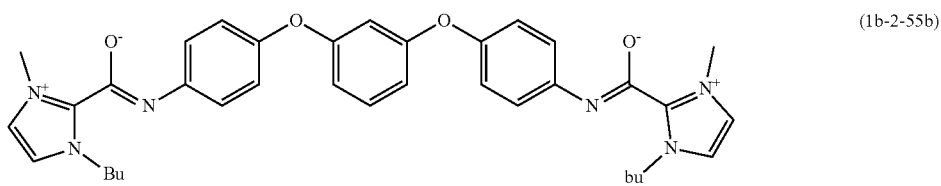
(1b-2-55b)
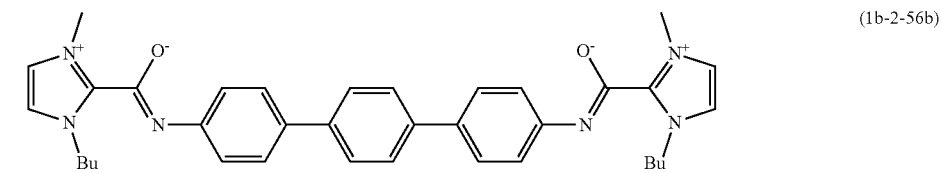
(1b-2-56b)
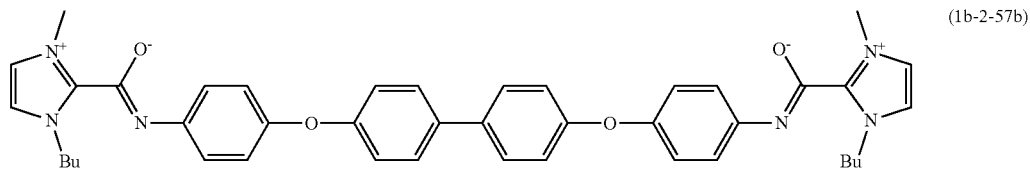
(1b-2-57b)
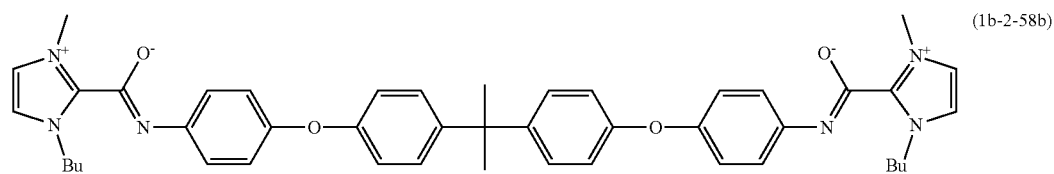
(1b-2-58b)

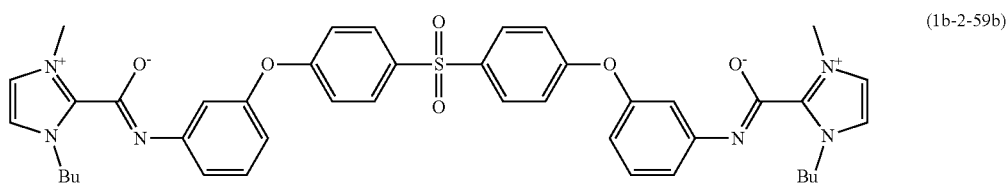
(1b-2-59b)
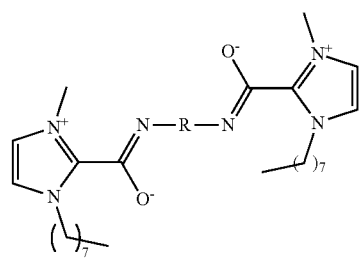
| R = | |
|---|---|
| —CH₂CH₂— | (1b-2-1c) |
| —CH₂(CH₃)₂CH₂— | (1b-2-2c) |
| —CH₂(CH₂)₄CH₂— | (1b-2-3c) |
| —CH₂(CH₂)₆CH₂— | (1b-2-4c) |
| —CH₂(CH₂)₈CH₂— | (1b-2-5c) |
| —CH₂(CH₂)₁₀CH₂— | (1b-2-6c) |
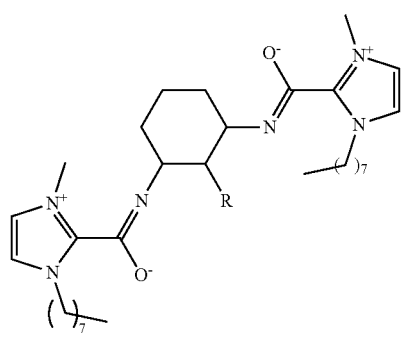
R = H   (1b-2-7c)
    CH₃ (1b-2-8c)
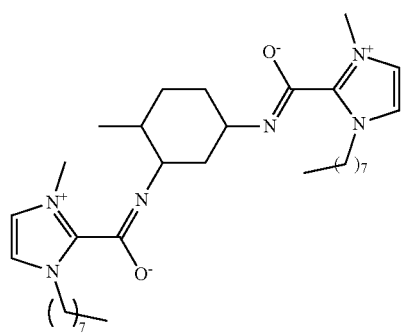
(1b-2-9c)

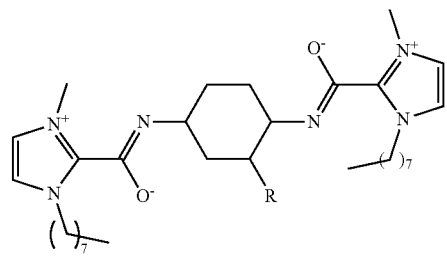
R = H    (1b-2-10c)
CH₃  (1b-2-11c)
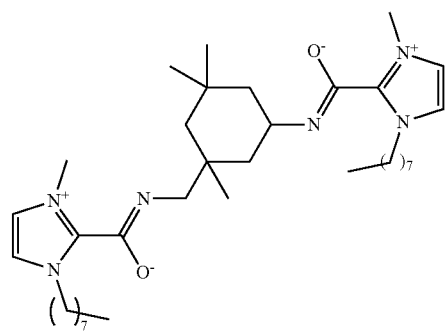
(1b-2-12c)
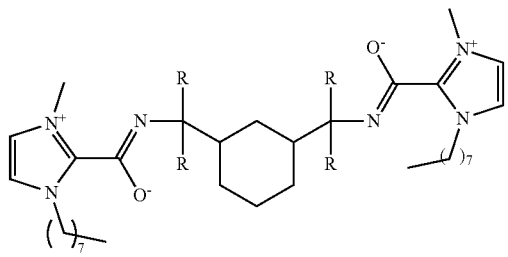
R = H    (1b-2-13c)
CH₃  (1b-2-13c)
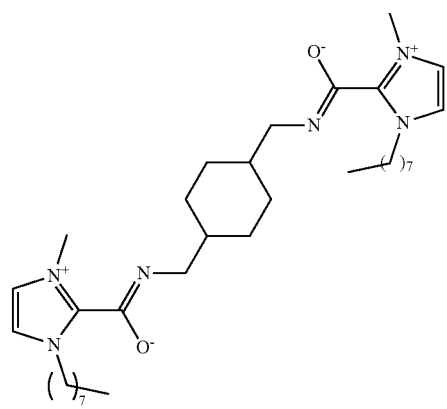
(1b-2-15c)
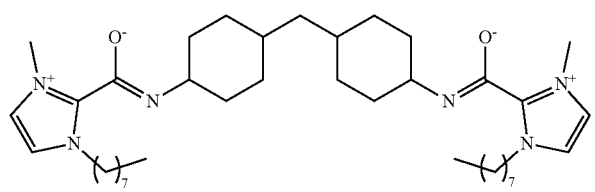
(1b-2-16c)

-continued
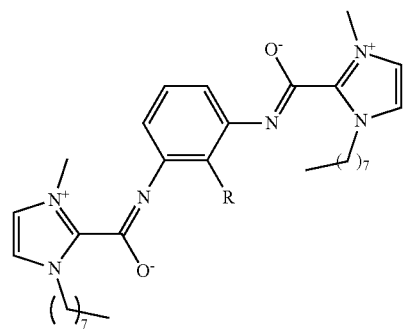
R = H    (1b-2-17c)
CH₃  (1b-2-18c)
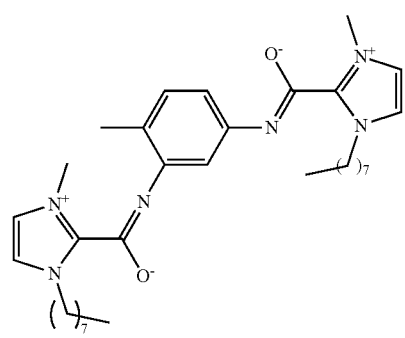
(1b-2-19c)
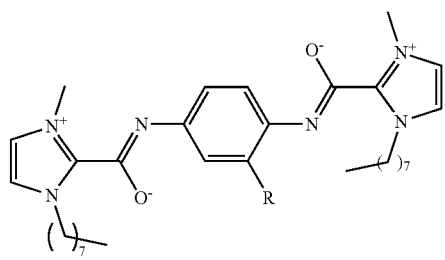
R = H    (1b-2-20c)
CH₃  (1b-2-21c)
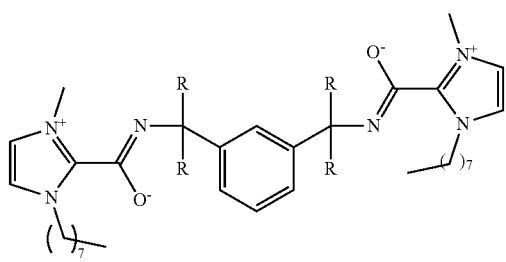
R = H    (1b-2-22c)
CH₃  (1b-2-23c)
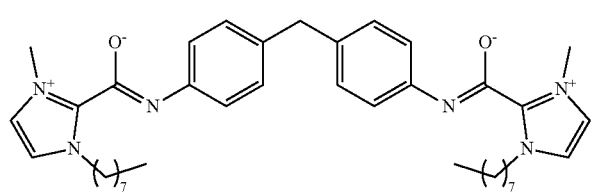
(1b-2-24c)

-continued
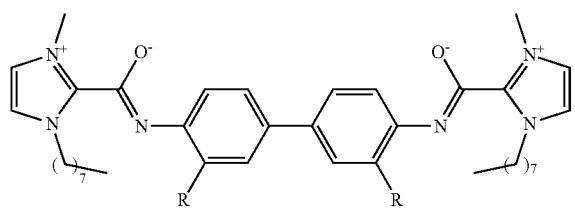
R = CH₃ (1b-2-25c)
CH₂CH₃ (1b-2-26c)
OCH₃ (1b-2-27c)
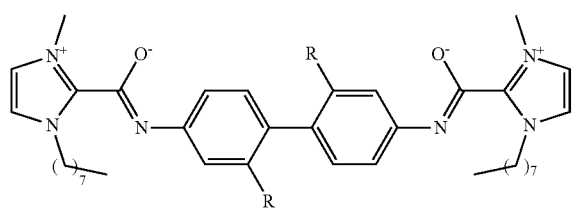
R = CH₃ (1b-2-28c)
CH₂CH₃ (1b-2-29c)
OCH₃ (1b-2-30c)
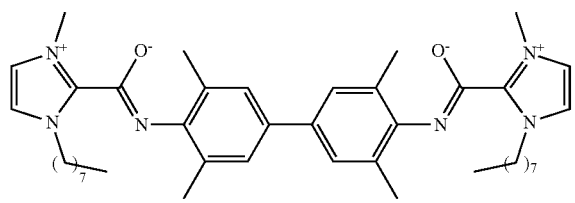
(1b-2-31c)
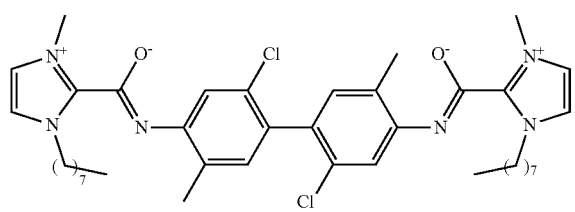
(1b-2-32c)
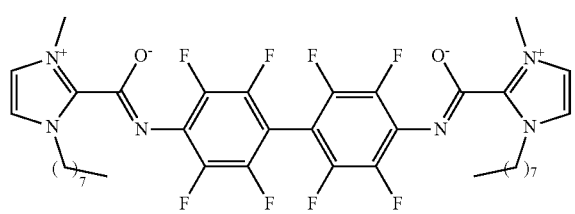
(1b-2-33c)
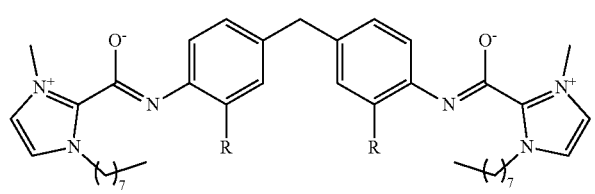
R = CH₃ (1b-2-34c)
Cl (1b-2-35c)

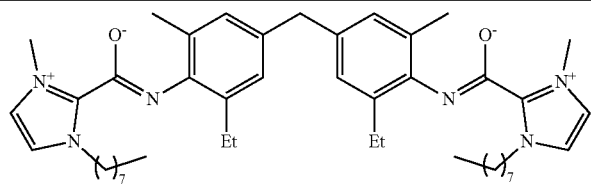
(1b-2-36c)
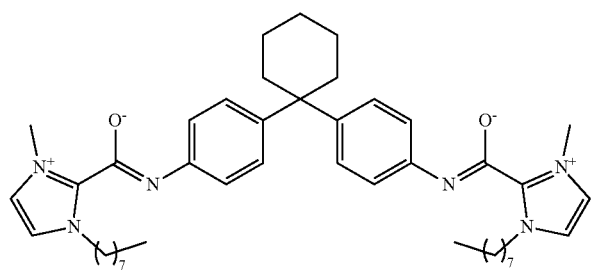
(1b-2-37c)
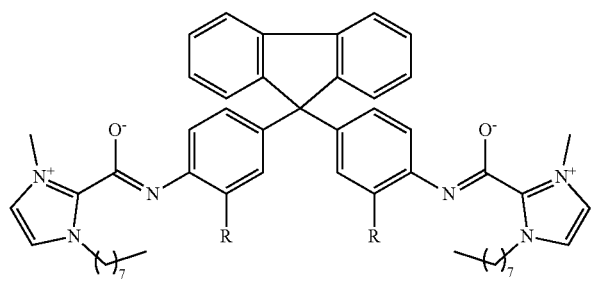
R = H (1b-2-38c)
CH₃ (1b-2-39c)
F (1b-2-40c)
Cl (1b-2-41c)
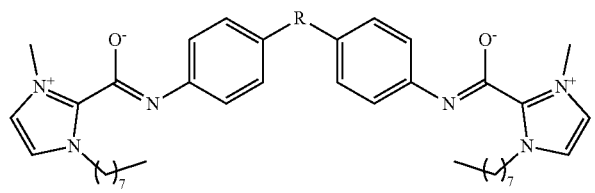
R = O (1b-2-42c)
S (1b-2-43c)
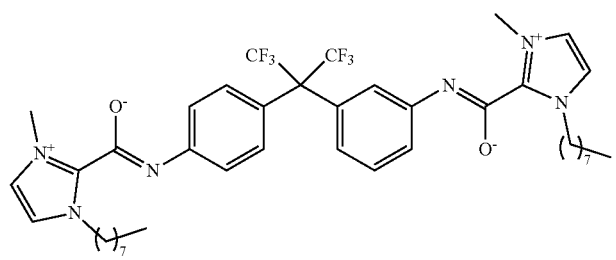
(1b-2-44c)
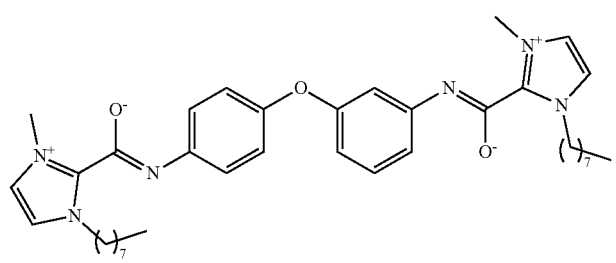
(1b-2-45c)

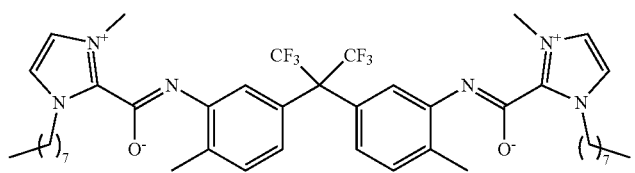
(1b-2-46c)
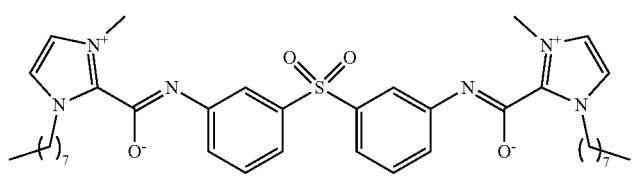
(1b-2-47c)
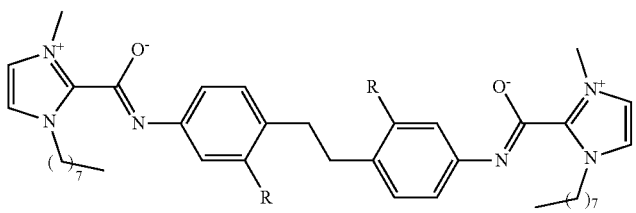
R = H (1b-2-48c)
CH₃ (1b-2-49c)
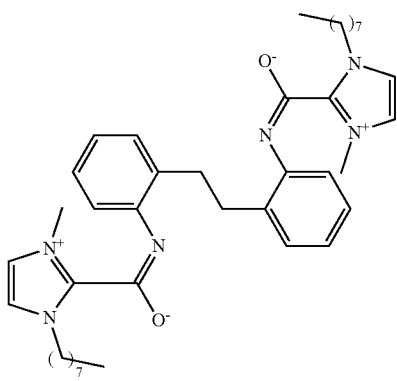
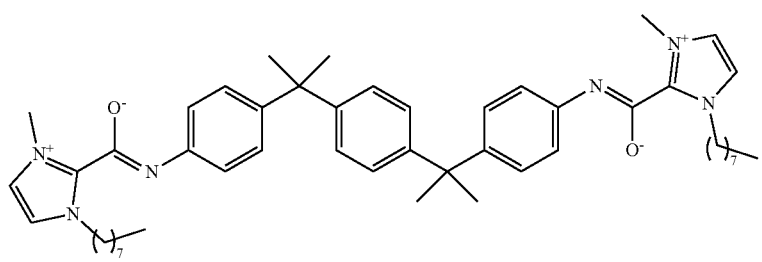
(1b-2-51c)
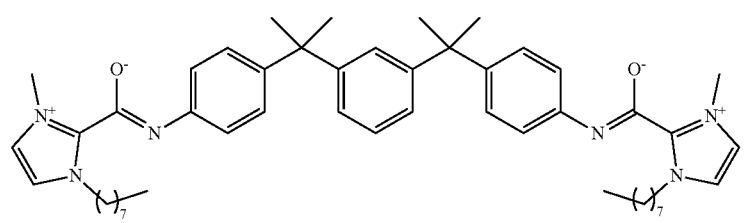
(1b-2-52c)

-continued
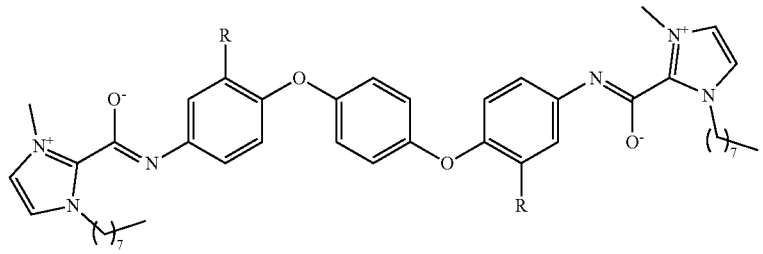
R = H (1b-2-53c)
CF₃ (1b-2-54c)
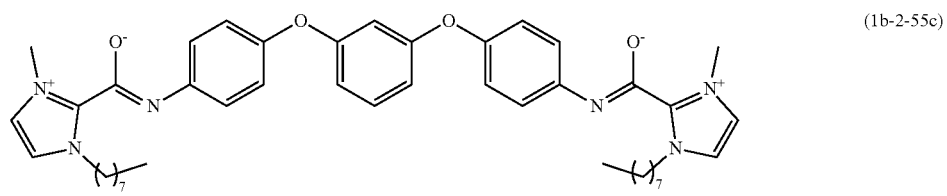
(1b-2-55c)
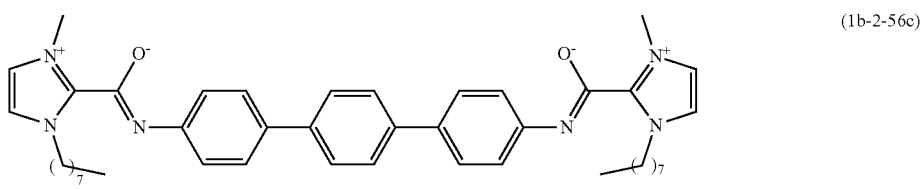
(1b-2-56c)
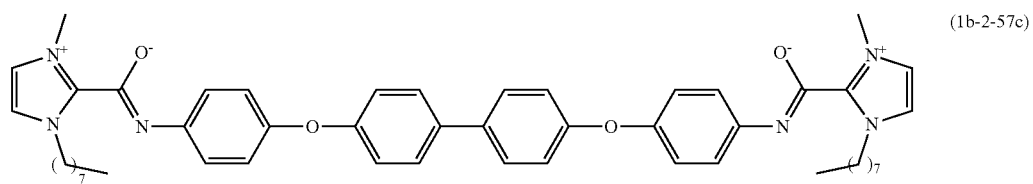
(1b-2-57c)
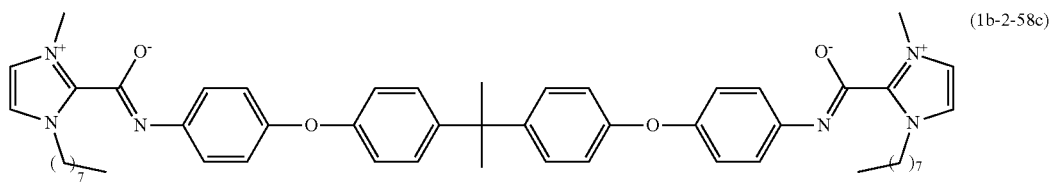
(1b-2-58c)
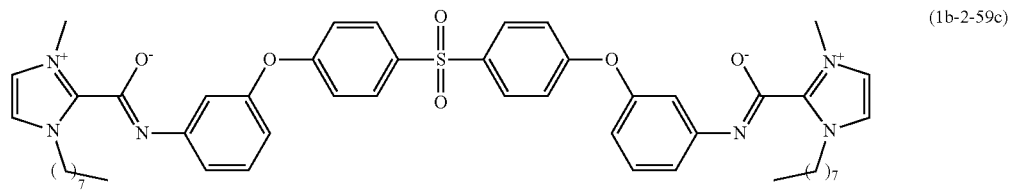
(1b-2-59c)
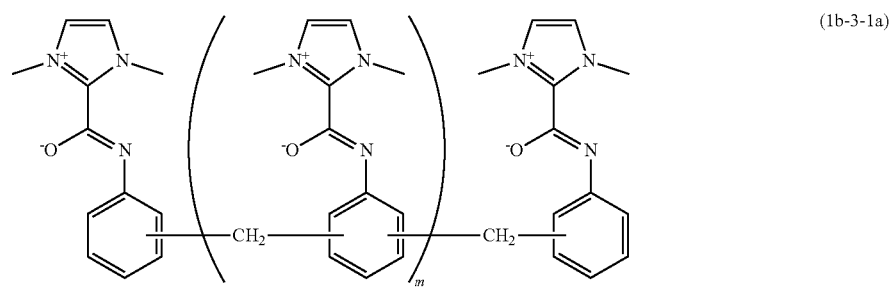
(1b-3-1a)

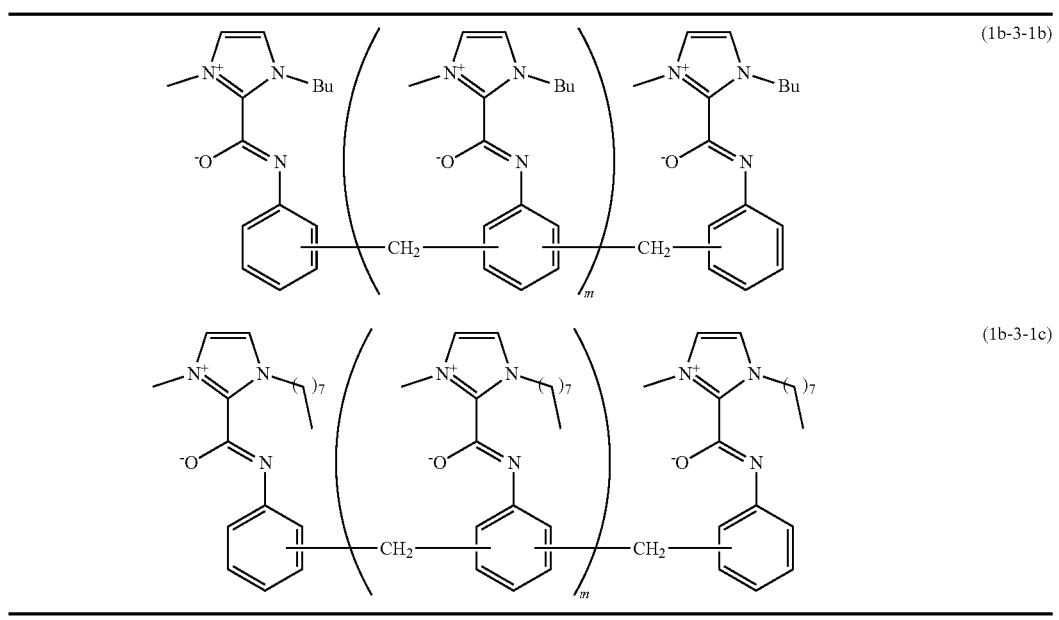
In Formulas (1b-3-1a) to (1b-3-1c), m is an integer of 0 to 4.
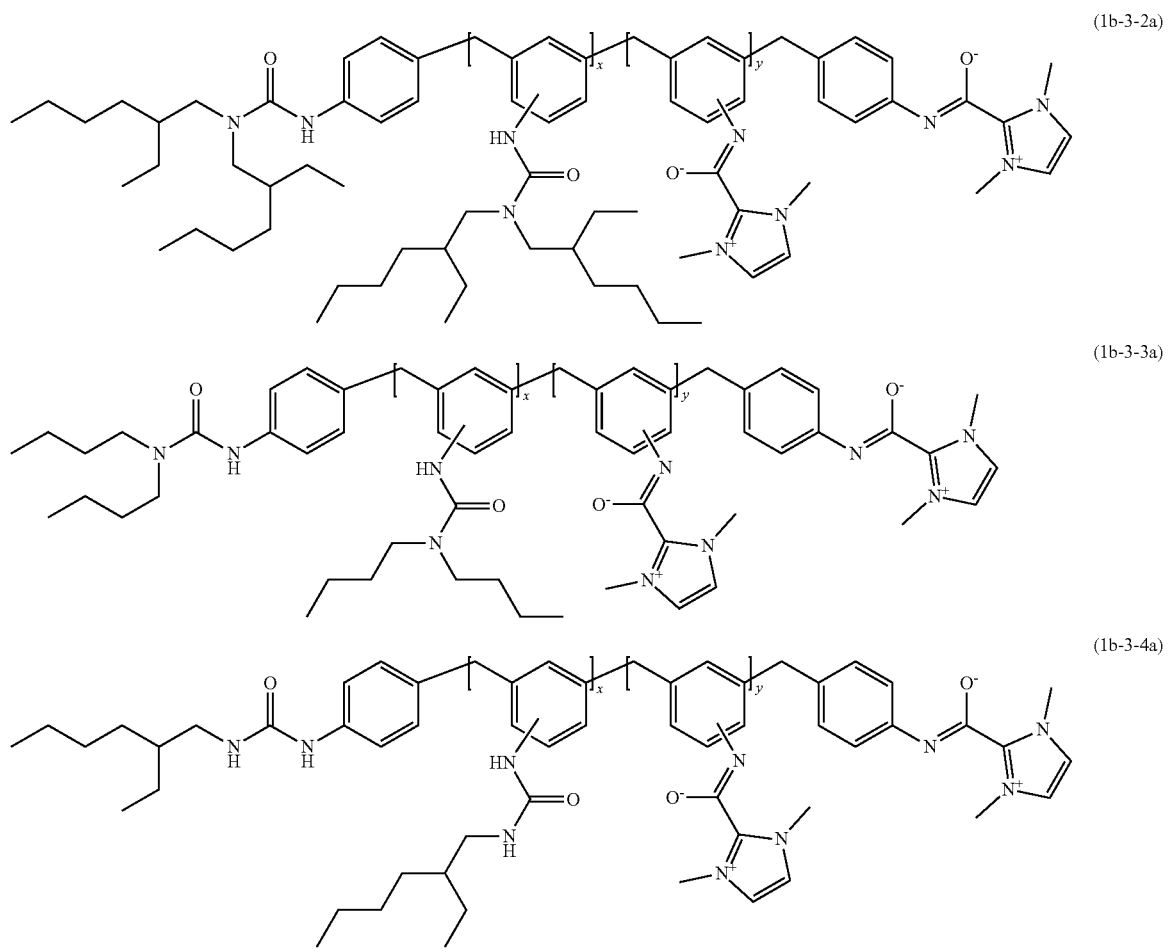

-continued (1b-3-5a)
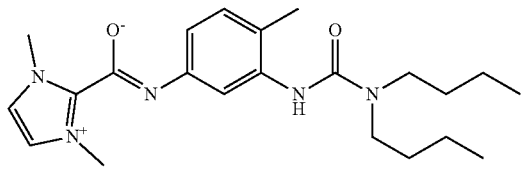

(1b-3-6a)
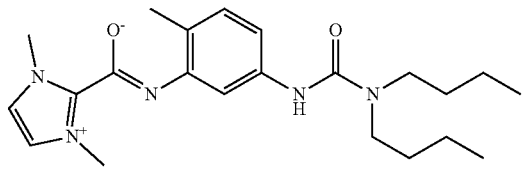

(1b-3-7a)
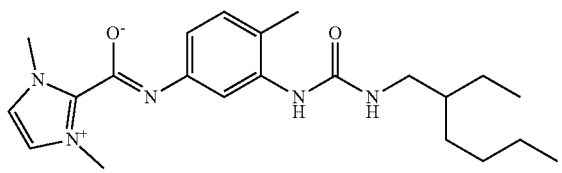

(1b-3-8a)
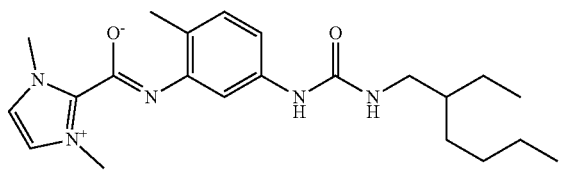

In Formulas (1b-3-2a) to (1b-3-4a), x and y are each 0 or an integer of 1 or more.

Preferable examples of the nitrogen-containing compound (1b) include compounds represented by Formulas (1b-1-5a), (1b-1-17a), (1b-1-27a), (1b-1-38a), (1b-1-40a), (1b-1-42a), (1b-1-43a), (1b-1-45a), (1b-1-49a), (1b-1-56a), (1b-1-85a), (1b-1-86a), (1b-1-87a), (1b-1-5b), (1b-1-17b), (1b-1-27b), (1b-1-38b), (1b-1-40b), (1b-1-42b), (1b-1-43b), (1b-1-45b), (1b-1-49b), (1b-1-56b), (1b-1-85b), (1b-1-86b), (1b-1-87b), (1b-1-5c), (1b-1-17c), (1b-1-27c), (1b-1-38c), (1b-1-40c), (1b-1-42c), (1b-1-43c), (1b-1-45c), (1b-1-49c), (1b-1-56c), (1b-1-85c), (1b-1-86c), (1b-1-87c), (1b-2-18a), (1b-2-19a), (1b-2-24a), (1b-2-47a), (1b-2-52a), (1b-2-55a), (1b-2-18b), (1b-2-19b), (1b-2-24b), (1b-2-47b), (1b-2-52b), (1b-2-55b), (1b-2-18c), (1b-2-19c), (1b-2-24c), (1b-2-47c), (1b-2-52c), (1b-2-55c), (1b-3-2a) (1b-3-3a), (1b-3-4a), (1b-3-5a), (1b-3-6a), (1b-3-7a), and (1b-3-8a); and particularly preferably compounds represented by Formulas (1b-1-17a), (1b-1-27a), (1b-1-38a), (1b-1-43a), (1b-1-49a), (1b-1-56a), (1b-1-17b), (1b-1-17c), (1b-2-24a), (1b-2-47a), (1b-2-52a), (1b-2-55a), and (1b-2-24c).

When the nitrogen-containing compound (1) of the present invention is an isomer, such as an enantiomer, a stereoisomer, or a regioisomer, the nitrogen-containing compound (1) of the present invention includes a mixture of any isomers, unless the isomer is specified. For example, when the nitrogen-containing compound (1) is an enantiomer, the nitrogen-containing compound (1) of the present invention also includes enantiomers divided from the racemic form. These isomers can be obtained as single compounds by conventionally known separation methods (concentration, solvent extraction, column chromatography, recrystallization, etc.).

Moreover, the nitrogen-containing compound (1) is considered to be isomerized by resonance. For example, the compound represented by Formula (1b) wherein X is a nitrogen atom is considered to have the following resonance structure:

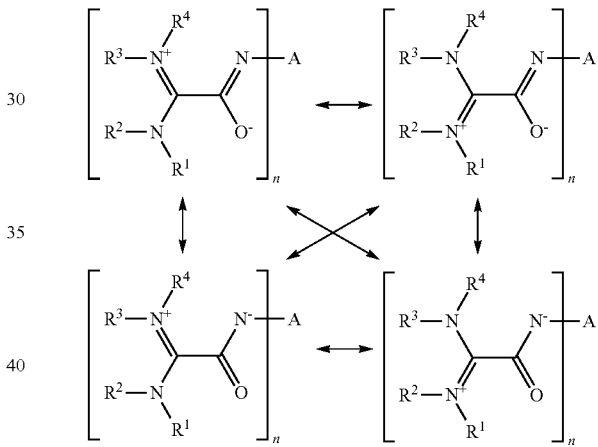

wherein A, $R^1$, $R^2$, $R^3$, $R^4$, and n are as defined above.

The nitrogen-containing compound (1) may be a commercially available product. As the nitrogen-containing compound (1), for example, one produced by the method described below can be used.

The method for producing the nitrogen-containing compound represented by Formula (1a) is not particularly limited. Examples include the method of reacting a nitrogen-containing organic compound with dialkyl carbonate described in Chemical Communications (Cambridge, United Kingdom), 2003, No. 1, pp. 28-29; the method of reacting N-heterocyclic carbene with carbon dioxide described in Chemical Communications (Cambridge, United Kingdom), 2004, No. 1, pp. 112-113; and the like. The method of reacting a nitrogen-containing organic compound with dialkyl carbonate is explained below.

A nitrogen-containing organic compound represented by the following Formula (3) (hereinafter referred to as the nitrogen-containing organic compound (3)) can be reacted with dialkyl carbonate (4) (hereinafter referred to as the dialkyl carbonate (4)) to thereby produce a nitrogen-containing compound represented by Formula (1a) (hereinafter referred to as (Reaction 1)).

Formula (3)

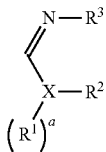

(3)

wherein $R^1$, $R^2$, $R^3$, X, and a are as defined above.

Formula (4)

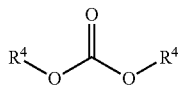

(4)

wherein $R^4$ is as defined above.

In the present invention, in terms of ease of acquisition, $R^2$ and $R^3$ in Formula (3) are preferably bonded together to form a ring structure. The nitrogen-containing organic compound (3) wherein a ring is formed is preferably a nitrogen-containing organic compound represented by the following Formula (3-1), (3-2), or (3-3); and particularly preferably a nitrogen-containing organic compound represented by Formula (3-1).

Formula (3-1)

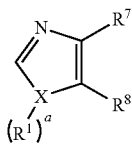

(3-1)

wherein $R^1$, $R^7$, $R^8$, X, and a are as defined above.

Formula (3-2)

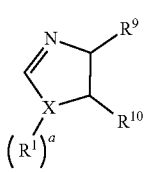

(3-2)

wherein $R^1$, $R^9$, $R^{10}$, X, and a are as defined above.

Formula (3-3)

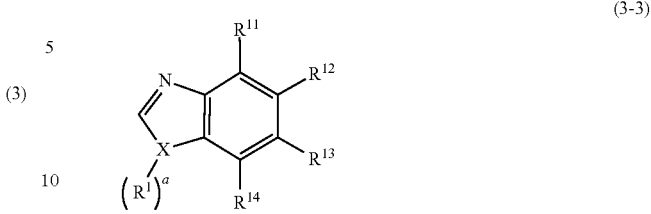

(3-3)

wherein $R^1$, $R^{11}$, $R^{12}$, $R^{13}$, $R^{14}$, X, and a are as defined above.

In Formula (3-1), $R^1$, $R^7$, $R^8$, X, and a are as defined above. Specific examples of the nitrogen-containing organic compound represented by Formula (3-1) include 1-methylimidazole, 1-ethylimidazole, 1-propylimidazole, 1-isopropylimidazole, 1-butylimidazole, 1-tert-butylimidazole, 1-hexylimidazole, 1-octylimidazole, 1-(2-ethylhexyl)imidazole, 1-dodecylimidazole, 1-allylimidazole, 1-benzylimidazole, 1-phenylimidazole, 1-(2,6-diisopropylphenyl)imidazole, 1-mesitylimidazole, 1,4,5-trimethylimidazole,
oxazole, 5-methyloxazole, 4,5-dimethyloxazole,
thiazole, 4-methylthiazole, 5-methylthiazole, 4,5-dimethylthiazole, and the like; preferably 1-methylimidazole, 1-ethylimidazole, 1-propylimidazole, 1-butylimidazole, and 1-octylimidazole; and particularly preferably 1-methylimidazole, 1-butylimidazole, and 1-octylimidazole.

In Formula (3-2), $R^1$, $R^9$, $R^{10}$, X, and a are as defined above. Specific examples of the nitrogen-containing organic compound represented by Formula (3-2) include 1-methylimidazoline, 1-ethylimidazoline, 1-propylimidazoline, 1-isopropylimidazoline, 1-butylimidazoline, 1-tert-butylimidazoline, 1-hexylimidazoline, 1-octylimidazoline, 1-(2-ethylhexyl)imidazoline, 1-dodecylimidazoline, 1-allylimidazoline, 1-benzylimidazoline, 1-phenylimidazoline, 1,4,5-trimethylimidazoline,
oxazoline, 5-methyloxazoline, 4,5-dimethyloxazoline,
thiazoline, 4-methylthiazoline, 5-methylthiazoline, 4,5-dimethylthiazoline, and the like; preferably 1-methylimidazoline, 1-ethylimidazoline, 1-propylimidazoline, and 1-butylimidazoline; and particularly preferably 1-methylimidazoline.

In Formula (3-3), $R^1$, $R^{11}$, $R^{12}$, $R^{13}$, $R^{14}$, X, and a are as defined above. Specific examples of the nitrogen-containing organic compound represented by Formula (3-3) include 1-methylbenzimidazole, 1-ethylbenzimidazole, 1-propylbenzimidazole, 1-isopropylbenzimidazole, 1-butylbenzimidazole, 1-tert-propylbenzimidazole, 1-hexylbenzimidazole, 1-octylbenzimidazole, 1-(2-ethylhexyl)benzimidazole, 1-dodecylbenzimidazole, 1-allylbenzimidazole, 1-benzylbenzimidazole, 1-phenylbenzimidazole, 1,6-dimethylbenzimidazole, 1,6,7-trimethylbenzimidazole,
benzoxazole, benzothiazole, and the like; preferably 1-methylbenzimidazole, 1-ethylbenzimidazole, 1-propylbenzimidazole, and 1-butylbenzimidazole; and particularly preferably 1-methylbenzimidazole.

In Formula (4), $R^4$ is as defined above. Specific examples of the dialkyl carbonate (4) include dimethyl carbonate, diethyl carbonate, dipropyl carbonate, dibutyl carbonate, dipentyl carbonate, dihexyl carbonate, and the like; preferably dimethyl carbonate, diethyl carbonate, dipropyl carbonate, and dibutyl carbonate; and particularly preferably dimethyl carbonate.

In (Reaction 1), the amount of the dialkyl carbonate (4) used is generally 1 mol or more, and preferably 1 to 6 mol, per mol of the nitrogen-containing organic compound (3).

In (Reaction 1), a solvent may or may not be used. When a solvent is used, the solvent used is not particularly limited, as long as it does not affect the reaction. Specific examples of solvents include monovalent alcohol solvents, such as methanol, ethanol, propanol, butanol, pentanol, hexanol, 1-methoxy-2-propanol, and ethoxyethanol; polyol solvents, such as ethylene glycol, propylene glycol, and diethylene glycol; glycol monoalkyl ether solvents, such as dipropylene glycol mono-n-butyl ether, dipropylene glycol monomethyl ether, tripropylene glycol monomethyl ether, propylene glycol mono-n-propyl ether, dipropylene glycol mono-n-propyl ether, propylene glycol mono-n-butyl ether, tripropylene glycol mono-n-butyl ether, propylene glycol monomethyl ether, and diethylene glycol monoethyl ether; and the like. Preferable among these are monovalent alcohol solvents, and particularly preferable is methanol. The amount of solvent used is generally 50 parts by weight or less, and preferably 10 parts by weight or less, per part by weight of the nitrogen-containing organic compound (3).

In (Reaction 1), the reaction temperature can vary depending on the raw materials, solvents, etc., used, and is generally room temperature or higher, and preferably 20 to 200° C. In the present specification, room temperature generally means about 20° C.

In (Reaction 1), the reaction may be performed, if necessary, in an inert gas atmosphere, such as nitrogen, argon, or helium, which do not affect the reaction.

After completion of the reaction, the nitrogen-containing compound (1a) can be isolated by concentrating the reaction mixture, and removing the solvent. The reaction mixture containing the nitrogen-containing compound (1a) can also be directly used as the blocking agent dissociation catalyst (A). When an unreacted nitrogen-containing organic compound (3) and dialkyl carbonate (4) remain in the reaction mixture, they can also be removed by concentrating the reaction mixture. Moreover, when the nitrogen-containing compound (1a) is used as a raw material in the production of a nitrogen-containing compound (1b) described below, the reaction mixture can be directly used as a raw material without removing the nitrogen-containing compound (1a) from the reaction mixture. The concentration step is not required, and the production process is more simplified; thus, it is advantageous for industrial production. Accordingly, when the nitrogen-containing compound (1a) is used as a raw material in the production of a nitrogen-containing compound (1b) described below, it is preferable to use the reaction mixture as it is in the production of a nitrogen-containing compound (1b).

The nitrogen-containing compound represented by Formula (1b) can be produced, for example, by the following (Reaction 2a) or (Reaction 2b).

(Reaction 2a): An isocyanate compound represented by Formula (5) (hereinafter referred to as the isocyanate compound (5)) is reacted with the nitrogen-containing compound represented by Formula (1a) to produce a nitrogen-containing compound represented by Formula (1b).

Formula (5)

$$A\text{—}[NCO]_n \tag{5}$$

wherein A and n are as defined above.

(Reaction 2b): A urethane compound represented by Formula (6) (hereinafter referred to as the urethane compound (6)) is reacted with the nitrogen-containing compound represented by Formula (1a) to produce a nitrogen-containing compound represented by Formula (1b).

Formula (6)

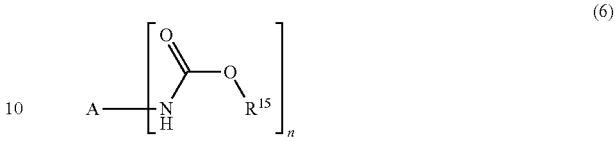

wherein $R^{15}$ is a hydrocarbon group that may contain a heteroatom, and A and n are as defined above.

(Reaction 2a) is explained.

In Formula (5), A and n are as defined above. The isocyanate compound (5) is preferably an isocyanate compound represented by the following Formula (5-1), (5-2), or (5-3), and particularly preferably an isocyanate compound represented by Formula (5-1) or (5-2).

Formula (5-1)

$$R^5\text{—NCO} \tag{5-1}$$

wherein $R^5$ is as defined above.

Formula (5-2)

$$OCN\text{—}R^6\text{—}NCO \tag{5-2}$$

wherein $R^6$ is as defined above.

Formula (5-3)

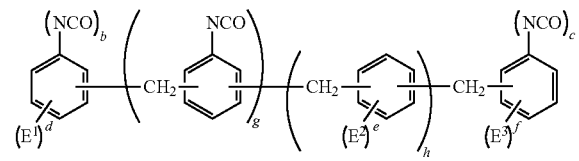

wherein $E^1$, $E^2$, $E^3$, b, c, d, e, f, g, and h are as defined above.

In Formula (5-1), $R^5$ is as defined above.
In Formula (5-2), $R^6$ is as defined above.
In Formula (5-3), $E^1$, $E^2$, $E^3$, b, c, d, e, f, g, and h are as defined above.

In the present invention, a polymer, such as polymethylene polyphenyl polyisocyanate (polymeric MDI), can also be used as the isocyanate compound (5).

When a compound represented by Formula (5-1) or (5-2), wherein $R^5$ or $R^6$ is a hydrocarbon group having an (alkylamino)carbonylamino group or a (dialkylamino)carbonylamino group is used as the isocyanate compound (5), for example, some of the isocyanate groups in the isocyanate compound having a plurality of isocyanate groups represented by Formula (5-2) or (5-3) are reacted with a primary amine compound, a secondary amine compound, or the like to form an (alkylamino)carbonylamino group or a (dialkylamino)carbonylamino group, which can be used as the isocyanate compound (5).

In Formula (5-3), when $E^1$, $E^2$, and $E^3$ are each an (alkylamino)carbonylamino group or a (dialkylamino)carbonylamino group, for example, some of the isocyanate groups in the polymer, such as polymethylene polyphenyl polyisocyanate, are reacted with a primary amine compound or a secondary amine compound to form an (alkylamino) carbonylamino group or a (dialkylamino)carbonylamino group, which can be used as the isocyanate compound (5).

Examples of primary amine compounds include methylamine, ethylamine, propylamine, isopropylamine, n-butylamine, s-butylamine, t-butylamine, n-pentylamine, n-hexylamine, n-octylamine, n-decylamine, n-dodecylamine, 2-ethylhexylamine, and the like; and preferably n-butylamine and 2-ethylhexylamine. Examples of secondary amine compounds include dimethylamine, diethylamine, dipropylamine, diisopropylamine, di(n-butyl)amine, di(s-butyl)amine, di(t-butyl)amine, di(n-pentyl)amine, di(n-hexyl)amine, di(n-octyl)amine, di(n-decyl)amine, methylethylamine, di(n-dodecyl)amine, di(2-ethylhexyl)amine, and the like; and preferably di(n-butyl)amine and di(2-ethylhexyl)amine.

Specific examples of the isocyanate compound (5) are shown below. However, the present invention is not limited thereto. In the following specific examples, Et represents an ethyl group, Pr represents an n-propyl group, and Bu represents an n-butyl group.

$$R-NCO$$

R= $CH_2$ (5-1-1)
$CH_2CH_3$ (5-1-2)
$(CH_2)_2CH_3$ (5-1-3)
$CH(CH_3)_2$ (5-1-4)
$(CH_2)_3CH_3$ (5-1-5)
$C(CH_3)_3$ (5-1-6)
$(CH_2)_4CH_3$ (5-1-7)
$(CH_2)_5CH_3$ (5-1-8)
$(CH_2)_7CH_3$ (5-1-9)
$(CH_2)_{11}CH_3$ (5-1-10)
$(CH_2)_{17}CH_3$ (5-1-11)

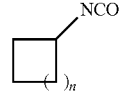

n = 0 (5-1-12)
2 (5-1-13)
3 (5-1-14)

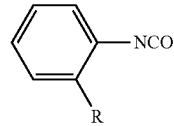

R = H (5-1-15)
$CH_2$ (5-1-16)
$(CH_2)_3CH_3$ (5-1-17)
$(CH_2)_7CH_3$ (5-1-18)
$OCH_3$ (5-1-19)
F (5-1-20)
Cl (5-1-21)
Br (5-1-22)

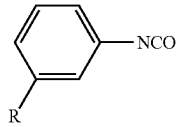

R = $CH_3$ (5-1-23)
$(CH_2)_3CH_3$ (5-1-24)
$(CH_2)_7CH_3$ (5-1-25)
$OCH_3$ (5-1-26)
F (5-1-27)
Cl (5-1-28)
Br (5-1-29)

-continued
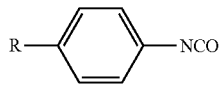
R = CH₃ (5-1-30)
(CH₂)₃CH₃ (5-1-31)
(CH₂)₇CH₃ (5-1-32)
OCH₃ (5-1-33)
CH(CH₃)₂ (5-1-34)
C(CH₃)₃ (5-1-35)
N(CH₃)₂ (5-1-36)
F (5-1-37)
Cl (5-1-38)
Br (5-1-39)
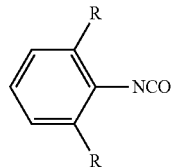
R = CH₃ (5-1-40)
(CH₂)₃CH₃ (5-1-41)
(CH₂)₇CH₃ (5-1-42)
CH(CH₃)₂ (5-1-43)
C(CH₂)₃ (5-1-44)
F (5-1-45)
Cl (5-1-46)
Br (5-1-47)
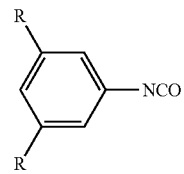
R = CH₃ (5-1-48)
(CH₂)₃CH₃ (5-1-49)
(CH₂)₇CH₃ (5-1-50)
CH(CH₃)₂ (5-1-51)
C(CH₃)₃ (5-1-52)
F (5-1-53)
Cl (5-1-54)
Br (5-1-55)
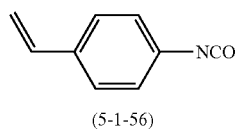
(5-1-56)
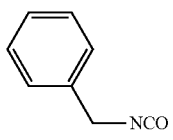
(5-1-57)

-continued
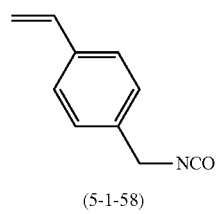
(5-1-58)
OCN—R—NCO
R= —CH$_2$CH$_2$— (5-2-1)
—CH$_2$(CH$_2$)$_2$CH$_3$— (5-2-2)
—CH$_2$(CH$_2$)$_4$CH$_2$— (5-2-3)
—CH$_2$(CH$_2$)$_5$CH$_2$— (5-2-4)
—CH$_2$(CH$_2$)$_8$CH$_3$— (5-2-5)
—CH$_2$(CH$_2$)$_{10}$CH$_3$— (5-2-6)
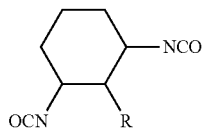
R = H (5-2-7)
CH$_3$ (5-2-8)
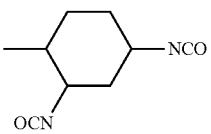
(5-2-9)
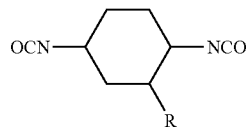
R = H (5-2-10)
CH$_3$ (5-2-11)
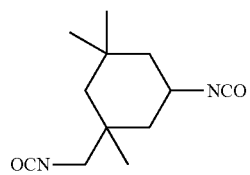
(5-2-12)
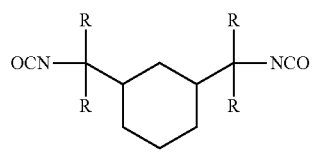
R = H (5-2-13)
CH$_3$ (5-2-14)

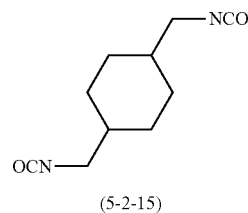
(5-2-15)
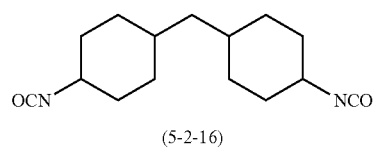
(5-2-16)
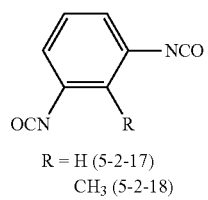
R = H (5-2-17)
CH₃ (5-2-18)
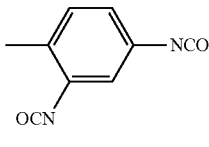
(5-2-19)
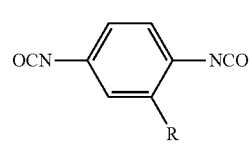
R = H (5-2-20)
CH₃ (5-2-21)
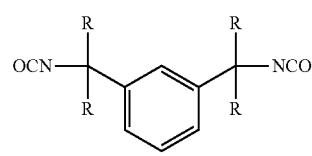
R = H (5-2-22)
CH₃ (5-2-23)
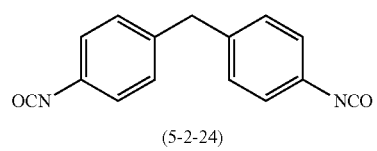
(5-2-24)

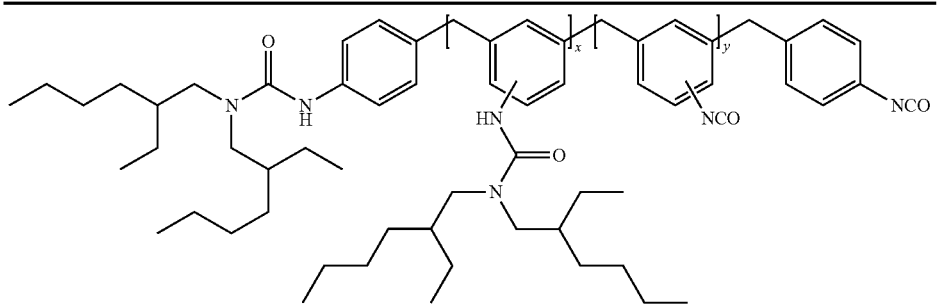
(5-3-2a)
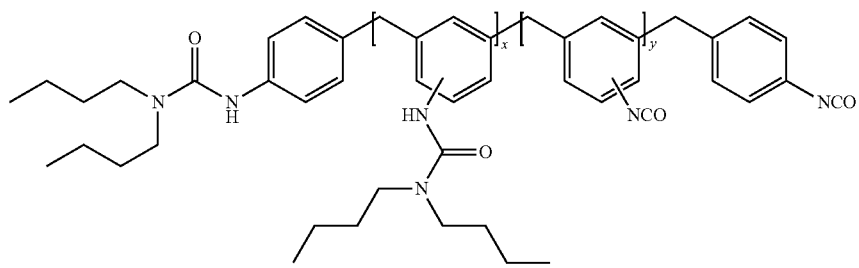
(5-3-3a)
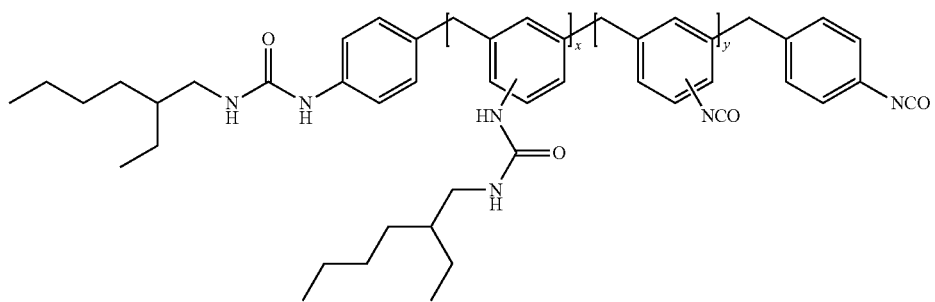
(5-3-4a)
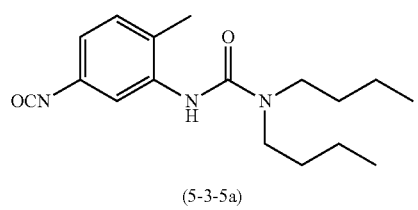
(5-3-5a)
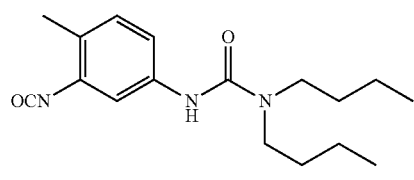
(5-3-6a)
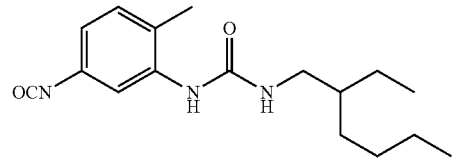
(5-3-7a)

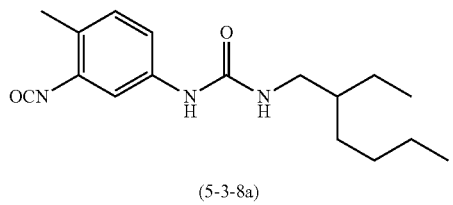

(5-3-8a)

The isocyanate compound (5) is preferably a compound represented by Formula (5-1-5), (5-1-15), (5-1-38), or (5-2-19); and particularly preferably a compound represented by Formula (5-1-15) or (5-1-38).

The isocyanate compounds (5) may be used singly or as a mixture of two or more.

In (Reaction 2a), the amount of the nitrogen-containing compound (1a) used is generally 0.8 mol or more, and preferably 1 to 3 mol, per mol of isocyanate groups contained in the isocyanate compound (5).

In (Reaction 2a), a solvent may or may not be used. When a solvent is used, hydrocarbon solvents are preferably used. Examples of hydrocarbon solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated aliphatic hydrocarbon solvents, such as dichloromethane and chloroform; halogenated aromatic hydrocarbon solvents, such as chlorobenzene and dichlorobenzene; and the like. Preferable among these are aromatic hydrocarbon solvents and halogenated aromatic hydrocarbon solvents; and particularly preferable are toluene, xylene, and chlorobenzene. The solvents can be used as a mixture of two or more, if necessary.

In (Reaction 2a), when a reaction mixture obtained by the reaction of a nitrogen-containing organic compound (3) and dialkyl carbonate (4) is used as the nitrogen-containing compound (1a), the solvent in the reaction mixture can be directly used as a solvent for the reaction of the isocyanate compound (5) and the nitrogen-containing compound (1a). In this case, the reaction may be performed while adding a solvent, if necessary.

In (Reaction 2a), when a solvent is used, the amount of solvent used is generally 50 parts by weight or less, and preferably 0.1 parts by weight or more and 35 parts by weight or less, per part by weight of the nitrogen-containing compound (1a).

In (Reaction 2a), the reaction temperature is not particularly limited, and may be equal to or less than the boiling point of the solvent. The reaction temperature is generally 10° C. or more, preferably 40 to 200° C., and particularly preferably 80 to 150° C.

In (Reaction 2a), the reaction may be performed, if necessary, in an inert gas atmosphere, such as nitrogen, argon, or helium, which do not affect the reaction.

After completion of the reaction, the solvent can be removed by concentration or filtration of the reaction mixture to thereby obtain a nitrogen-containing compound (1b). Moreover, the obtained nitrogen-containing compound (1b) can be purified by a method, such as recrystallization.

(Reaction 2b) is explained.

In Formula (6), A and n are as defined above. $R^{15}$ is a hydrocarbon group that may contain a heteroatom, preferably a $C_1$-$C_{50}$ hydrocarbon group that may contain a heteroatom, more preferably a $C_1$-$C_{30}$ hydrocarbon group that may contain a heteroatom, and particularly preferably a $C_1$-$C_8$ hydrocarbon group that may contain a heteroatom. Examples of the hydrocarbon group that may contain a heteroatom include methyl, ethyl, propyl, isopropyl, n-butyl, s-butyl, t-butyl, n-pentyl, n-hexyl, n-octyl, n-decyl, n-dodecyl, allyl, benzyl, cyclohexyl, adamantyl, phenyl, 2,6-diisopropylphenyl, 2,4,6-trimethylphenyl, 2-methoxyethyl, 2-ethoxyethyl, 2-(dimethylamino)ethyl, and the like; preferably methyl, ethyl, propyl, isopropyl, t-butyl, n-octyl, cyclopentyl, cyclohexyl, and 2,4,6-trimethylphenyl; more preferably methyl, ethyl, isopropyl, t-butyl, n-octyl, and phenyl; and particularly preferably methyl, isopropyl, t-butyl, n-octyl, and phenyl.

In the present invention, the urethane compound represented by Formula (6) (hereinafter referred to as the urethane compound (6)) is preferably a urethane compound represented by the following Formula (6-1), (6-2), or (6-3), and particularly preferably a urethane compound represented by Formula (6-1) or (6-2).

Formula (6-1)

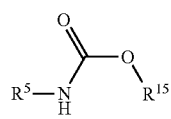

(6-1)

wherein $R^5$ and $R^{15}$ are as defined above.

Formula (6-2)

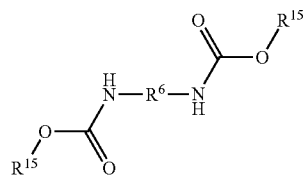

(6-2)

wherein $R^6$ and $R^{15}$ are as defined above.

Formula (6-3)

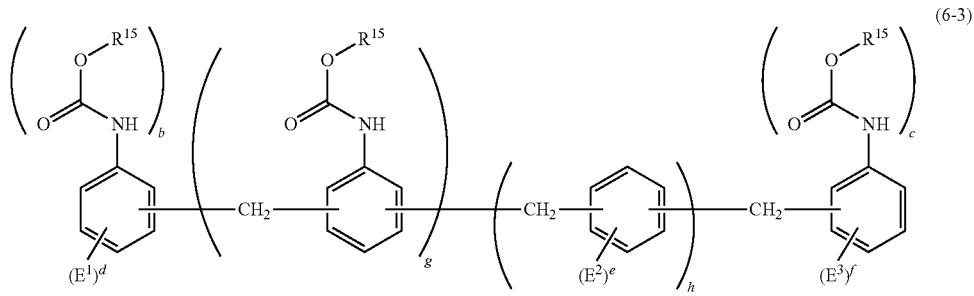

wherein $R^{15}$, $E^1$, $E^2$, $E^3$, b, c, d, e, f, g, and h are as defined above.

In Formula (6-1), $R^5$ and $R^{15}$ are as defined above.
In Formula (6-2), $R^6$ and $R^{15}$ are as defined above.
In Formula (6-3), $R^{15}$, $E^1$, $E^2$, $E^3$, b, c, d, e, f, g, and h are as defined above.

Specific examples of the urethane compound (6) are shown below. However, the present invention is not limited thereto. In the following specific examples, Et represents an ethyl group, Pr represents an n-propyl group, and Bu represents an n-butyl group.

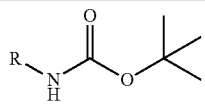

R = CH$_3$ (6-1-1)
CH$_2$CH$_3$ (6-1-2)
(CH$_2$)$_3$CH$_3$ (6-1-3)
CH(CH$_3$)$_2$ (6-1-4)
(CH$_2$)$_3$CH$_3$ (6-1-5)
C(CH$_3$)$_3$ (6-1-6)
(CH$_2$)$_4$CH$_3$ (6-1-7)
(CH$_2$)$_5$CH$_3$ (6-1-8)
(CH$_2$)$_7$CH$_3$ (6-1-9)
(CH$_2$)$_{11}$CH$_3$ (6-1-10)
(CH$_2$)$_{17}$CH$_3$ (6-1-11)

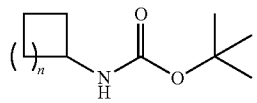

n = 0 (6-1-12)
2 (6-1-13)
3 (6-1-14)

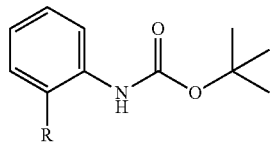

R = H (6-1-15)
CH$_3$ (6-1-16)
(CH$_2$)$_3$CH$_3$ (6-1-17)
(CH$_2$)$_7$CH$_3$ (6-1-18)
OCH$_3$ (6-1-19)
F (6-1-20)
Cl (6-1-21)
Br (6-1-22)

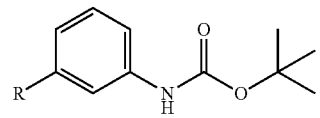
R = CH₃ (6-1-23)
(CH₂)₃CH₃ (6-1-24)
(CH₂)₇CH₃ (6-1-25)
OCH₃ (6-1-26)
F (6-1-27)
Cl (6-1-28)
Br (6-1-29)
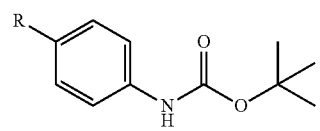
R = CH₃ (6-1-30)
(CH₂)₃CH₃ (6-1-31)
(CH₂)₇CH₃ (6-1-32)
OCH₃ (6-1-33)
CH(CH₃)₂ (6-1-34)
C(CH₃)₂ (6-1-35)
N(CH₃)₂ (6-1-36)
F (6-1-37)
Cl (6-1-38)
Br (6-1-39)
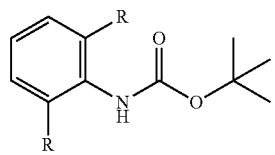
R = CH₃ (6-1-40)
(CH₂)₃CH₃ (6-1-41)
(CH₂)₇CH₃ (6-1-42)
CH(CH₃)₂ (6-1-43)
C(CH₃)₃ (6-1-44)
F (6-1-45)
Cl (6-1-46)
Br (6-1-47)
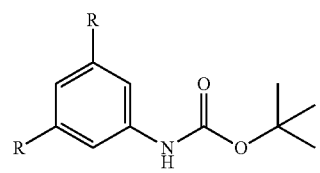
R = CH₃ (6-1-48)
(CH₂)₃CH₃ (6-1-49)
(CH₂)₇CH₃ (6-1-50)
CH(CH₃)₂ (6-1-51)
C(CH₃)₃ (6-1-52)
F (6-1-53)
Cl (6-1-54)
Br (6-1-55)

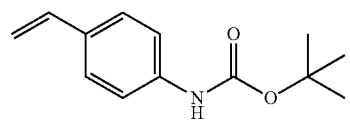
(6-1-56)
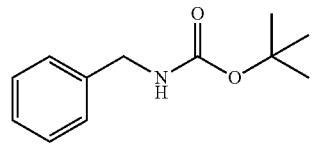
(6-1-57)
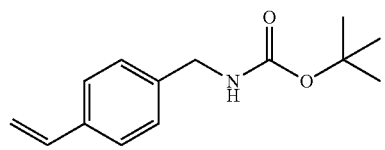
(6-1-58)
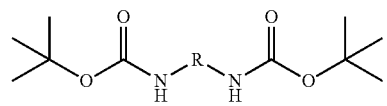
R = —CH$_2$CH$_2$— (6-2-1)
—CH$_2$(CH$_2$)$_2$CH$_3$— (6-2-2)
—CH$_2$(CH$_2$)$_4$CH$_2$— (6-2-3)
—CH$_2$(CH$_2$)$_5$CH$_2$— (6-2-4)
—CH$_2$(CH$_2$)$_6$CH$_2$— (6-2-5)
—CH$_2$(CH$_2$)$_{10}$CH$_2$— (6-2-6)
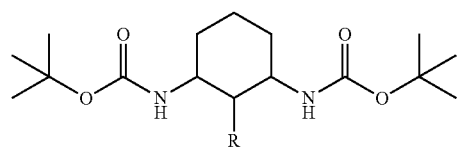
R = H (6-2-7)
CH$_3$ (6-2-8)
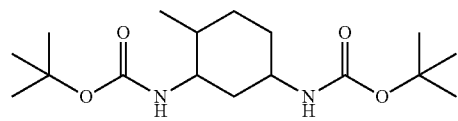
(6-2-9)
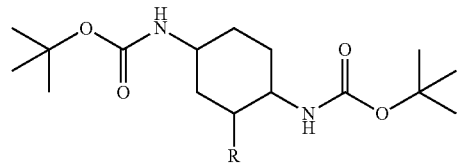
R = H (6-2-10)
CH$_3$ (6-2-11)

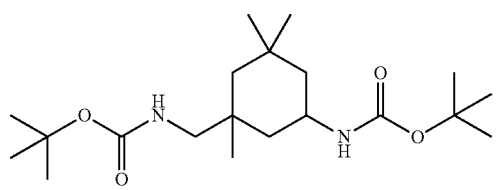
(6-2-12)
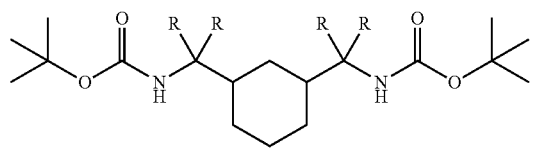
R = H (6-2-13)
CH₃ (6-2-14)
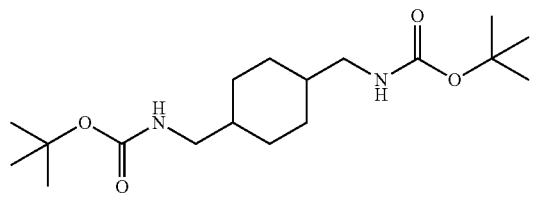
(6-2-15)
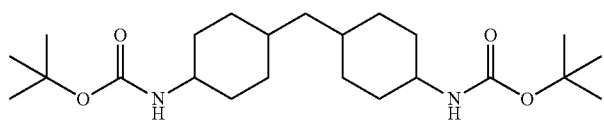
(6-2-16)
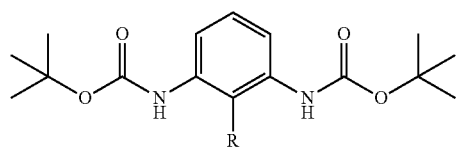
R = H (6-2-17)
CH₃ (6-2-18)
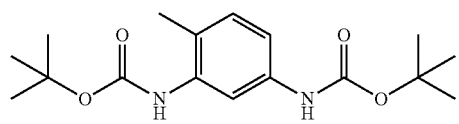
(6-2-19)
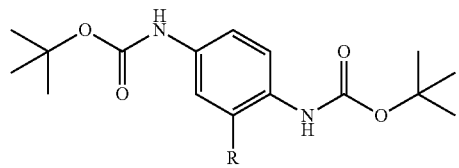
R = H (6-2-20)
CH₃ (6-2-21)

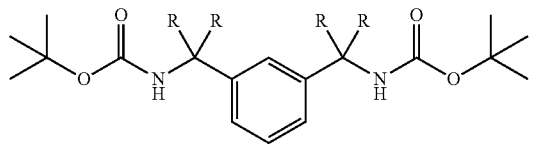
R = H (6-2-22)
CH₃ (6-2-23)
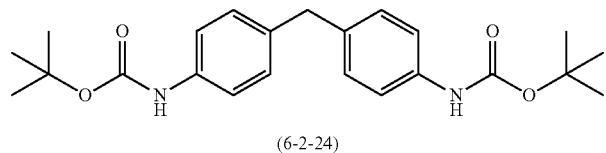 [SMILES: CC(C)(C)OC(=O)Nc1ccc(Cc2ccc(NC(=O)OC(C)(C)C)cc2)cc1]
(6-2-24)
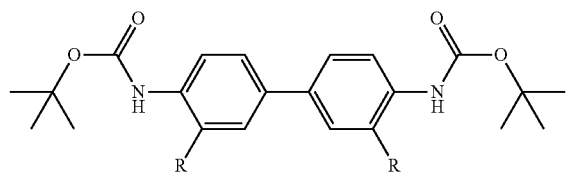
R = CH₃ (6-2-25)
CH₂CH₃ (6-2-26)
OCH₃ (6-2-27)
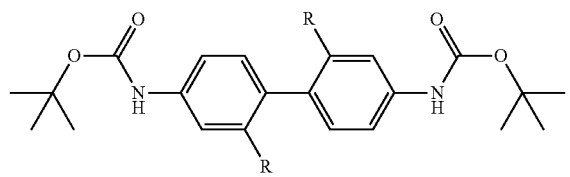
R = CH₃ (6-2-28)
CH₂CH₃ (6-2-29)
OCH₃ (6-2-30)
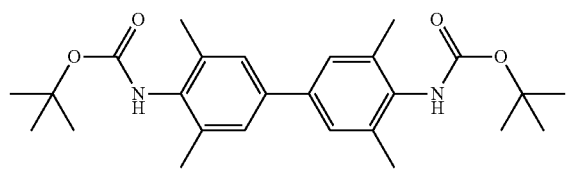
(6-2-31)
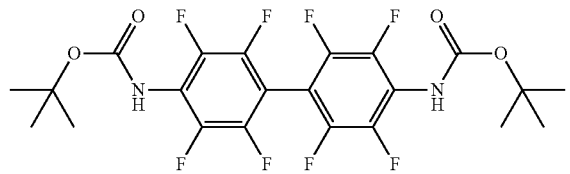
(6-2-32)
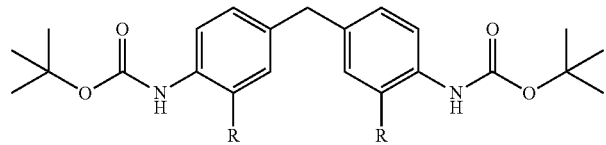
R = CH₃ (6-2-33)
Cl (6-2-34)

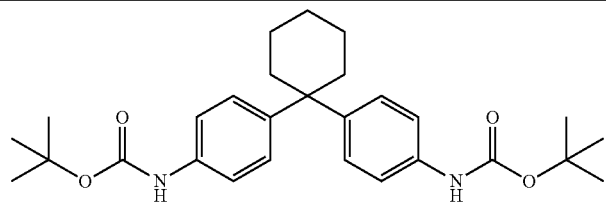
(6-2-35)
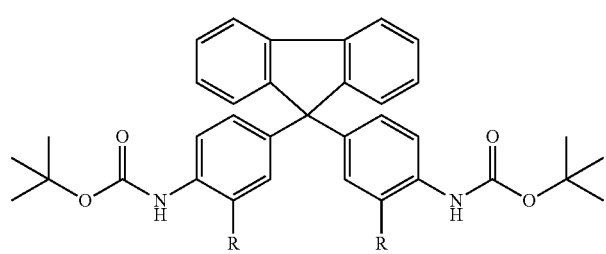
R = H (6-2-36)
CH₃ (6-2-37)
F (6-2-38)
Cl (6-2-39)
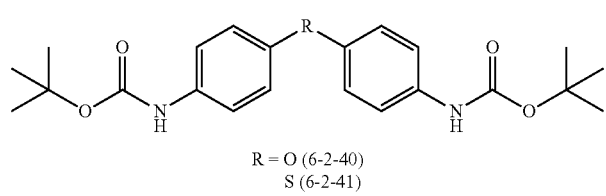
R = O (6-2-40)
S (6-2-41)
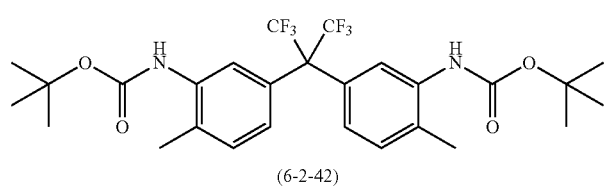 [SMILES: Cc1ccc(C(c2ccc(C)c(NC(=O)OC(C)(C)C)c2)(C(F)(F)F)C(F)(F)F)cc1NC(=O)OC(C)(C)C]
(6-2-42)
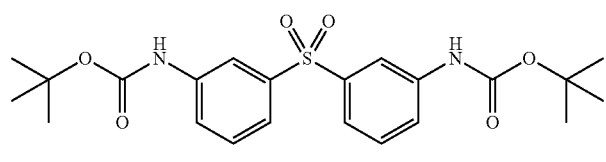
(6-2-43)
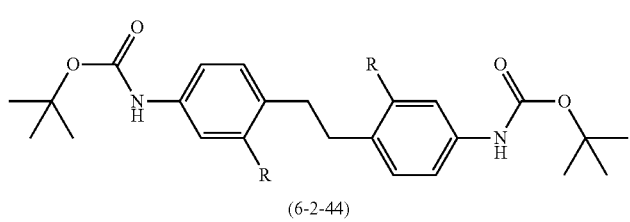
(6-2-44)
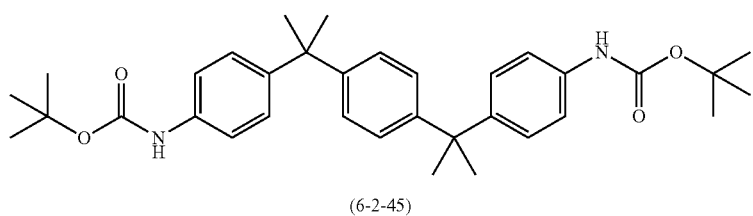 [SMILES: CC(C)(C)OC(=O)Nc1ccc(C(C)(C)c2ccc(C(C)(C)c3ccc(NC(=O)OC(C)(C)C)cc3)cc2)cc1]
(6-2-45)

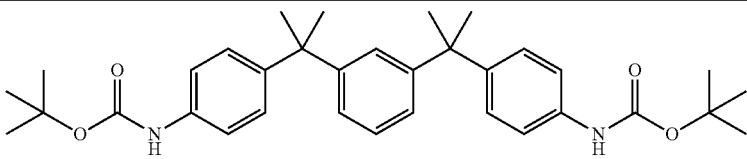

(6-2-46)

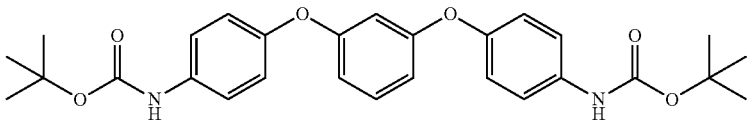

(6-2-47)

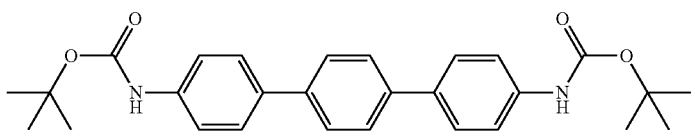

(6-2-48)

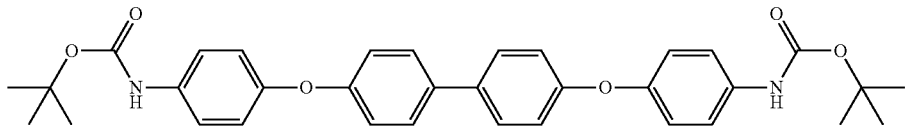

(6-2-49)

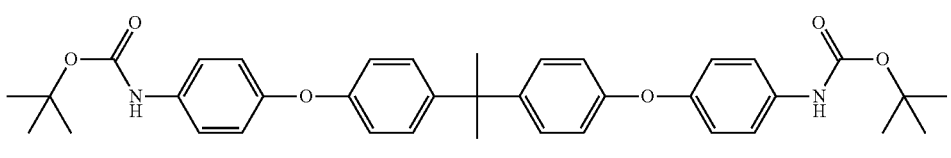

(6-2-50)

The urethane compound (6) is preferably a compound represented by Formula (6-1-21), (6-1-28), (6-1-32), (6-1-33), (6-1-34), (6-1-38), (6-1-43), (6-1-56), (6-1-57), (6-1-58), (6-2-24), (6-2-43), (6-2-46), or (6-2-47).

The urethane compound (6) used as a raw material may be a commercially available product, and can be produced, for example, by (Method I) or (Method II) described below.

(Method I): An amine compound represented by the following Formula (7) (hereinafter referred to as the amine compound (7)) is reacted with a carbonyl compound represented by the following Formula (8) (hereinafter referred to as the carbonyl compound (8)) to produce a urethane compound (6).

Formula (7)

A—[NH$_2$]$_n$ (7)

wherein A and n are as defined above.

Formula (8)

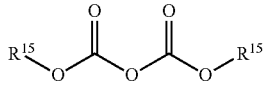

(8)

wherein $R^{15}$ is as defined above.

(Method II): The isocyanate compound (5) is reacted with an alcohol compound represented by the following Formula (9) (hereinafter referred to as the alcohol compound (9)) to produce a urethane compound (6).

Formula (9)

$R^{15}$—OH (9)

wherein $R^{15}$ is as defined above.

As the raw material compounds used in (Method I) and (Method II), known compounds or compounds that can be produced by a known organic synthesis method can be used.

(Method I) is explained.

In Formula (7), A and n are as defined above. The amine compound (7) is preferably an amine compound represented by Formula (7-1), (7-2), or (7-3).

Formula (7-1)

(7-1)

wherein $R^5$ is as defined above.

Formula (7-2)

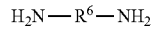
(7-2)

wherein $R^6$ is as defined above.

Formula (7-3)

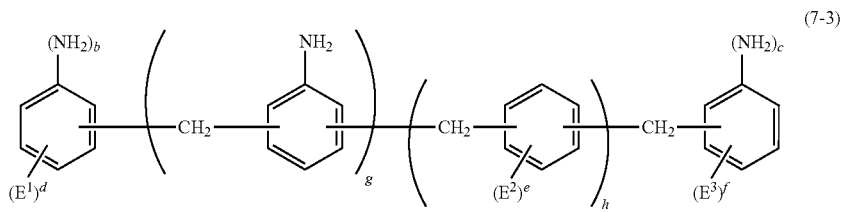
(7-3)

wherein $E^1$, $E^2$, $E^3$, b, c, d, e, f, g, and h are as defined above.
In Formula (7-1), $R^5$ is as defined above.
In Formula (7-2), $R^6$ is as defined above.
In Formula (7-3), $E^1$, $E^2$, $E^3$, b, c, d, e, f, g, and h are as defined above.

Specific examples of the amine compound (7) are described below. However, the present invention is not limited thereto. In the following specific examples, Et represents an ethyl group, Pr represents an n-propyl group, and Bu represents an n-butyl group.

R—NH$_2$
R= CH$_3$ (7-1-1)
CH2CH3 (7-1-2)
(CH2)3CH3 (7-1-3)
CH(CH$_3$)$_2$ (7-1-4)
(CH2)3CH3 (7-1-5)
C(CH$_3$)$_3$ (7-1-6)
(CH$_2$)$_4$CH$_3$ (7-1-7)
(CH$_2$)$_5$CH$_3$ (7-1-8)
(CH$_2$)$_7$CH$_3$ (7-1-9)
(CH$_2$)$_{11}$CH$_3$ (7-1-10)
(CH$_2$)$_{17}$CH$_3$ (7-1-11)

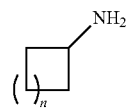

n = 0 (7-1-12)
2 (7-1-13)
3 (7-1-14)

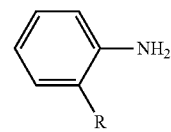

R = H (7-1-15)
CH$_3$ (7-1-16)
(CH$_2$)$_3$CH$_3$ (7-1-17)
(CH$_2$)$_7$CH$_3$ (7-1-18)
OCH$_3$ (7-1-19)
F (7-1-20)
Cl (7-1-21)
Br (7-1-22)

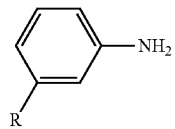
R = CH₃ (7-1-23)
(CH₂)₃CH₃ (7-1-24)
(CH₂)₇CH₃ (7-1-25)
OCH₃ (7-1-26)
F (7-1-27)
Cl (7-1-28)
Br (7-1-29)
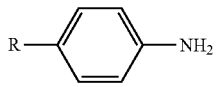
R = CH₃ (7-1-30)
(CH₂)₃CH₃ (7-1-31)
(CH₂)₇CH₃ (7-1-32)
OCH₃ (7-1-33)
CH(CH₃)₂ (7-1-34)
C(CH₃)₃ (7-1-35)
N(CH₃)₂ (7-1-36)
F (7-1-37)
Cl (7-1-38)
Br (7-1-39)
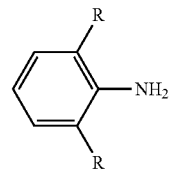
R = CH₃ (7-1-40)
(CH₂)₃CH₃ (7-1-41)
(CH₂)₇CH₃ (7-1-42)
CH(CH₃)₂ (7-1-43)
C(CH₃)₃ (7-1-44)
F (7-1-45)
Cl (7-1-46)
Br (7-1-47)
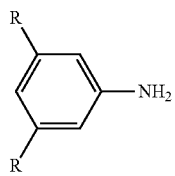
R = CH₃ (7-1-48)
(CH₂)₃CH₃ (7-1-49)
(CH₂)₇CH₃ (7-1-50)
CH(CH₃)₂ (7-1-51)
C(CH₃)₃ (7-1-52)
F (7-1-53)
Cl (7-1-54)
Br (7-1-55)
(7-1-56)

-continued
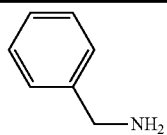
(7-1-57)
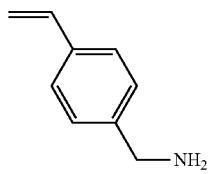
(7-1-58)
$H_2N-R-NH_2$
R= —$CH_2CH_2$— (7-2-1)
—$CH_2(CH_2)_2CH_3$— (7-2-2)
—$CH_2(CH_2)_4CH_2$— (7-2-3)
—$CH_2(CH_2)_5CH_2$— (7-2-4)
—$CH_2(CH_2)_8CH_2$— (7-2-5)
—$CH_2(CH_2)_{10}CH_2$— (7-2-6)
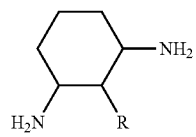
R = H (7-2-7)
$CH_3$ (7-2-8)
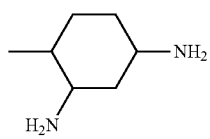
(7-2-9)
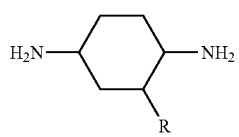
R = H (7-2-10)
$CH_3$ (7-2-11)
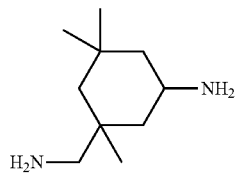
(7-2-12)
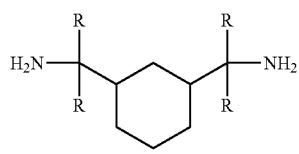
R = H (7-2-13)
$CH_3$ (7-2-14)

-continued
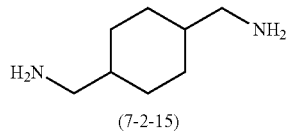
(7-2-15)
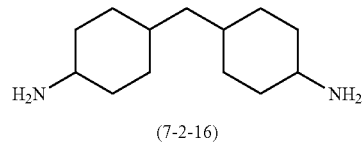 [SMILES: NC1CCC(CC2CCC(N)CC2)CC1]
(7-2-16)
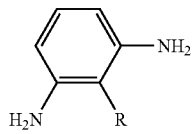
R = H (7-2-17)
CH₃ (7-2-18)
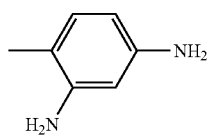
(7-2-19)
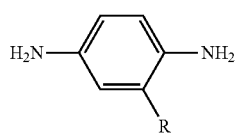
R = H (7-2-20)
CH₃ (7-2-21)
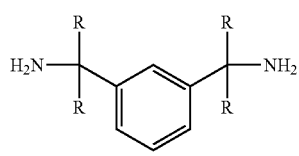
R = H (7-2-22)
CH₃ (7-2-23)
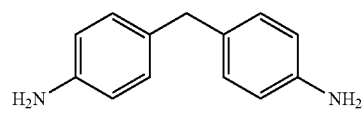
(7-2-24)
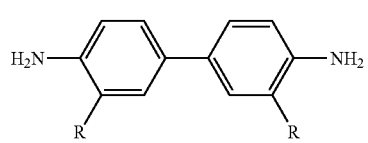
R = CH₃ (7-2-25)
CH₂CH₃ (7-2-26)
OCH₃ (7-2-27)

-continued
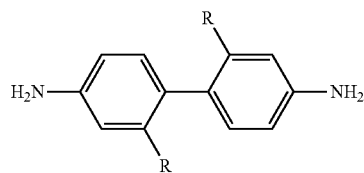
R = CH₃ (7-2-28)
CH₂CH₃ (7-2-29)
OCH₃ (7-2-30)
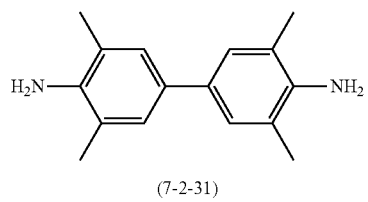 [SMILES: Cc1cc(-c2cc(C)c(N)c(C)c2)cc(C)c1N]
(7-2-31)
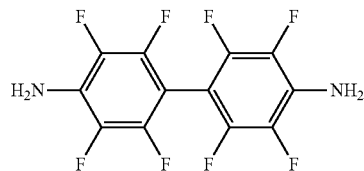
(7-2-32)
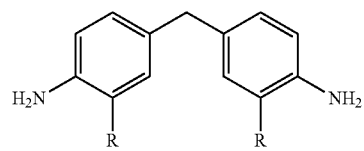
R = CH₃ (7-2-33)
Cl (7-2-34)
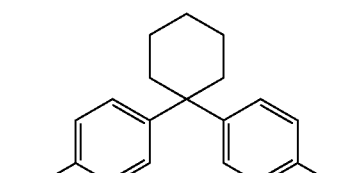
(7-2-35)
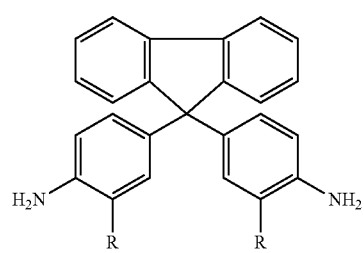
R = H (7-2-36)
CH₃ (7-2-37)
F (7-2-38)
Cl (7-2-39)

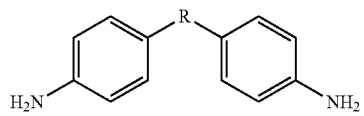
R = O (7-2-40)
S (7-2-41)
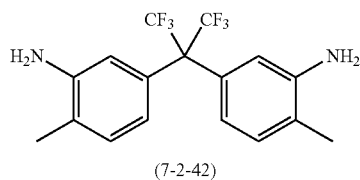 [SMILES: Cc1ccc(C(c2ccc(C)c(N)c2)(C(F)(F)F)C(F)(F)F)cc1N]
(7-2-42)
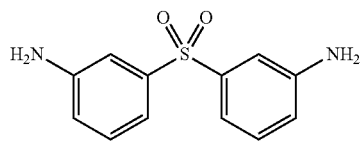
(7-2-43)
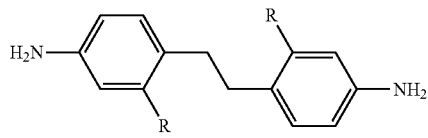
(7-2-44)
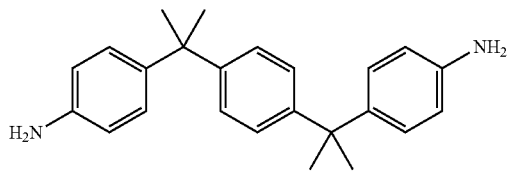
(7-2-45)
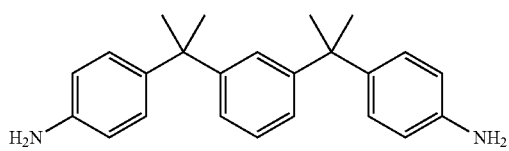
(7-2-46)
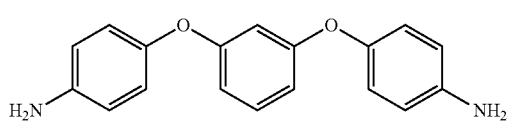
(7-2-47)
(7-2-48)
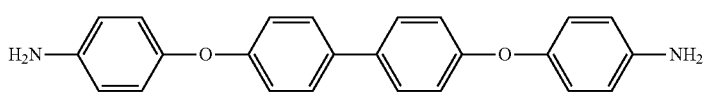
(7-2-49)

-continued

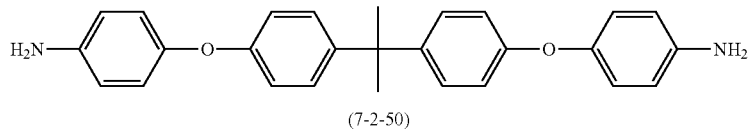 [SMILES: CC(C)(c1ccc(Oc2ccc(N)cc2)cc1)c1ccc(Oc2ccc(N)cc2)cc1]

(7-2-50)

Preferable examples of the amine compound (7) are compounds represented by Formulas (7-1-28), (7-1-32), (7-1-33), (7-1-34), (7-1-38), (7-1-43), (7-1-56), (7-1-57), (7-1-58), (7-2-43), (7-2-46), and (7-2-47).

In Formula (8), $R^{15}$ is as defined above. Examples of the carbonyl compound (8) include di-t-butyl dicarbonate, dibenzyl dicarbonate, di-t-amyl dicarbonate, and diaryl dicarbonate; and preferably di-t-butyl dicarbonate and dibenzyl dicarbonate.

In (Method I), the amount of the carbonyl compound (8) used is generally 1 mol or more, and preferably 1 to 6 mol, per mol of amino groups in the amine compound (7).

In (Method I), a base catalyst may be used, if necessary. Examples of the base catalyst include organic bases, such as triethylamine and dimethylaminopyridine; and inorganic bases, such as potassium hydroxide, sodium hydroxide, and sodium hydrogen carbonate. Triethylamine is preferable.

In (Method I), a solvent may or may not be used. When a solvent is used, the solvent used is not particularly limited, as long as it does not affect the reaction. Specific examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated hydrocarbon solvents, such as dichloromethane and chloroform; ether solvents, such as diethyl ether, tetrahydrofuran, and 1,4-dioxane; alcohol solvents, such as methanol and ethanol; N,N-dimethylformamide, acetonitrile, and the like. Ether solvents and alcohol solvents are preferable, and tetrahydrofuran and methanol are particularly preferable. The amount of solvent used is generally 50 parts by weight or less, and preferably 0.1 to 10 parts by weight, per part by weight of the amine compound (7).

In (Method I), the reaction temperature can vary depending on the raw materials, solvents, etc., used, and is generally room temperature or higher, and preferably 20 to 250° C.

In (Method I), the reaction may be performed, if necessary, in an inert gas atmosphere, such as nitrogen, argon, or helium, which do not affect the reaction.

After completion of the reaction, the urethane compound (6) can be isolated by subjecting the unreacted carbonyl compound (8) to treatment with an amine compound, such as diethanolamine, washing with water or a weak acidic aqueous solution, concentration of the reaction mixture, or the like. If necessary, the urethane compound (6) may be purified by recrystallization etc.

(Method II) is explained.

In Formula (9), $R^{15}$ is as defined above. Examples of alcohol compounds include aliphatic alcohols, such as methanol, ethanol, isopropanol, t-butanol, n-octanol, methoxyethanol, and ethoxyethanol; aromatic alcohols, such as benzyl alcohol; and phenols, such as phenol. Methanol, ethanol, isopropanol, t-butanol, n-octanol, and phenol are preferable.

In (Method II), the amount of the alcohol compound (9) used is generally 1 mol or more, and preferably 1 to 70 mol, per mol of isocyanate groups in the isocyanate compound (5).

In (Method II), the reaction temperature can vary depending on the raw materials, solvents, etc., used, and is generally room temperature or higher, and preferably 20 to 200° C.

In (Method II), a catalyst may be used, if necessary. Examples of catalysts include organometallic compounds containing at least one metal element selected from the group consisting of tin, iron, lead, bismuth, mercury, titanium, hafnium, and zirconium; amine compounds; and the like. Preferable examples of organometallic compounds include tin carboxylate, dialkyltin oxide, and bismuth carboxylate; and more preferably dibutyltin dilaurate. Preferable examples of amine compounds include 1,4-diazabicyclo[2.2.2]octane, N,N,N',N'',N''-pentamethyldiethylenetriamine, and bis(2-dimethylaminoethyl)ether.

In (Method II), a solvent may or may not be used. The alcohol compound (9) can also be used as a solvent by using an excess of the alcohol compound (9). When a solvent is further used, in addition to the alcohol compound (9), the solvent used is not particularly limited, as long as it does not affect the reaction. Specific examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated hydrocarbon solvents, such as dichloromethane and chloroform; ether solvents, such as diethyl ether and tetrahydrofuran; and the like. Toluene is preferable. The amount of solvent used is generally 50 parts by weight or less, and preferably 0.1 to 10 parts by weight, per part by weight of the isocyanate compound (5).

In (Method II), the reaction may be performed, if necessary, in an inert gas atmosphere, such as nitrogen, argon, or helium, which do not affect the reaction.

After completion of the reaction, the urethane compound (6) can be isolated by removing the solvent by concentration or filtration of the reaction mixture. If necessary, the obtained urethane compound (6) can be purified by, for example, washing with any solvent, and then subjected to the reaction with the nitrogen-containing compound (1a).

In (Reaction 2b), the amount of the nitrogen-containing compound (1a) used is generally 0.8 mol or more, and preferably 1 to 3 mol, per mol of carbamate groups contained in the urethane compound (6).

In (Reaction 2b), a solvent may or may not be used. Examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated aliphatic hydrocarbon solvents, such as butyl chloride and 1,2-dichloroethane; halogenated aromatic hydrocarbon solvents, such as chlorobenzene; and the like. Preferable among these are aromatic hydrocarbon solvents and halogenated aromatic hydrocarbon solvents; and particularly preferable are toluene, xylene, and chlorobenzene. The solvents can be used as a mixture of two or more, if necessary.

In (Reaction 2b), when a reaction mixture obtained by the reaction of the nitrogen-containing organic compound (3) and the dialkyl carbonate (4) is used as the nitrogen-containing compound (1a), the solvent in the reaction mixture can also be directly used as a solvent for the reaction of the urethane compound (6) and the nitrogen-containing compound (1a). In this case, the reaction may be performed while adding a solvent, if necessary.

In (Reaction 2b), the amount of solvent used is generally 50 parts by weight or less, preferably 35 parts by weight or less, and more preferably 0.1 to 35 parts by weight, per part by weight of the nitrogen-containing compound (1a).

In (Reaction 2b), the reaction temperature is not particularly limited, and may be equal to or less than the boiling point of the solvent. The reaction temperature is generally 10° C. or more, preferably 40 to 200° C., and particularly preferably 80 to 150° C.

In (Reaction 2b), the reaction may be performed, if necessary, in an inert gas atmosphere, such as nitrogen, argon, or helium, which do not affect the reaction.

After completion of the reaction, the nitrogen-containing compound (1b) can be obtained by removing the solvent by concentration or filtration of the reaction mixture. Moreover, the obtained nitrogen-containing compound (1b) may be purified by a method, such as recrystallization.

The blocking agent dissociation catalyst (A) of the present invention can be used singly as the blocking agent dissociation catalyst (A), or can be used as a mixture of two or more. Further, a solvent or the like can be mixed and used, if necessary.

The solvent is not particularly limited. Examples include hydrocarbon solvents, such as benzene, toluene, xylene, cyclohexane, mineral spirit, and naphtha; ketone solvents, such as acetone, methyl ethyl ketone, and methyl isobutyl ketone; ester solvents, such as ethyl acetate, n-butyl acetate, and cellosolve acetate; alcohol solvents, such as methanol, ethanol, 2-propanol, n-butanol, 2-methoxyethanol, 2-ethoxyethanol, and 2-n-butoxyethanol; polyol solvents, such as ethylene glycol, propylene glycol, diethylene glycol, polyethylene glycol, and glycerol; water; and the like. These solvents may be used singly or in combination of two or more.

The blocking agent dissociation catalyst for blocked isocyanates (A) of the present invention can dissociate a blocking agent from block isocyanates.

The blocking agent dissociation catalyst (A) of the present invention can sufficiently achieve the object of the present invention, as long as it contains the nitrogen-containing compound (1) as an active ingredient. If necessary, the blocking agent dissociation catalyst (A) of the present invention may contain a known blocking agent dissociation catalyst for blocked isocyanates.

Next, the thermosetting composition of the present invention is explained.

The thermosetting composition of the present invention comprises the blocking agent dissociation catalyst (A) of the present invention described above, a blocked isocyanate, and a compound having an isocyanate-reactive group.

Examples of blocked isocyanates include compounds obtained by reacting known polyisocyanates and a known blocking agent so that the isocyanate groups in the polyisocyanates are sealed with the blocking agent. The blocked isocyanates may be used singly or as a mixture of two or more.

In the present invention, the polyisocyanate is not particularly limited, as long as it is a compound having two or more isocyanate groups. Examples of known polyisocyanates include aliphatic polyisocyanates, alicyclic polyisocyanates, aromatic polyisocyanates, aromatic aliphatic polyisocyanates, modified polyisocyanates thereof, and the like. These polyisocyanates may be used singly or as a mixture of two or more.

Examples of aliphatic polyisocyanates include 1,4-tetramethylene diisocyanate, 1,6-hexamethylene diisocyanate, 2,2,4-trimethylhexamethylene diisocyanate, 2,4,4-trimethylhexamethylene diisocyanate, lysine diisocyanate, dimer acid diisocyanate, and the like.

Examples of alicyclic polyisocyanates include 1,3-bis(isocyanatomethyl)cyclohexane, 1,4-bis(isocyanatomethyl)cyclohexane, 3-isocyanatomethyl-3,3,5-trimethylcyclohexane (isophorone diisocyanate), bis-(4-isocyanatocyclohexyl)methane, norbornane diisocyanate, and the like.

Examples of aromatic polyisocyanates include 2,4'-diphenylmethane diisocyanate, 4,4'-diphenylmethane diisocyanate, crude diphenylmethane diisocyanate, 1,4-phenylene diisocyanate, 2,4-tolylene diisocyanate, 2,6-tolylene diisocyanate, 3,3'-dimethyl-4,4'-diisocyanatobiphenyl, 3,3'-dimethyl-4,4'-diisocyanatodiphenylmethane, 1,5-naphthylene diisocyanate, and the like.

Examples of aromatic aliphatic polyisocyanates include 1,3-xylylene diisocyanate, 1,4-xylylene diisocyanate, $\alpha,\alpha,\alpha',\alpha'$-tetramethylxylylene diisocyanate, and the like.

Examples of modified polyisocyanates include isocyanate-terminated compounds obtained by the reaction of the above polyisocyanate compounds with compounds having an active hydrogen group, and reaction products of the polyisocyanate compounds and/or the isocyanate-terminated compounds (e.g., adduct-type polyisocyanates, and modified isocyanates obtained by allophanatization reaction, carbodiimidization reaction, uretodionization reaction, isocyanuration reaction, uretoniminization reaction, biuretization reaction, or the like).

Examples of known blocking agents include alcohols, such as methanol, ethanol, n-propanol, isopropanol, n-butanol, sec-butanol, tert-butanol, 2-ethylhexanol, and butyl cellosolve; phenols, such as phenol, cresol, and 2-hydroxypyridine; amines, such as diisopropylamine; lactams, such as ε-caprolactam, δ-valerolactam, and γ-butyrolactam; oximes, such as formaldehyde oxime, acetaldehyde oxime, acetone oxime, methyl ethyl ketoxime, and methyl isobutyl ketoxime; ketoenols, such as acetylacetone; pyrazoles, such as 1,2-pyrazole and 3,5-dimethylpyrazole; triazoles, such as triazole; and the like. Preferable among these are lactams, oximes, and pyrazoles; and particularly preferable are ε-caprolactam, methyl ethyl ketoxime, and 3,5-dimethylpyrazole.

Examples of the compound having an isocyanate-reactive group include compounds having two or more active hydrogen groups, such as polyols, polyamines, and alkanolamines. These compounds having an isocyanate-reactive group may be a mixture of two or more.

In the present invention, polyols are compounds having two or more hydroxyl groups. Examples of polyols include polyether polyols, polyester polyols, acrylic polyols, polyolefin polyols, fluorine polyols, polycarbonate polyols, polyurethane polyols, and the like. These polyols may be a mixture of two or more.

Examples of polyether polyols include active hydrogen compounds, such as aliphatic amine polyols, aromatic amine polyols, Mannich polyols, polyhydric alcohols, polyhydric phenols, and bisphenols; compounds obtained by adding alkylene oxides to these active hydrogen compounds; and the like. These polyether polyols may be a mixture of two or more.

Examples of aliphatic amine polyols include alkylenediamine-based polyols and alkanolamine-based polyols. These polyol compounds are polyfunctional polyol compounds having terminal hydroxyl groups obtained by the ring-opening addition of at least one cyclic ether, such as ethylene oxide or propylene oxide, using alkylenediamine or alkanolamine as an initiator. As the alkylenediamine, known compounds can be used without limitation. Specifically, $C_2$-$C_8$ alkylenediamines, such as ethylenediamine, propylenediamine, butylenediamine, hexamethylenediamine, and neopentyldiamine, are preferably used. Among these, alkylenediamines having a small number of carbon atoms are more preferably used, and polyol compounds using ethylenediamine or propylenediamine as an initiator are particularly preferably used. Examples of alkanolamines include monoethanolamine, diethanolamine, and triethanolamine. The number of functional groups of a polyol compound using alkylenediamine as an initiator is 4, and the number of functional groups of a polyol compound using alkanolamine as an initiator is 3. The number of functional groups of a mixture thereof is 3 or 4. The hydroxyl value of the aliphatic amine polyol is generally 100 to 1500 mgKOH/g, and preferably 200 to 1200 mgKOH/g. These aliphatic amine polyols may be a mixture of two or more.

Aromatic amine polyols are polyfunctional polyether polyol compounds having terminal hydroxyl groups obtained by the ring-opening addition of at least one cyclic ether, such as ethylene oxide or propylene oxide, using aromatic diamine as an initiator. As the initiator, a known aromatic diamine can be used without limitation. Specific examples include 2,4-toluenediamine, 2,6-toluenediamine, diethyltoluenediamine, 4,4'-diaminodiphenylmethane, p-phenylenediamine, o-phenylenediamine, naphthalenediamine, and the like. Among these, toluenediamine (2,4-toluenediamine, 2,6-toluenediamine, or a mixture thereof) is particularly preferably used. The number of functional groups of the aromatic amine polyol is 4, and the hydroxyl value is generally 100 to 1500 mgKOH/g, and preferably 200 to 1200 mgKOH/g. These aromatic amine polyols may be a mixture of two or more.

Mannich polyols are active hydrogen compounds having a hydroxyl value of 200 to 700 mgKOH/g and 2 to 4 functional groups and obtained by the Mannich reaction of phenol and/or an alkyl-substituted derivative thereof, formaldehyde, and alkanolamine, or polyol compounds having a hydroxyl value of 200 to 700 mgKOH/g and 2 to 4 functional groups and obtained by the ring-opening addition polymerization of the active hydrogen compounds with at least one of ethylene oxide and propylene oxide. These Mannich polyols may be a mixture of two or more.

Examples of polyhydric alcohols include dihydric alcohols (e.g., ethylene glycol, propylene glycol, 1,4-butanediol, 1,6-hexanediol, diethylene glycol, triethylene glycol, dipropylene glycol, and neopentyl glycol), trihydric or higher alcohols (e.g., glycerol, trimethylolpropane, pentaerythritol, methylglucoside, sorbitol, and sucrose), and the like. These polyhydric alcohols may be a mixture of two or more.

Examples of polyhydric phenols include pyrogallol, hydroquinone, and the like. These polyhydric phenols may be a mixture of two or more.

Examples of bisphenols include bisphenol A, bisphenol S, bisphenol F, low-condensates of phenols and formaldehyde, and the like. These bisphenols may be a mixture of two or more.

Examples of polyester polyols include polyester polyols obtained by the condensation reaction of a single or a mixture of dibasic acids selected from the group of carboxylic acids, such as succinic acid, adipic acid, sebacic acid, dimer acid, maleic anhydride, phthalic anhydride, isophthalic acid, and terephthalic acid, with a single or a mixture of polyhydric alcohols selected from the group of ethylene glycol, propylene glycol, diethylene glycol, neopentyl glycol, trimethylolpropane, glycerol, etc.; and polycaprolactones obtained by the ring-opening polymerization of ε-caprolactone using a polyhydric alcohol. These polyester polyols may be a mixture of two or more.

Acrylic polyols are compounds obtained by copolymerizing a single or a mixture of ethylenically unsaturated bond-containing monomers having a hydroxyl group with a single or a mixture of other ethylenically unsaturated bond-containing monomers copolymerizable therewith. Examples of the ethylenically unsaturated bond-containing monomer having a hydroxyl group include hydroxyethyl acrylate, hydroxypropyl acrylate, hydroxybutyl acrylate, hydroxyethyl methacrylate, hydroxypropyl methacrylate, hydroxybutyl methacrylate, and the like; and preferably hydroxyethyl acrylate and hydroxyethyl methacrylate. These acrylic polyols may be a mixture of two or more.

Examples of the other ethylenically unsaturated bond-containing monomers copolymerizable with the ethylenically unsaturated bond-containing monomer having a hydroxyl group include acrylates, such as methyl acrylate, ethyl acrylate, propyl acrylate, isopropyl acrylate, n-butyl acrylate, isobutyl acrylate, n-hexyl acrylate, cyclohexyl acrylate, 2-ethylhexyl acrylate, lauryl acrylate, benzyl acrylate, and phenyl acrylate; methacrylates, such as methyl methacrylate, ethyl methacrylate, propyl methacrylate, isopropyl methacrylate, n-butyl methacrylate, isobutyl methacrylate, n-hexyl methacrylate, cyclohexyl methacrylate, 2-ethylhexyl methacrylate, lauryl methacrylate, benzyl methacrylate, and phenyl methacrylate; unsaturated carboxylic acids, such as acrylic acid, methacrylic acid, maleic acid, and itaconic acid; unsaturated amides, such as acrylamide, methacrylamide, N,N-methylenebisacrylamide, diacetone acrylamide, diacetone methacrylamide, maleic acid amide, and maleimide; vinyl monomers, such as glycidyl methacrylate, styrene, vinyl toluene, vinyl acetate, acrylonitrile, and dibutyl fumarate; vinyl monomers having a hydrolyzable silyl group, such as vinyltrimethoxysilane, vinylmethyldimethoxysilane, and γ-(meth)acryloxypropyltrimethoxysilane; and the like.

Examples of polyolefin polyols include polybutadiene having two or more hydroxyl groups, hydrogenated polybutadiene, polyisoprene, hydrogenated polyisoprene, and the like. These polyolefin polyols may be a mixture of two or more.

Fluorine polyols are polyols containing fluorine in the molecule. Examples include copolymers of fluoroolefin, cyclovinyl ether, hydroxyalkyl vinyl ether, and vinyl monocarboxylate. These fluorine polyols may be a mixture of two or more.

Examples of polycarbonate polyols include those obtained by condensation polymerization of low-molecular-weight carbonate compounds, such as dialkyl carbonates (e.g., dimethyl carbonate), alkylene carbonates (e.g., ethylene carbonate), and diaryl carbonates (e.g., diphenyl carbonate), with low-molecular-weight polyols used in the polyester polyols described above. These polycarbonate polyols may be a mixture of two or more.

Polyurethane polyols can be obtained by a conventional method, for example, by reacting polyols and polyisocyanates. Examples of carboxyl group-free polyols include ethylene glycol and propylene glycol as low-molecular-weight polyols, and acrylic polyol, polyester polyol, and polyether polyol as high-molecular-weight polyols. These polyurethane polyols may be a mixture of two or more.

In the present invention, polyamines are compounds having two or more amino groups. Examples of polyamines include low-molecular-weight polyamines, high-molecular-weight polyamines, alkanolamines, and the like. These polyamines may be a mixture of two or more.

Examples of low-molecular-weight polyamines include aromatic amines, such as 4,4'-diphenylmethanediamine; araliphatic amines, such as 1,3- or 1,4-xylylenediamine and mixtures thereof; alicyclic amines, such as 3-aminomethyl-3,5,5-trimethylcyclohexylamine, 1,3-bis(aminomethyl)cyclohexane, and 1,4-cyclohexanediamine; aliphatic amines, such as ethylenediamine, 1,3-propanediamine, 1,4-butanediamine, 1,6-hexamethylenediamine, hydrazine, diethylenetriamine, triethylenetetramine, and tetraethylenepentamine; and the like. These low-molecular-weight polyamines may be a mixture of two or more.

Examples of high-molecular-weight polyamines include polyoxyalkylene diamine (weight average molecular weight: 400 to 4000), polyoxyalkylene triamine (weight average molecular weight: 400 to 5000), and the like. These high-molecular-weight polyamines may be a mixture of two or more.

Examples of alkanolamines include monoethanolamine, diethanolamine, N-(2-aminoethyl)ethanolamine, N-(2-hydroxypropyl)ethylenediamine, mono-n-propanolamine, mono-n-isopropanolamine, di-n-propanolamine, diisopropanolamine, ethylene glycol bis(3-aminopropyl)ether, neopentanolamine, methylethanolamine, and the like.

In the thermosetting composition of the present invention, the mixing ratio of the blocked isocyanate and the compound having an isocyanate-reactive group is determined by the required physical properties, and is not particularly limited. The mixing ratio is generally within the following range: [effective isocyanate groups (mol) in the blocked isocyanate]/[active hydrogen groups (mol) in the compound having an isocyanate-reactive group]=0.2 to 3. The effective isocyanate groups in the blocked isocyanate refer to isocyanate groups that are regenerated when the blocking agent is dissociated from the blocked isocyanate.

In the thermosetting composition of the present invention, the amount of the blocking agent dissociation catalyst (A) of the present invention used is not particularly limited. The amount of the nitrogen-containing compound (1) contained in the blocking agent dissociation catalyst (A) is generally 0.1 to 15 wt. %, preferably 0.5 to 10 wt. %, and more preferably 1 to 5 wt. %, based on the blocked isocyanate.

In the thermosetting composition of the present invention, known catalysts for polyurethane production, additives, pigments, solvents, and the like that are commonly used in this technical field can be used, if necessary.

Known catalysts for polyurethane production are not particularly limited. Examples include tin compounds, such as dibutyltin dilaurate, dibutyltin di-2-ethylhexanate, dioctyltin dilaurate, dibutyltin diacetate, dibutyltin dioxide, dioctyltin dioxide, tin acetylacetonate, tin acetate, tin octylate, and tin laurate; bismuth compounds, such as bismuth octylate, bismuth naphthenate, and bismuth acetylacetonate; titanium compounds, such as tetra-n-butyl titanate, tetraisopropyl titanate, and titanium terephthalate; tertiary amine compounds, such as triethylamine, N,N,N',N'-tetramethylethylenediamine, N,N,N',N'-tetramethylpropylenediamine, N,N,N',N'',N''-pentamethyldiethylenetriamine, N,N,N',N'',N''-pentamethyldipropylenetriamine, N,N,N',N'-tetramethylguanidine, 1,3,5-tris(N,N-dimethylaminopropyl)hexahydro-S-triazine, 1,4-diazabicyclo[2.2.2]octane (DABCO), 1,8-diazabicyclo[5.4.0]undecene-7, triethylenediamine, N,N,N',N'-tetramethylhexamethylenediamine, N-methyl-N'-(2-dimethylaminoethyl)piperazine, N,N'-dimethylpiperazine, dimethylcyclohexylamine, N-methylmorpholine, N-ethylmorpholine, bis(2-dimethylaminoethyl)ether, 1-methylimidazole, 1,2-dimethylimidazole, 1-isobutyl-2-methylimidazole, and 1-dimethylaminopropylimidazole; and quaternary ammonium salt compounds, such as tetraalkylammonium halides (e.g., tetramethylammonium chloride), tetraalkylammonium hydroxides (e.g., tetramethylammonium hydroxide salts), tetraalkylammonium organic acid salts (e.g., tetramethylammonium-2-ethylhexanoate, 2-hydroxypropyl trimethylammonium formate, and 2-hydroxypropyl trimethylammonium-2-ethylhexanoate).

Additives are not particularly limited. Examples include hindered amine-based, benzotriazole-based, and benzophenone-based UV absorbers; perchlorate-based and hydroxylamine-based coloration inhibitors; hindered phenol-based, phosphorus-based, sulfur-based, and hydrazide-based antioxidants; tin-based, zinc-based, and amine-based urethanization catalysts; leveling agents, rheology control agents, pigment dispersants, and the like.

Pigments are not particularly limited. Examples include organic pigments, such as quinacridone-based, azo-based, and phthalocyanine-based pigments; inorganic pigments, such as titanium oxide, barium sulfate, calcium carbonate, and silica; and other pigments, such as carbon-based pigments, metal foil pigments, and rust-preventive pigments.

Solvents are not particularly limited. Examples include hydrocarbons, such as benzene, toluene, xylene, cyclohexane, mineral spirit, and naphtha; ketones, such as acetone, methyl ethyl ketone, and methyl isobutyl ketone; esters, such as ethyl acetate, n-butyl acetate, and cellosolve acetate; alcohols, such as methanol, ethanol, 2-propanol, n-butanol, 2-methoxyethanol, 2-ethoxyethanol, and 2-n-butoxyethanol; polyhydric alcohols, such as ethylene glycol, propylene glycol, diethylene glycol, polyethylene glycol, and glycerol; water; and the like. These solvents may be used singly or in combination of two or more.

When storage at high temperatures is assumed, the thermosetting composition of the present invention may be divided into a blocked isocyanate and a compound having an isocyanate-reactive group to form two-part thermosetting compositions, and when used, the two-part thermosetting compositions may be mixed to be used as the thermosetting composition of the present invention. In such a case, the blocking agent dissociation catalyst (A) can be added and used when the two-part thermosetting compositions are mixed, or the compound having an isocyanate-reactive group and the blocking agent dissociation catalyst (A) can be mixed in advance.

The thermosetting composition of the present invention can be used as top and intermediate coat paints for automobiles, anti-chipping paints, electrodeposition paints, paints for automotive parts, paints for automotive repair, paints for pre-coated metal and rust-proof steel plates for metal products, such as home appliances and office equipment, paints for building materials, paints for plastics, powder paints, adhesives, adhesion-imparting agents, sealing agents, and the like.

Next, the blocking agent dissociation method of the present invention is explained.

In the method of the present invention, a blocked isocyanate is heated in the presence of the blocking agent dissociation catalyst for blocked isocyanates described above.

The method of the present invention can be performed in the presence or absence of a solvent. Examples of solvents include aromatic hydrocarbon solvents, such as toluene, benzene, and xylene; aliphatic or alicyclic hydrocarbon solvents, such as hexane, heptane, octane, and cyclohexane; ester solvents, such as ethyl acetate and butyl acetate; ketone solvents, such as acetone, 3-pentanone, and 4-methyl-2-pentanone; alcohol solvents, such as ethanol, isopropanol, 2-ethoxyethanol, and 2-butoxyethanol; glycol solvents, such as ethylene glycol, diethylene glycol, and dipropylene glycol; water; and the like. The solvents can be used as a mixture of two or more, if necessary.

The amount of solvent used is generally 50 parts by weight or less, and preferably 0.1 parts by weight or more and 35 parts by weight or less, per part by weight of the blocked isocyanate.

In the method of the present invention, the amount of the blocking agent dissociation catalyst (A) used is not particularly limited. The amount of the nitrogen-containing compound (1) contained in the blocking agent dissociation catalyst (A) is generally 0.1 to 15 wt. %, preferably 0.5 to 10 wt. %, and more preferably 1 to 5 wt. %, based on the blocked isocyanate.

The reaction temperature varies depending on the blocked isocyanate used, but is generally about 60 to 250° C., and preferably about 80 to 200° C. The reaction time is about 30 seconds to 5 hours, and preferably about 1 minute to 30 minutes.

The sealing with a blocking agent can be released by the method of the present invention.

EXAMPLES

The present invention is described in detail below based on Examples; however, the present invention is not limited to these. In the Production Examples, a Bruker AV400 was used for $^1$H-NMR measurement, which was performed at 400 MHz. IR spectroscopy was performed on an IRAffinity-1 Fourier transform infrared spectrophotometer produced by Shimadzu Corporation and a DuraSamplIRII produced by Smiths Detection, based on a total reflection measurement method. In the Examples, the curing temperature of the thermosetting compositions was measured under the following conditions.

Curing Temperature Measurement Conditions
Device: Automatic curing time measuring device Madoka produced by Cyber Co., Ltd.
Stirring rod: Model number 3JC-5060W
Stirring rate: rotation 100 rpm, revolution 25 rpm
Heating rate: 10° C./min Production Example 1: Synthesis of m-chloro-N-t-butoxycarbonylaniline

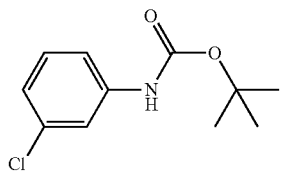

2.0 g (15.7 mmol) of m-chloroaniline, 1.8 g (17.3 mmol) of triethylamine, and 10 mL of THF were placed in a 100-mL test tube purged with nitrogen. While stirring the mixture, a solution of 3.4 g (15.7 mmol) of di-t-butyl dicarbonate and 10 mL of THF was added dropwise. The resulting mixture was stirred at 25° C. for 4 hours, and then further stirred at 40° C. for 24 hours. After the obtained reaction mixture was cooled to 25° C., the solvent was distilled off. Then, 20 mL of toluene was added to the obtained concentrated residue, and the resulting mixture was washed once with 20 mL of 1 M citric acid aqueous solution and once with 20 mL of water. After the obtained organic phase was dried over magnesium sulfate, insoluble substances were removed by filtration. The obtained filtrate was dried under reduced pressure, thereby obtaining 1.4 g of a compound represented by the above formula (m-chloro-N-t-butoxycarbonylaniline) (yield: 39%). The $^1$H-NMR analysis results of the compound represented by the above formula are shown below.

$^1$H-NMR (CDCl$_3$) δ (ppm)=7.52 (s, 1H), 7.21-7.14 (m, 2H), 7.00 (dt, J=7.5, 1.7 Hz, 1H), 6.52 (s, 1H), 1.52 (s, 9H)

Production Example 2: Synthesis of o-chloro-N-t-butoxycarbonylaniline

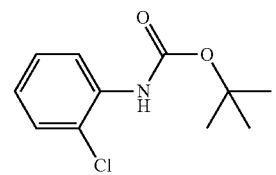

1.0 g (6.5 mmol) of o-chlorophenyl isocyanate and 2.0 g (27.0 mmol) of 2-methyl-2-propanol were placed in a 15-mL test tube purged with nitrogen, and stirred at 90° C. for 3 hours. After the obtained reaction mixture was cooled to 25° C., the solvent was distilled off. After the obtained concentrated residue was dissolved in chloroform, insoluble substances were removed by filtration. The obtained filtrate was dried under reduced pressure, thereby obtaining 1.0 g of a compound represented by the above formula (o-chloro-N-t-butoxycarbonylaniline) (yield: 64%). The $^1$H-NMR analysis results of the compound represented by the above formula are shown below.

$^1$H-NMR (CDCl$_3$) δ (ppm)=8.16 (d, J=8.2 Hz, 1H), 7.33 (dd, J=8.2, 1.4 Hz, 1H), 7.24 (t, J=7.7 Hz, 1H), 7.01 (s, 1H), 6.96 (td, J=7.7, 1.4 Hz, 1H), 1.53 (s, 9H)

Production Example 3: Synthesis of p-methoxy-N-t-butoxycarbonylaniline

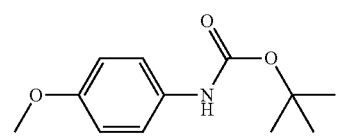 [SMILES: COc1ccc(NC(=O)OC(C)(C)C)cc1]

1.0 g (8.1 mmol) of p-anisidine, 0.9 g (8.9 mmol) of triethylamine, and 5 mL of THF were placed in a 100-mL test tube purged with nitrogen. While stirring the mixture, a solution of 2.0 g (8.9 mmol) of di-t-butyl dicarbonate and 5 mL of THF was added dropwise and stirred at 25° C. for 17 hours. The solvent of the obtained reaction mixture was distilled off, and the resulting concentrated residue was washed with 5 mL of heptane. After washing, the obtained solid was dried under reduced pressure, thereby obtaining 1.9 g of a compound represented by the above formula (p-methoxy-N-t-butoxycarbonylaniline) (yield: 85%). The $^1$H-NMR analysis results of the compound represented by the above formula are shown below.

$^1$H-NMR (CDCl$_3$) δ (ppm)=7.26 (d, J=8.8 Hz, 2H), 6.83 (d, J=8.8 Hz, 2H), 6.33 (s, 1H), 3.78 (s, 3H), 1.51 (s, 9H)

Production Example 4: Synthesis of 2,6-diisopropyl-N-t-butoxycarbonylaniline

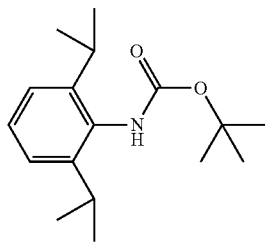 [SMILES: CC(C)c1cccc(C(C)C)c1NC(=O)OC(C)(C)C]

1.0 g (5.6 mmol) of 2,6-diisopropylaniline, 0.6 g (5.6 mmol) of triethylamine, and 5 mL of THF were placed in a 100-mL test tube purged with nitrogen. While stirring the mixture, a solution of 1.2 g (5.6 mmol) of di-t-butyl dicarbonate and 5 mL of THF was added dropwise and stirred at 25° C. for 21 hours. After the reaction mixture was cooled to 25° C., the solvent was distilled off, and 10 mL of toluene was added to the obtained concentrated residue. The resulting mixture was washed once with 15 mL of acetic acid aqueous solution (1 g/15 mL) and once with 10 mL of water. After the obtained organic phase was dried over magnesium sulfate, insoluble substances were removed by filtration. The obtained filtrate was dried under reduced pressure, thereby obtaining 1.1 g of a compound represented by the above formula (2,6-diisopropyl-N-t-butoxycarbonylaniline) (yield: 71%). The $^1$H-NMR analysis results of the compound represented by the above formula are shown below. The $^1$H-NMR analysis results showed that this compound was a mixture of rotamers.

$^1$H-NMR (CDCl$_3$) δ (ppm)=7.26 (m, 1H), 7.14 (d, J=7.1 Hz, 2H), 5.81 (s, 0.7H), 5.58 (s, 0.3H), 3.18-3.17 (m, 2H), 1.51 (s, 6H), 1.37 (s, 3H), 1.21 (d, J=6.8 Hz, 12H)

Production Example 5: Synthesis of bis[4-(t-butoxycarbonylamino)phenyl]methane

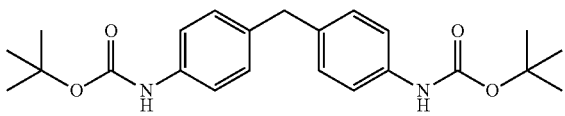 [SMILES: CC(C)(C)OC(=O)Nc1ccc(Cc2ccc(NC(=O)OC(C)(C)C)cc2)cc1]

15.0 g (60 mmol) of 4,4'-methylenediphenyl diisocyanate, 22.2 g (300 mmol) of 2-methyl-2-propanol, and 44 g of toluene were placed in a 200-mL test tube purged with nitrogen, and stirred at 85° C. for 3 hours. The obtained reaction mixture was dried under reduced pressure, thereby obtaining 22.8 g of a compound represented by the above formula (bis[4-(t-butoxycarbonylamino)phenyl]methane) (yield: 96%). The $^1$H-NMR analysis results of the compound represented by the above formula are shown below.

$^1$H-NMR (DMSO-d6) δ (ppm)=9.23 (s, 2H) 7.34 (d, J=8.6 Hz, 4H), 7.05 (d, J=8.6 Hz, 4H), 3.76 (s, 2H), 1.45 (s, 18H)

Production Example 6: Synthesis of bis[3-(t-butoxycarbonylamino)phenyl]sulfone

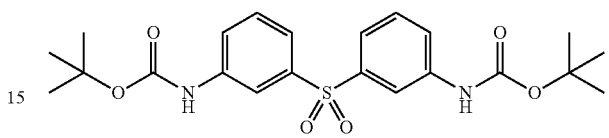

2.0 g (8.1 mmol) of bis(3-aminophenyl)sulfone, 2.0 g (16.1 mmol) of di-t-butyl dicarbonate, and 20 mL of THF were placed in a 100-mL test tube purged with nitrogen. While stirring the mixture, 1.8 g (17.7 mmol) of triethylamine was added dropwise. The resulting mixture was stirred at 25° C. for 6 hours, and then further stirred at 40° C. for 16 hours. Thereafter, 5.5 g (25.2 mmol) of di-t-butyl dicarbonate was added, and further stirred at 40° C. for 48 hours. 1.7 g (15.9 mmol) of diethanolamine was added dropwise to the obtained reaction mixture. After stirring for 1 hour, the obtained reaction mixture was dried under reduced pressure. 15 mL of ethyl acetate was added to the obtained concentrated residue, and the resulting mixture was washed once with 15 mL of water. After the obtained organic phase was dried over magnesium sulfate, insoluble substances were removed by filtration. The obtained filtrate was dried under reduced pressure, thereby obtaining 3.5 g of a compound represented by the above formula (bis[3-(t-butoxycarbonylamino)phenyl]sulfone) (yield: 93%). The $^1$H-NMR analysis results of the compound represented by the above formula are shown below.

$^1$H-NMR (CDCl$_3$) δ (ppm)=7.86 (s, 2H), 7.68 (d, J=7.3 Hz, 2H), 7.58 (d, J=7.3 Hz, 2H), 7.43-7.39 (m, 2H), 6.67 (s, 2H), 1.51 (s, 18H)

Production Example 7: Synthesis of 1,3-bis[4-(t-butoxycarbonylamino)phenoxy]benzene

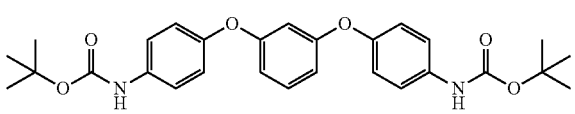 [SMILES: CC(C)(C)OC(=O)Nc1ccc(Oc2cccc(Oc3ccc(NC(=O)OC(C)(C)C)cc3)c2)cc1]

7.5 g (34.3 mmol) of di-t-butyl dicarbonate, 1.7 g (17.2 mmol) of triethylamine, and 40 mL of THF were placed in a 200-mL three-necked flask purged with nitrogen. While stirring the mixture, a solution of 5.0 g (17.2 mmol) of 1,3-bis(4-aminophenoxy)benzene and 10 mL of THF was added dropwise. After the resulting mixture was stirred at 25° C. for 6 hours, 3.8 g (17.4 mmol) of di-t-butyl dicarbonate was added, and the resulting mixture was further stirred for 3 hours. Then, 2.8 g (26.3 mmol) of diethanolamine was added to the obtained reaction mixture. After stirring for 1 hour, the obtained reaction mixture was dried under reduced pressure. 100 mL of toluene was added to the obtained concentrated residue, and the resulting mixture was washed once with 100 mL of water. Then, 100 mL of toluene, 10 mL of chlorobenzene, and 20 mL of ethyl acetate were added thereto, and the resulting mixture was washed with 100 mL of water. Additionally, 80 mL of ethyl acetate was added thereto, and the resulting mixture was washed twice with 100 mL of water. The obtained organic phase was dried under reduced pressure, thereby obtaining 8.0 g of a compound represented by the above formula (1,3-bis[4-(t-butoxycarbonylamino)phenoxy]benzene) (yield: 94%). The ¹H-NMR analysis results of the compound represented by the above formula are shown below.

¹H-NMR (CD₃OD) δ (ppm)=7.38 (d, J=8.8 Hz, 4H), 7.23 (t, J=8.4 Hz, 1H), 6.93 (d, J=8.8 Hz, 4H), 6.40 (dd, J=8.4, 2.2 Hz, 2H), 6.50 (d, J=2.2 Hz, 1H), 1.51 (s, 18H)

Production Example 8: Synthesis of 1,3-bis{2-[4-(t-butoxycarbonylamino)phenyl]-2-propyl}benzene

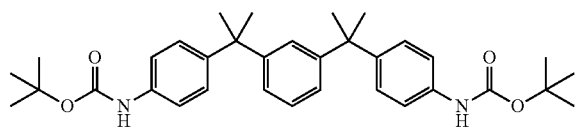 [SMILES: CC(C)(C)OC(=O)Nc1ccc(C(C)(C)c2cccc(C(C)(C)c3ccc(NC(=O)OC(C)(C)C)cc3)c2)cc1]

12.7 g (58 mmol) of di-t-butyl dicarbonate, 3.3 g (33 mmol) of triethylamine, and 25.0 g of THF were placed in a 200-mL test tube purged with nitrogen. While stirring the mixture, a solution of 5.0 g (14.5 mmol) of 4,4-(1,3-phenylenediisopropylidene)bisaniline and 30.0 g of THF was added dropwise. The resulting mixture was stirred at 25° C. for 4 hours. 3.1 g (290 mmol) of diethanolamine was added to the obtained liquid reaction mixture, and after stirring for 1 hour, the obtained reaction mixture was dried under reduced pressure. Then, 200 mL of ethyl acetate was added to the obtained concentrated residue, and the resulting mixture was washed three times with 100 mL of water. After the obtained organic phase was dried over magnesium sulfate, insoluble substances were removed by filtration. The obtained filtrate was dried under reduced pressure, thereby obtaining 6.3 g of a compound represented by the above formula (1,3-bis{2-[4-(t-butoxycarbonylamino)phenyl]-2-propyl}benzene) (yield: 80%). The ¹H-NMR analysis results of the compound represented by the above formula are shown below.

¹H-NMR (DMSO-d6) δ (ppm)=9.22 (s, 2H), 7.31 (d, J=8.6 Hz, 4H), 7.12 (t, J=7.7 Hz, 1H), 7.14-7.03 (m, 5H), 6.94 (d, J=7.7 Hz, 2H), 3.34 (s, 12H), 1.45 (s, 18H)

¹H-NMR (CDCl₃) δ (ppm)=7.26-7.22 (m, 4H), 7.15-7.13 (m, 4H), 7.08-7.07 (m, 4H), 6.40 (br, 2H), 1.62 (s, 12H), 1.50 (s, 18H)

Production Example 9: Synthesis of 1-methyl-3-octylimidazolium-2-carboxylate

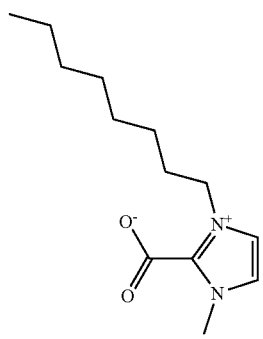 [SMILES: CCCCCCCC[n+]1ccn(C)c1C(=O)[O-]]

25.0 g (139 mmol) of 1-octyl imidazole, 16.7 g (185 mmol) of dimethyl carbonate, and 25.1 g of methanol were placed in a 180-mL autoclave purged with nitrogen, and stirred at 125° C. for 29 hours. After the obtained reaction mixture was cooled to a temperature equal to or lower than the boiling point of the solvent, 8.5 g (94 mmol) of dimethyl carbonate was added thereto, followed by stirring at 130° C. for 3 hours. The obtained reaction mixture was cooled to 25° C., thereby obtaining 44.0 g of a solution of a compound represented by the above formula (1-methyl-3-octylimidazolium-2-carboxylate) in methanol (pure content: 33.0 g, yield: 99%). The ¹H-NMR analysis results of the compound represented by the above Formula are shown below.

¹H-NMR (CD₃OD) δ (ppm)=7.67 (s, 1H), 7.61 (s, 1H), 4.22 (t, J=7.2 Hz, 2H), 3.94 (s, 3H), 1.91-1.84 (m, 2H), 1.32-1.26 (m, 10H), 0.85 (t, J=7.2 Hz, 3H)

Production Example 10: Synthesis of Blocking Agent Dissociation Catalyst (C1)

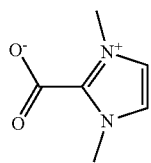

82.1 g (1.0 mol) of 1-methyl imidazole, 119.8 g (1.0 mol) of dimethyl carbonate, and 83.1 g of methanol were placed in a 500-mL autoclave purged with nitrogen, followed by stirring at 120° C. for 22 hours. The obtained reaction mixture was cooled to 25° C., and then dried under reduced pressure. The obtained white solid was washed with toluene, and then dried under reduced pressure, thereby obtaining 47.8 g of a blocking agent dissociation catalyst (C1) represented by the above formula (yield: 34%). The ¹H-NMR analysis results of the compound represented by the above Formula are shown below.

¹H-NMR (CD₃OD) δ (ppm)=7.46 (s, 2H), 4.08 (s, 6H)

Production Example 11: Synthesis of Blocking Agent Dissociation Catalyst (C2)

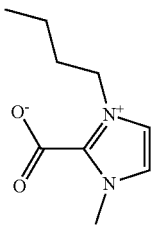

25.9 g (0.2 mol) of 1-butylimidazole, 25.0 g (0.3 mol) of dimethyl carbonate, and 26.2 g of methanol were placed in a 180-mL autoclave purged with nitrogen, and the mixture was stirred at 125° C. for 19 hours and at 130° C. for another 4 hours. The obtained reaction mixture was cooled to 25° C., thereby obtaining 73.0 g of a blocking agent dissociation catalyst (C2) as a solution of a compound represented by the above formula (1-butyl-3-methylimidazolium-2-carboxylate) in methanol (pure content of 1-butyl-3-methylimidazolium-2-carboxylate: 34.3 g, yield: 95%). The $^1$H-NMR analysis results of the compound represented by the above Formula are shown below.

$^1$H-NMR (CD$_3$OD) δ (ppm)=7.79 (s, 1H), 7.72 (s, 1H), 4.31 (t, J=7.4 Hz, 2H), 4.02 (s, 3H), 1.94-1.88 (m, 2H), 1.44-1.38 (m, 2H), 1.00 (t, J=7.2 Hz, 3H)

Production Example 12: Synthesis of Blocking Agent Dissociation Catalyst (C3)

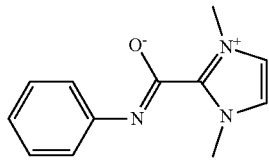 [SMILES: Cn1cc[n+](C)c1/C([O-])=N/c1ccccc1]

3.0 g (21 mmol) of 1,3-dimethylimidazolium-2-carboxylate obtained in Production Example 10, 100 mL of toluene, and 2.5 g (21 mmol) of phenyl isocyanate were placed in a three-necked flask purged with nitrogen, followed by stirring at 110° C. for 3 hours. The obtained reaction mixture was cooled to 25° C., and then concentrated under reduced pressure, thereby obtaining 5.3 g of a blocking agent dissociation catalyst (C3) represented by the above formula (pure content of the compound represented by the above formula: 4.9 g, yield: 97%). The $^1$H-NMR analysis results of the compound represented by the above Formula are shown below.

$^1$H-NMR (CD$_3$OD) δ (ppm)=7.45 (m, 2H), 7.35-7.27 (m, 4H), 7.00 (m, 1H), 3.98 (s, 6H)

Production Example 13: Synthesis of Blocking Agent Dissociation Catalyst (C4)

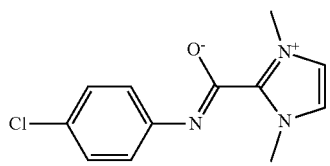 [SMILES: Cn1cc[n+](C)c1/C([O-])=N/c1ccc(Cl)cc1]

3.0 g (21 mmol) of 1,3-dimethylimidazolium-2-carboxylate obtained in Production Example 10, 100 mL of toluene, and 3.3 g (21 mmol) of p-chlorophenyl isocyanate were placed in a three-necked flask purged with nitrogen, followed by stirring at 110° C. for 3 hours. After the obtained reaction mixture was cooled to 25° C., filtration was performed, and the obtained yellow solid was dried under reduced pressure, thereby obtaining 4.6 g of a blocking agent dissociation catalyst (C4) represented by the above formula (yield: 88%). The $^1$H-NMR analysis results of the compound represented by the above Formula are shown below.

$^1$H-NMR (CD$_3$OD) δ (ppm)=7.47 (s, 2H), 7.39 (m, 2H), 7.25 (m, 2H), 3.99 (s, 6H)

Production Example 14: Synthesis of Blocking Agent Dissociation Catalyst (C5)

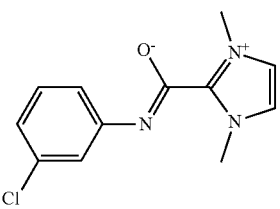 [SMILES: Cn1cc[n+](C)c1/C([O-])=N/c1cccc(Cl)c1]

0.31 g (2.24 mmol) of 1,3-dimethylimidazolium-2-carboxylate obtained in Production Example 10, 0.51 g (2.23 mmol) of m-chloro-N-t-butoxycarbonylaniline obtained in Production Example 1, and 9 mL of toluene were placed in a 30-mL test tube purged with nitrogen, followed by stirring at 110° C. for 3 hours. After the obtained reaction mixture was cooled to 25° C., filtration was performed, and the obtained white solid was dried under reduced pressure, thereby obtaining 0.44 g of a blocking agent dissociation catalyst (C5) represented by the above formula (yield: 80%). The $^1$H-NMR analysis results of the compound represented by the above Formula are shown below.

$^1$H-NMR (DMSO-d6) δ (ppm)=7.78 (t, J=2.0 Hz, 1H), 7.55 (s, 2H), 7.26 (d, J=9.6 Hz, 1H), 7.13 (t, J=8.0 Hz, 1H), 6.81 (d, J=7.8 Hz, 1H), 4.00 (s, 6H)

Production Example 15: Synthesis of Blocking Agent Dissociation Catalyst (C6)

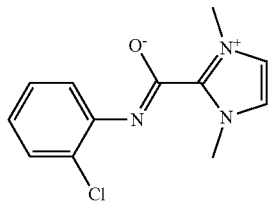 [SMILES: Cn1cc[n+](C)c1/C([O-])=N/c1ccccc1Cl]

0.31 g (2.20 mmol) of 1,3-dimethylimidazolium-2-carboxylate obtained in Production Example 10, 0.50 g (2.20 mmol) of o-chloro-N-t-butoxycarbonylaniline obtained in Production Example 2, and 9 mL of toluene were placed in a 30-mL test tube purged with nitrogen, followed by stirring at 110° C. for 6 hours. After the obtained reaction mixture was cooled to 25° C., filtration was performed, and the obtained white solid was dried under reduced pressure, thereby obtaining 0.47 g of a blocking agent dissociation catalyst (C6) represented by the above formula (yield: 85%). The $^1$H-NMR analysis results of the compound represented by the above Formula are shown below.

$^1$H-NMR (DMSO-d6) δ (ppm)=7.93 (d, J=7.8 Hz, 1H), 7.57 (s, 2H), 7.28 (d, J=7.8 Hz, 1H), 7.09 (t, J=8.0 Hz, 1H), 6.79 (t, J=7.6 Hz, 1H), 4.09 (s, 6H)

Production Example 16: Synthesis of Blocking Agent Dissociation Catalyst (C7)

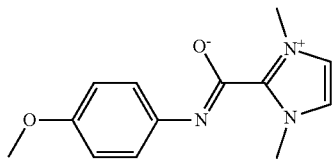 [SMILES: COc1ccc(/N=C(\[O-])c2n(C)cc[n+]2C)cc1]

0.31 g (2.24 mmol) of 1,3-dimethylimidazolium-2-carboxylate obtained in Production Example 10, 0.50 g (2.24 mmol) of p-methoxy-N-t-butoxycarbonylaniline obtained in Production Example 3, and 9 mL of toluene were placed in a 30-mL test tube purged with nitrogen, followed by stirring at 110° C. for 12 hours. After the obtained reaction mixture was cooled to 25° C., filtration was performed, and the obtained white solid was dried under reduced pressure, thereby obtaining 0.43 g of a blocking agent dissociation catalyst (C7) represented by the above formula (yield: 79%). The $^1$H-NMR analysis results of the compound represented by the above Formula are shown below.

$^1$H-NMR (DMSO-d6) δ (ppm)=7.50-7.49 (m, 4H), 6.71 (d, J=9.1 Hz, 2H), 3.99 (s, 6H), 3.68 (s, 3H)

Production Example 17: Synthesis of Blocking Agent Dissociation Catalyst (C8)

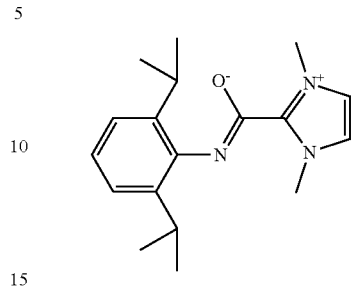

0.25 g (1.80 mmol) of 1,3-dimethylimidazolium-2-carboxylate obtained in Production Example 10, 0.50 g (1.80 mmol) of 2,6-diisopropyl-N-t-butoxycarbonylaniline obtained in Production Example 4, and 6 mL of toluene were placed in a 15-mL test tube purged with nitrogen, followed by stirring at 110° C. for 12 hours. After the obtained reaction mixture was cooled to 25° C., filtration was performed, and the obtained white solid was dried under reduced pressure, thereby obtaining 0.46 g of a blocking agent dissociation catalyst (C8) represented by the above formula (yield: 83%). The $^1$H-NMR analysis results of the compound represented by the above Formula are shown below.

$^1$H-NMR (DMSO-d6) δ (ppm)=7.54 (s, 2H), 6.94 (d, J=7.6 Hz, 2H), 6.81 (t, J=7.5 Hz, 1H), 4.01 (s, 6H)), 3.20-3.13 (m, 2H), 1.10 (d, J=6.8 Hz, 12H)

Production Example 18: Synthesis of Blocking Agent Dissociation Catalyst (C9)

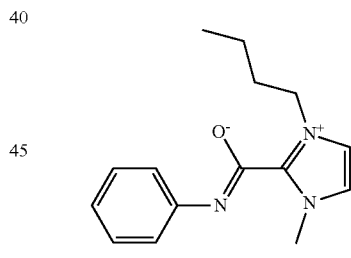

6.0 g of a solution of 1-butyl-3-methylimidazolium-2-carboxylate obtained in Production Example 11 in methanol (pure content of 1-butyl-3-methylimidazolium-2-carboxylate: 2.8 g (16 mmol)), 1.9 g (16 mmol) of phenyl isocyanate, and 100 mL of toluene were placed in a 200-mL test tube purged with nitrogen, followed by stirring at 110° C. for 3 hours. The obtained reaction mixture was cooled to 25° C., and then concentrated under reduced pressure, thereby obtaining 4.1 g of a blocking agent dissociation catalyst (C9) represented by the above formula (yield: 97%). The $^1$H-NMR analysis results of the compound represented by the above formula are shown below.

$^1$H-NMR (CD$_3$OD) δ (ppm)=7.53 (s, 1H), 7.47 (s, 1H), 7.33-7.25 (m, 4H), 7.00 (t, J=7.2 Hz, 1H), 4.38 (t, J=7.4 Hz, 2H), 3.98 (s, 3H), 1.89 (quint, J=7.6 Hz, 2H), 1.39 (sext, J=7.4 Hz, 2H), 0.97 (t, J=7.2 Hz, 3H)

Production Example 19: Synthesis of Blocking Agent Dissociation Catalyst (C10)

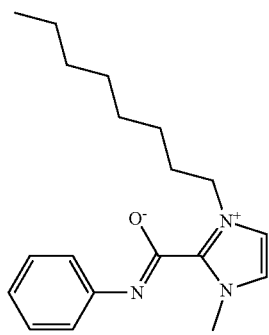 [SMILES: CCCCCCCC[n+]1ccn(C)c1/C([O-])=N/c1ccccc1]

4.0 g of a solution of 1-methyl-3-octylimidazolium-2-carboxylate obtained in Production Example 9 in methanol (pure content of 1-methyl-3-octylimidazolium-2-carboxylate: 3.0 g (13 mmol)), 1.5 g (13 mmol) of phenyl isocyanate, and 100 mL of toluene were placed in a 200-mL test tube purged with nitrogen, followed by stirring at 110° C. for 3 hours. The obtained reaction mixture was cooled to 25° C., and then concentrated under reduced pressure, thereby obtaining 3.3 g of a blocking agent dissociation catalyst (C10) represented by the above formula (yield: 84%). The $^1$H-NMR analysis results of the compound represented by the above formula are shown below.

$^1$H-NMR (CD$_3$OD) δ (ppm)=7.51 (s, 1H), 7.45-7.33 (m, 6H), 4.37 (t, J=7.4 Hz, 2H), 3.97 (s, 3H), 1.91-1.86 (m, 2H), 1.35-1.27 (m, 10H), 0.88 (t, J=6.8 Hz, 3H)

Production Example 20: Synthesis of Blocking Agent Dissociation Catalyst (C11)

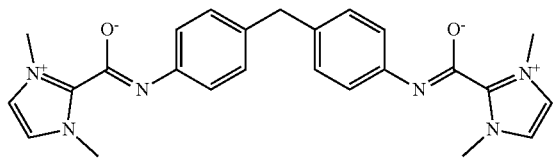 [SMILES: Cn1cc[n+](C)c1/C([O-])=N/c1ccc(Cc2ccc(/N=C(\[O-])c3n(C)cc[n+]3C)cc2)cc1]

3.0 g (22 mmol) of 1,3-dimethylimidazolium-2-carboxylate obtained in Production Example 10, 3.5 g (11 mmol) of bis[4-(t-butoxycarbonylamino)phenyl]methane obtained in Production Example 5, and 120 mL of chlorobenzene were placed in a 200-mL test tube purged with nitrogen, followed by stirring at 130° C. for 3 hours. The obtained liquid reaction mixture was cooled to 25° C., and then concentrated under reduced pressure, thereby obtaining 3.9 g of a blocking agent dissociation catalyst (C11) represented by the above formula (yield: 81%). The $^1$H-NMR analysis results of the compound represented by the above Formula are shown below.

$^1$H-NMR (DMSO-d6) δ (ppm)=7.51 (s, 4H), 7.41 (d, J=8.2 Hz, 4H), 6.95 (d, J=8.2 Hz, 4H), 3.99 (s, 12H)), 3.83 (s, 2H)

Production Example 21: Synthesis of Blocking Agent Dissociation Catalyst (C12)

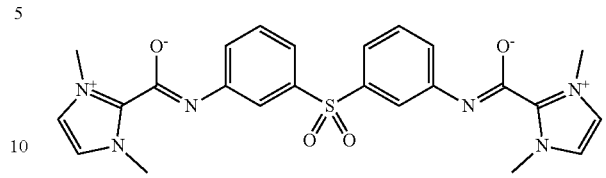

0.6 g (4.5 mmol) of 1,3-dimethylimidazolium-2-carboxylate obtained in Production Example 10, 1.0 g (2.2 mmol) of bis[3-(t-butoxycarbonylamino)phenyl]sulfone obtained in Production Example 6, and 18 mL of chlorobenzene were placed in a 30-mL test tube purged with nitrogen, followed by stirring at 130° C. for 6 hours. After the obtained reaction mixture was cooled to 25° C., filtration was performed, and the obtained brown solid was dried under reduced pressure, thereby obtaining 1.3 g of a blocking agent dissociation catalyst (C12) represented by the above formula (pure content: 1.1 g, yield: 99%). The $^1$H-NMR analysis results of the compound represented by the above Formula are shown below.

$^1$H-NMR (DMSO-d6) δ (ppm)=7.68 (s, 2H), 7.63 (d, J=7.3 Hz, 2H), 7.56 (s, 4H), 7.44-7.38 (m, 2H), 7.34-7.30 (m, 2H), 4.01 (s, 12H)

Production Example 22: Synthesis of Blocking Agent Dissociation Catalyst (C$_{12}$)

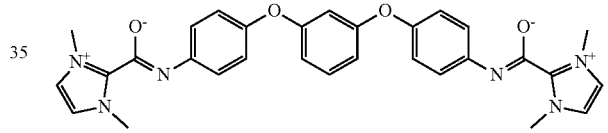

2.0 g (14 mmol) of 1,3-dimethylimidazolium-2-carboxylate obtained in Production Example 10, 3.5 g (7.1 mmol) of 1,3-bis[4-(t-butoxycarbonylamino)phenoxy]benzene obtained in Production Example 7, and 80 mL of chlorobenzene were placed in a three-necked flask purged with nitrogen, followed by stirring at 130° C. for 3 hours. The obtained reaction mixture was cooled to 25° C., and then dried under reduced pressure, thereby obtaining 3.80 g of a blocking agent dissociation catalyst (C$_{12}$) represented by the above formula (yield: 99%). The $^1$H-NMR analysis results of the compound represented by the above Formula are shown below.

$^1$H-NMR (CD$_3$OD) δ (ppm)=7.47 (s, 4H), 7.42 (d, J=9.0 Hz, 4H), 7.23 (t, J=8.2 Hz, 1H), 6.96 (d, J=9.0 Hz, 4H), 6.63 (dd, J=8.2, 2.4 Hz, 2H), 6.57 (t, J=2.4 Hz, 1H), 3.98 (s, 12H)

Production Example 23: Synthesis of Blocking Agent Dissociation Catalyst (C14)

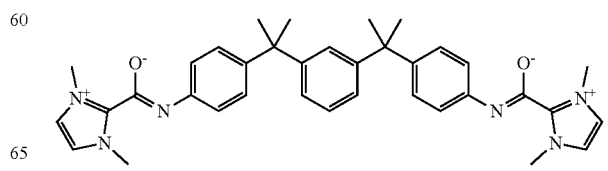

1.5 g (11.0 mmol) of 1,3-dimethylimidazolium-2-carboxylate obtained in Production Example 10, 3.0 g (5.5 mmol) of 1,3-bis {2-[4-(t-butoxycarbonylamino)phenyl]-2-propyl}benzene obtained in Production Example 8, and 100 mL of chlorobenzene were placed in a three-necked flask purged with nitrogen, followed by stirring at 130° C. for 3 hours. The obtained reaction mixture was cooled to 25° C., and then dried under reduced pressure. The obtained solid was washed three times with 100 ml of toluene, and then dried under reduced pressure, thereby obtaining 2.23 g of a blocking agent dissociation catalyst (C14) represented by the above formula (yield: 55%). The $^1$H-NMR analysis results of the compound represented by the above Formula are shown below.

was cooled to 25° C., and then dried under reduced pressure, thereby obtaining 4.65 g of a blocking agent dissociation catalyst (C15) represented by the above formula (pure content: 4.0 g, yield: 99%). The $^1$H-NMR analysis results of the compound represented by the above formula are shown below.

$^1$H-NMR (CD$_3$OD) δ (ppm)=7.51 (m, 2H), 7.45 (m, 2H), 7.35-7.34 (m, 4H), 7.13-7.11 (m, 4H) 4.35 (t, J=7.4 Hz, 4H), 3.95 (s, 6H), 3.90 (s, 2H), 1.88 (m, 4H), 1.34-1.26 (m, 20H), 0.87 (t, J=7.6 Hz, 6H)

Production Example 25: Synthesis of Blocking Agent Dissociation Catalyst (C16)

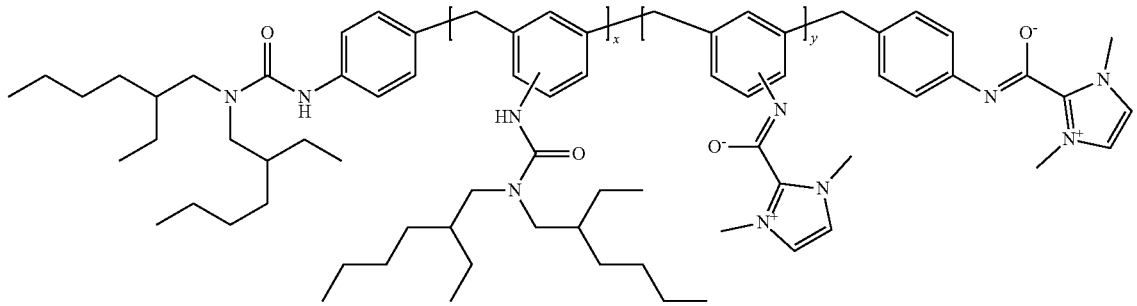

$^1$H-NMR (DMSO-d6) δ (ppm)=7.53 (s, 4H), 7.42-7.39 (m, 4H), 7.12 (s, 1H), 6.98-6.96 (m, 7H), 4.00 (s, 12H), 1.58 (s, 12H)

Production Example 24: Synthesis of Blocking Agent Dissociation Catalyst (C15)

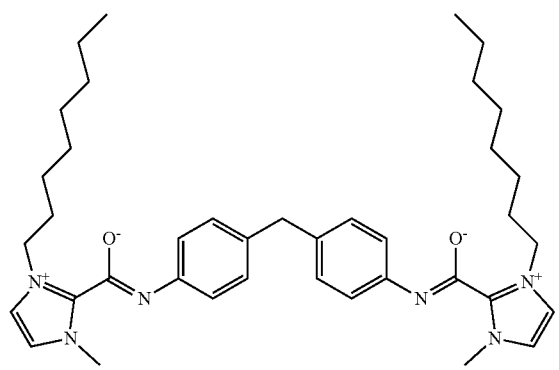 [SMILES: CCCCCCCC[n+]1ccn(C)c1/C([O-])=N/c1ccc(Cc2ccc(/N=C(\[O-])c3n(C)cc[n+]3CCCCCCCC)cc2)cc1]

4.9 g of a solution of 1-methyl-3-octylimidazolium-2-carboxylate obtained in Production Example 9 in methanol (pure content of 1-methyl-3-octylimidazolium-2-carboxylate: 3.7 g (16 mmol)), 2.5 g (6.3 mmol) of bis[4-(t-butoxycarbonylamino)phenyl]methane obtained in Production Example 5, and 100 mL of chlorobenzene were placed in a three-necked flask purged with nitrogen, followed by stirring at 130° C. for 5 hours. The obtained reaction mixture 52.9 g of Sumidur 44V20L (produced by Sumika Covestro Urethane Co., Ltd., polymethylene polyphenyl polyisocyanate, isocyanate content: 33%) (414.1 mmol as isocyanate groups) and 400 mL of toluene were placed in a 1-L four-necked flask purged with nitrogen. The mixture was ice-cooled (internal temperature: 6° C.), and while stirring, a solution of 50.0 g (207.1 mol) of di(2-ethylhexyl)amine and 100 mL of toluene was added thereto dropwise, followed by stirring at room temperature for 1 hour, thus allowing part of the isocyanate groups of polymethylene polyphenyl polyisocyanate to react with di(2-ethylhexyl)amine.

Figure 2:
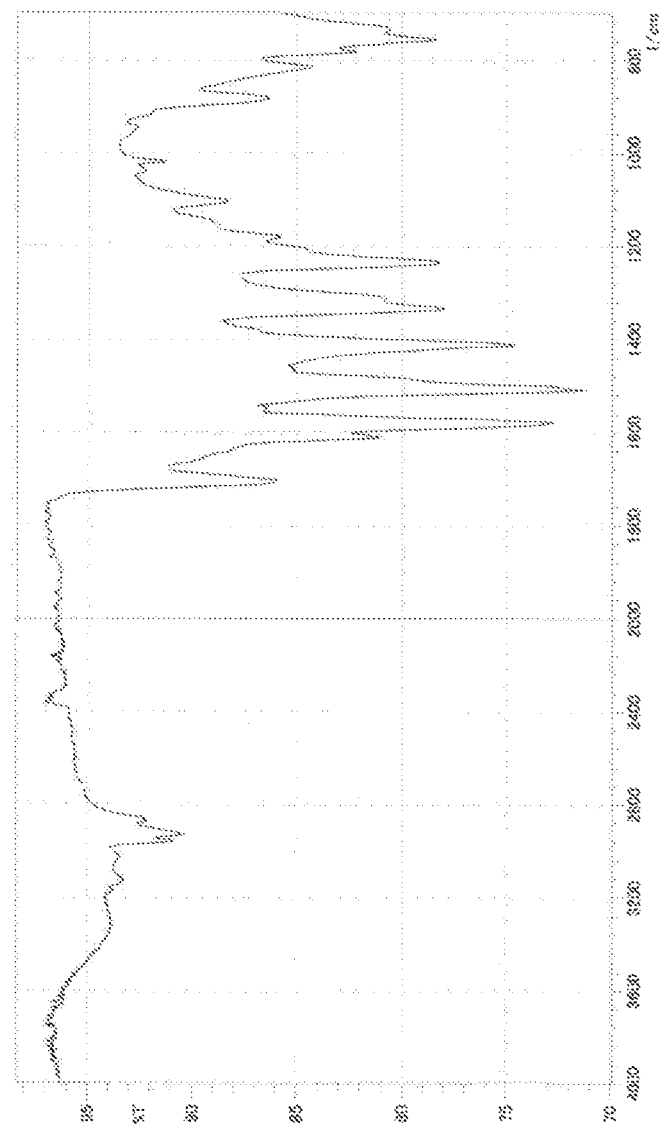
FIG. 2 is a graph showing the IR analysis results of the blocking agent dissociation catalyst (C16) of the Examples of the present application.

29.0 g (207.1 mmol) of 1,3-dimethylimidazolium-2-carboxylate obtained in Production Example 10 was added to the obtained reaction mixture, followed by stirring at 110° C. for 2 hours. The obtained liquid reaction mixture was dried under reduced pressure. The obtained concentrated residue was washed twice with 500 mL of water, and then dried under reduced pressure, thereby obtaining 93.9 g of a blocking agent dissociation catalyst (C16). The blocking agent dissociation catalyst (C16) is presumed to be a composition comprising a compound having the structure represented by the above formula. In the above formula, x and y each represent a repeating unit derived from polymethylene polyphenyl polyisocyanate, which is a raw material. FIG. 1 shows the $^1$H-NMR (DMSO-d$_6$) analysis results of the blocking agent dissociation catalyst (C16), and FIG. 2 shows the IR analysis results.

Production Example 26: Synthesis of Blocking Agent Dissociation Catalyst (C17)

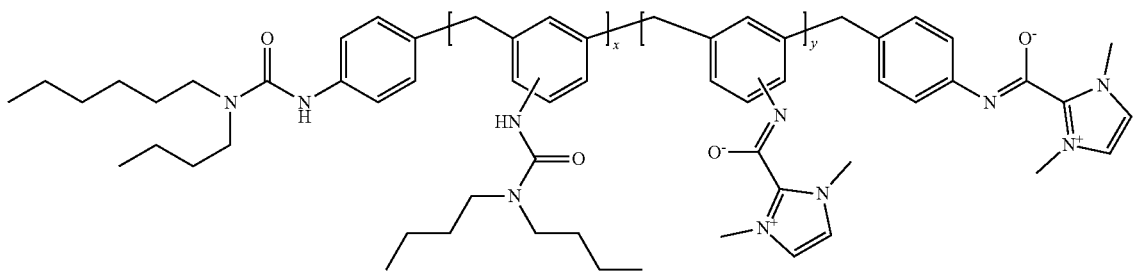

5.00 g of Sumidur 44V20L (produced by Sumika Covestro Urethane Co., Ltd., polymethylene polyphenyl polyisocyanate, isocyanate content: 33%) (39.2 mmol as isocyanate groups) and 40 mL of toluene were placed in a 200-mL three-necked flask purged with nitrogen. The mixture was ice-cooled, and while stirring, a solution of 2.53 g (19.4 mol) of dibutylamine and 10 mL of toluene was added thereto dropwise, followed by stirring at room temperature for 1 hour, thus allowing part of the isocyanate groups of polymethylene polyphenyl polyisocyanate to react with dibutylamine.

Figure 3:
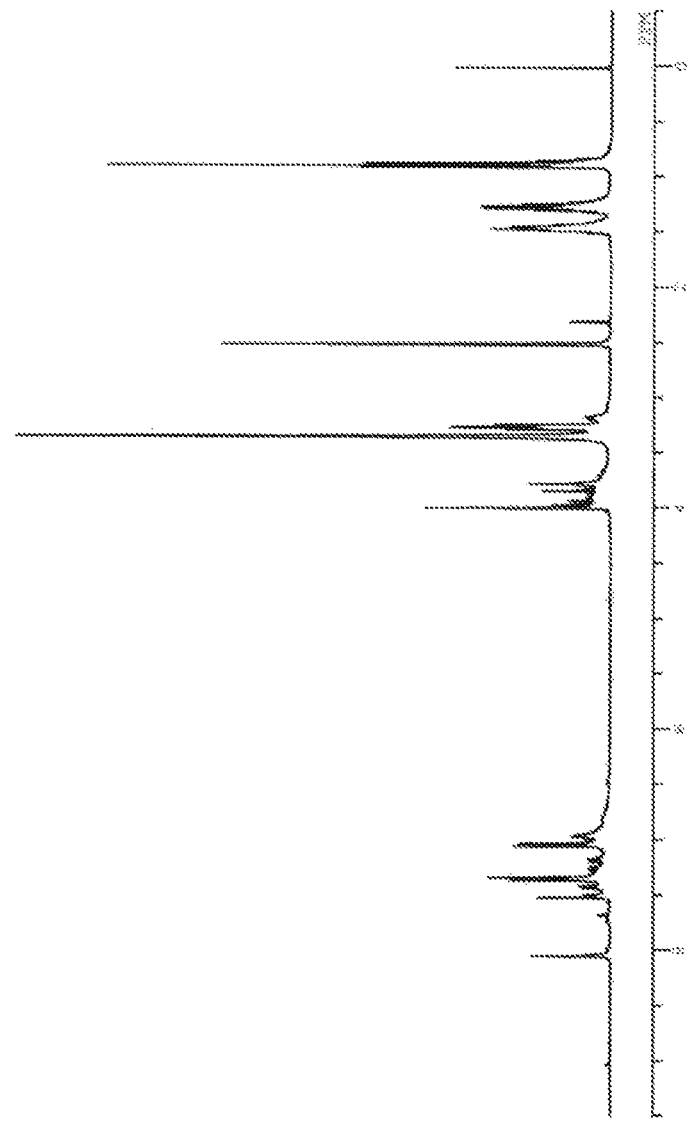
FIG. 3 is a graph showing the $^1$H-NMR analysis results of the blocking agent dissociation catalyst (C17) of the Examples of the present application.
Figure 4:
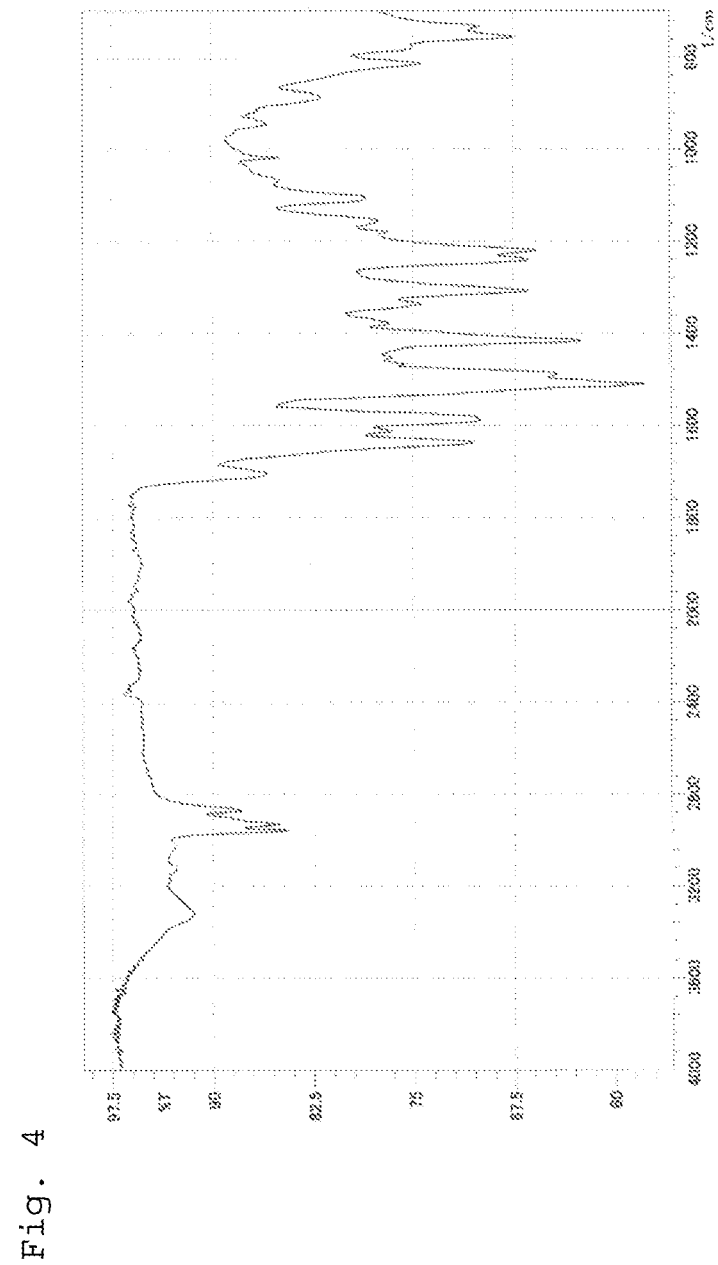
FIG. 4 is a graph showing the IR analysis results of the blocking agent dissociation catalyst (C17) of the Examples of the present application.

2.74 g (19.6 mmol) of 1,3-dimethylimidazolium-2-carboxylate obtained in Production Example 10 was added to the obtained reaction mixture, followed by stirring at 110° C. for 3 hours. The obtained liquid reaction mixture was dried under reduced pressure. The obtained concentrated residue was washed twice with 25 mL of water, and then dried under reduced pressure, thereby obtaining 4.54 g of a reaction product. The blocking agent dissociation catalyst (C17) is presumed to be a composition comprising a compound having the structure represented by the above formula. In the above formula, x and y each represent a repeating unit derived from polymethylene polyphenyl polyisocyanate, which is a raw material. FIG. 3 shows the $^1$H-NMR (DMSO-$d_6$) analysis results of the blocking agent dissociation catalyst (C17), and FIG. 4 shows the IR analysis results.

Production Example 27: Synthesis of Blocking Agent Dissociation Catalyst (C18)

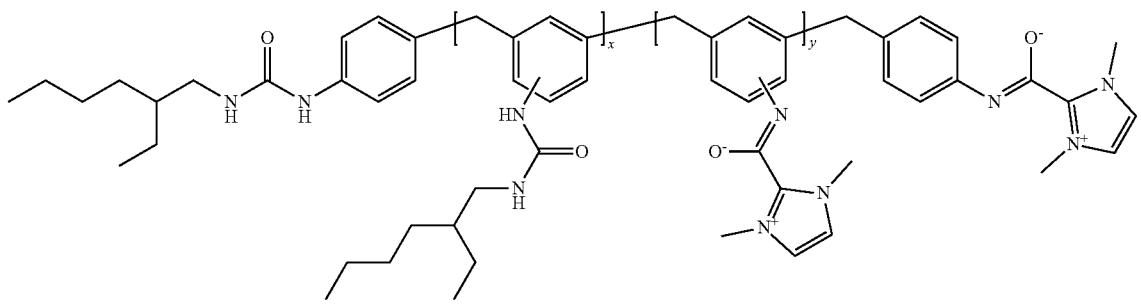

5.00 g of Sumidur 44V20L (produced by Sumika Covestro Urethane Co., Ltd., polymethylene polyphenyl polyisocyanate, isocyanate content: 33%) (39.2 mmol as isocyanate groups) and 40 mL of toluene were placed in a 200-mL three-necked flask purged with nitrogen. The mixture was ice-cooled, and while stirring, a solution of 2.53 g (19.4 mol) of 2-ethylhexylamine and 10 mL of toluene was added thereto dropwise, followed by stirring at room temperature for 1 hour, thus allowing part of the isocyanate groups of polymethylene polyphenyl polyisocyanate to react with 2-ethylhexylamine.

Figure 5:
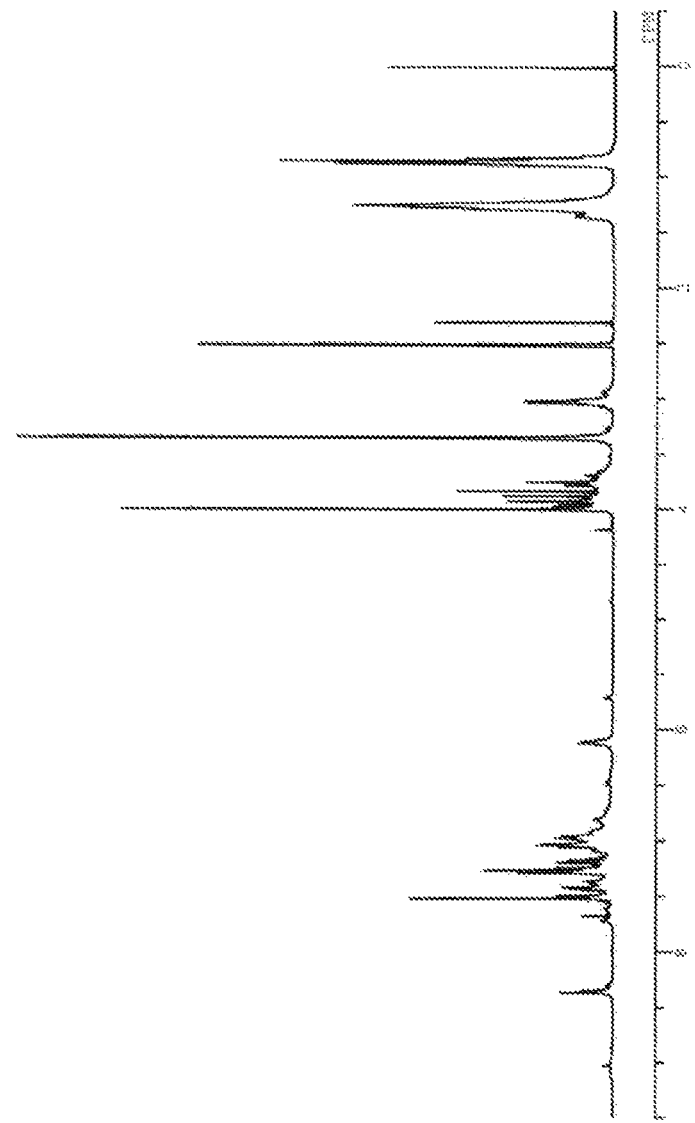
FIG. 5 is a graph showing the $^1$H-NMR analysis results of the blocking agent dissociation catalyst (C18) of the Examples of the present application.
Figure 6:
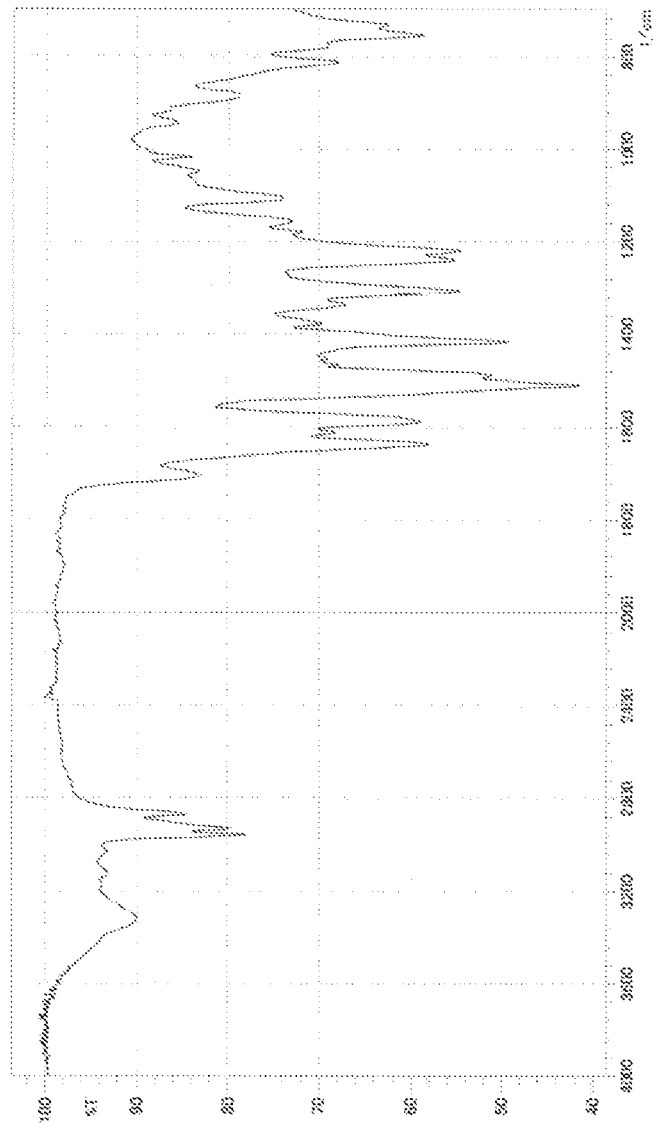
FIG. 6 is a graph showing the IR analysis results of the blocking agent dissociation catalyst (C18) of the Examples of the present application.

2.74 g (19.6 mmol) of 1,3-dimethylimidazolium-2-carboxylate obtained in Production Example 10 was added to the obtained reaction mixture, followed by stirring at 110° C. for 3 hours. The obtained liquid reaction mixture was dried under reduced pressure. The obtained concentrated residue was washed twice with 25 mL of water, and then dried under reduced pressure, thereby obtaining 6.03 g of a reaction product. The blocking agent dissociation catalyst (C18) is presumed to be a composition comprising a compound having the structure represented by the above formula. In the above formula, x and y each represent a repeating unit derived from polymethylene polyphenyl polyisocyanate, which is a raw material. FIG. 5 shows the $^1$H-NMR (DMSO-$d_6$) analysis results of the blocking agent dissociation catalyst (C18), and FIG. 6 shows the IR analysis results.

Production Example 28: Synthesis of Blocking Agent Dissociation Catalyst (C19)

(C19-1)

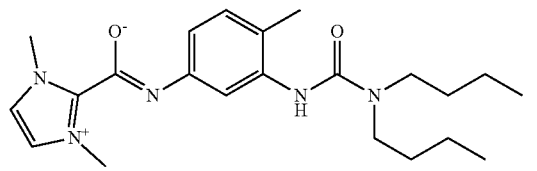

(C19-2)

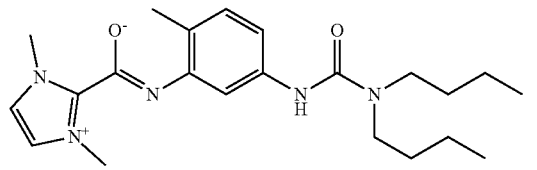

5.00 g (57.4 mmol) of tolylene-2,4-diisocyanate and 40 mL of toluene were placed in a 200-mL three-necked flask purged with nitrogen. The mixture was ice-cooled, and while stirring, a solution of 3.71 g (28.7 mol) of dibutylamine and 10 mL of toluene was added thereto dropwise, followed by stirring at room temperature for 1 hour, thus allowing part of the isocyanate groups of tolylene-2,4-diisocyanate to react with dibutylamine.

Figure 7:
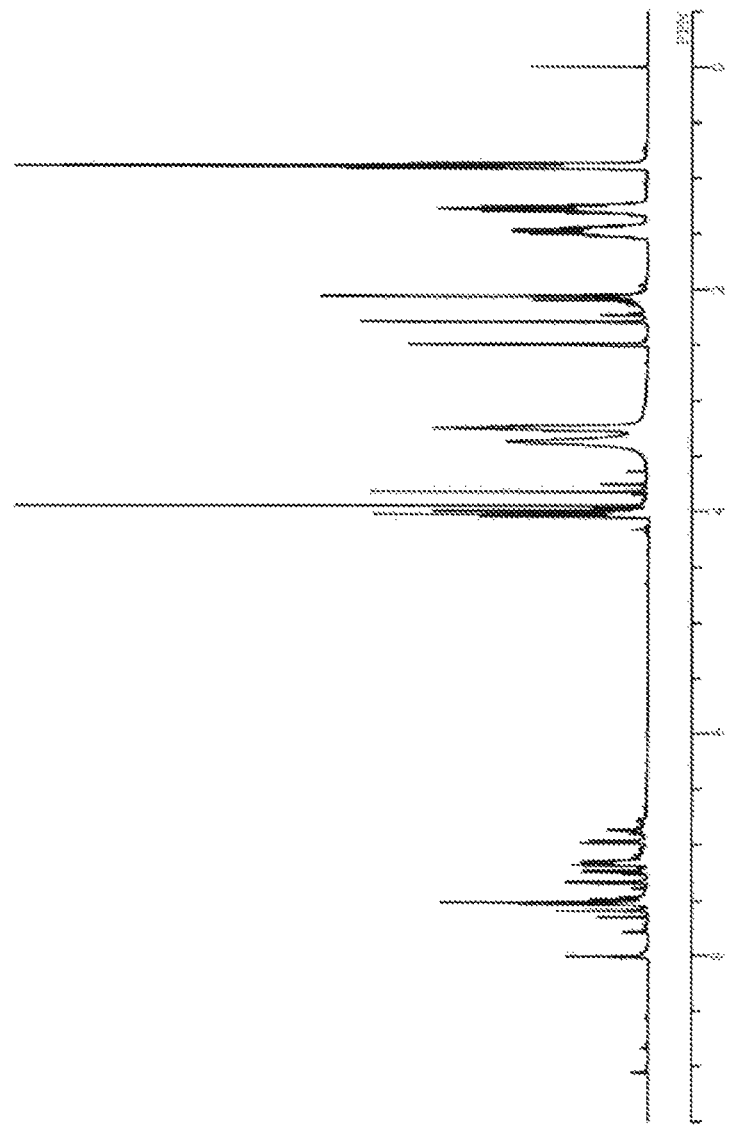
FIG. 7 is a graph showing the $^1$H-NMR analysis results of the blocking agent dissociation catalyst (C19) of the Examples of the present application.
Figure 8:
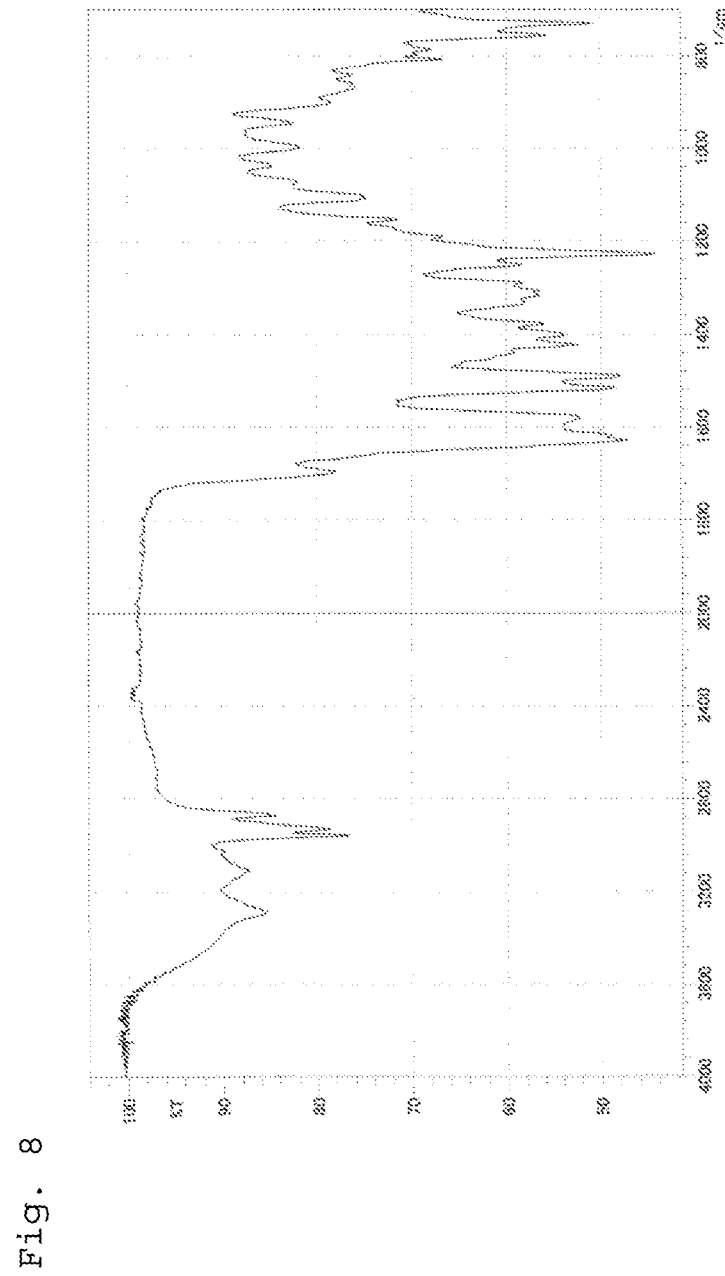
FIG. 8 is a graph showing the IR analysis results of the blocking agent dissociation catalyst (C19) of the Examples of the present application.

4.02 g (28.7 mmol) of 1,3-dimethylimidazolium-2-carboxylate obtained in Production Example 10 was added to the obtained reaction mixture, followed by stirring at 110° C. for 3 hours. The obtained liquid reaction mixture was dried under reduced pressure. The obtained concentrated residue was washed twice with 25 mL of water, and then dried under reduced pressure, thereby obtaining 5.43 g of a reaction product. The blocking agent dissociation catalyst (C19) is presumed to be a composition comprising a compound having the structure represented by Formula (C19-1) and/or (C19-2). FIG. 7 shows the $^1$H-NMR (DMSO-$d_6$) analysis results of the blocking agent dissociation catalyst (C19), and FIG. 8 shows the IR analysis results.

Production Example 29: Synthesis of Blocking Agent Dissociation Catalyst (C20)

(C20-1)

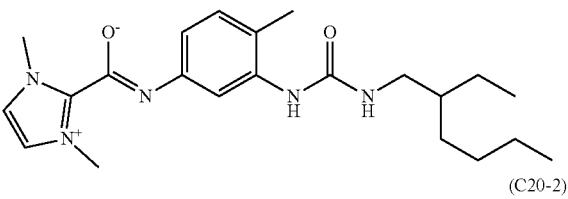

(C20-2)

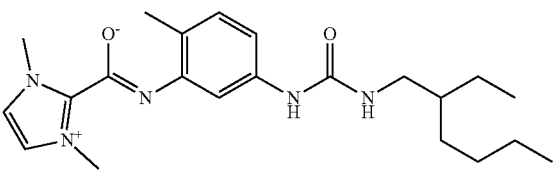

Figure 9:
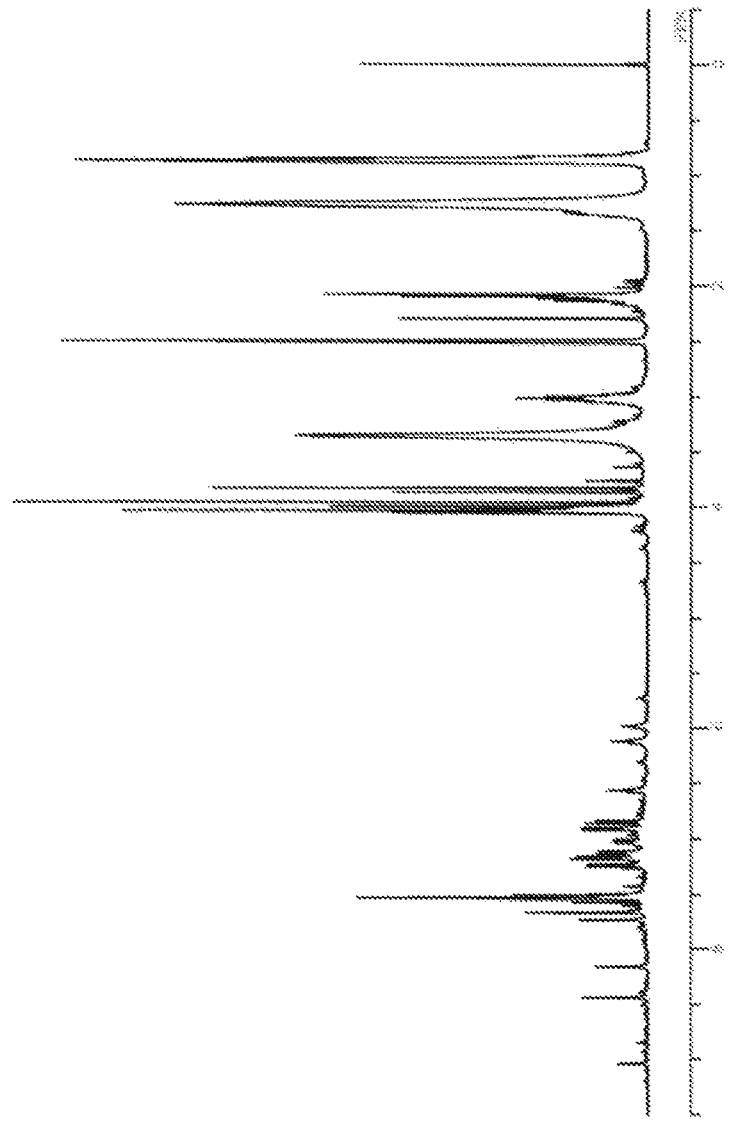
FIG. 9 is a graph showing the $^1$H-NMR analysis results of the blocking agent dissociation catalyst (C20) of the Examples of the present application.
Figure 10:
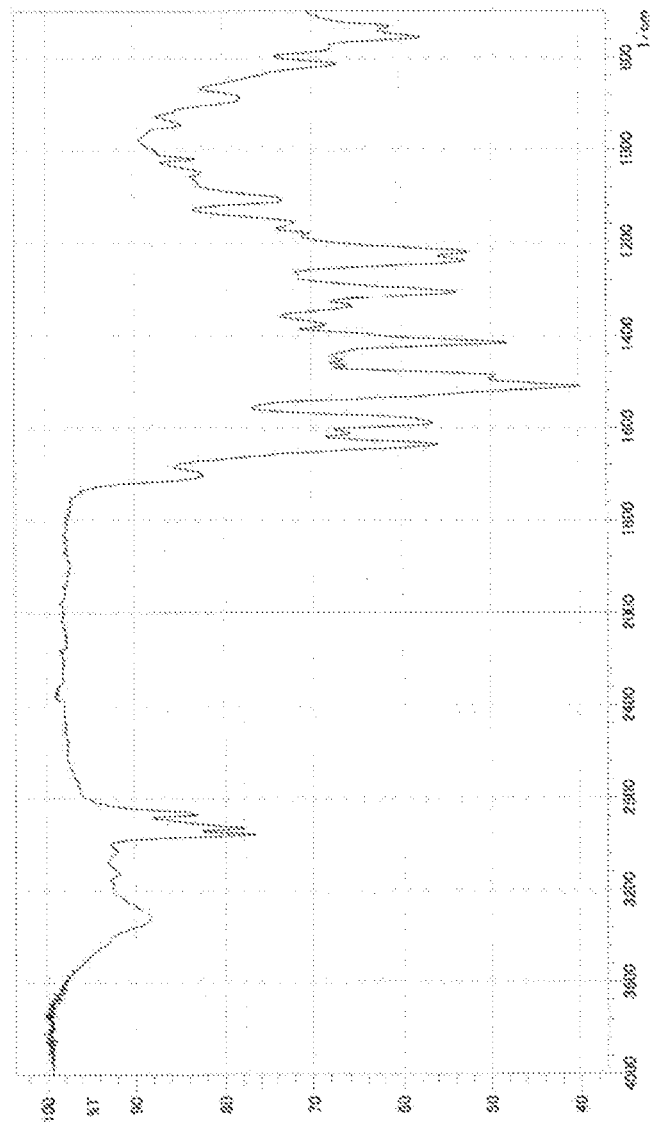
FIG. 10 is a graph showing the IR analysis results of the blocking agent dissociation catalyst (C20) of the Examples of the present application.

5.00 g (57.4 mmol) of tolylene-2,4-diisocyanate and 40 mL of toluene were placed in a 200-mL three-necked flask purged with nitrogen. The mixture was ice-cooled, and while stirring, a solution of 3.71 g (28.7 mol) of 2-ethylhexylamine and 10 mL of toluene was added thereto dropwise, followed by stirring at room temperature for 1 hour, thus allowing part of the isocyanate groups of tolylene-2,4-diisocyanate to react with 2-ethylhexylamine. 4.02 g (28.7 mmol) of 1,3-dimethylimidazolium-2-carboxylate obtained in Production Example 10 was added thereto, and the mixture was stirred at 110° C. for 3 hours. The obtained liquid reaction mixture was dried under reduced pressure. The obtained concentrated residue was washed twice with 25 mL of water, and then dried under reduced pressure, thereby obtaining 8.10 g of a reaction product. The blocking agent dissociation catalyst (C20) is presumed to be a composition comprising a compound having the structure represented by Formula (C20-1) and/or (C20-2). FIG. 9 shows the $^1$H-NMR (DMSO-$d_6$) analysis results of the blocking agent dissociation catalyst (C20), and FIG. 10 shows the IR analysis results.

Production Example 30: Synthesis of 3,5-dimethylpyrazole Blocked Diisocyanate (B1)

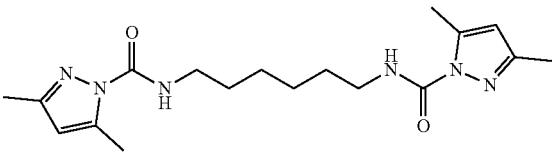

22.9 g (0.24 mol) of 3,5-dimethylpyrazole and 20.0 g of toluene were placed in a 200-mL three-necked flask purged with nitrogen. While stirring the mixture, a solution of 20.0 g (0.12 mol) of hexamethylene diisocyanate and 20.5 g of toluene was added thereto dropwise, followed by stirring at 40° C. for 2 hours. After the obtained reaction mixture was cooled to 25° C., filtration was performed, and the obtained white solid was dried under reduced pressure, thereby obtaining 26.7 g of 3,5-dimethylpyrazole blocked diisocyanate (B1) represented by the above formula (hereinafter abbreviated as "the DMP blocked diisocyanate") (yield: 62%). The $^1$H-NMR analysis results of the compound represented by the above formula are shown below.

$^1$H-NMR (CDCl$_3$) δ (ppm)=7.24 (br, 2H), 5.89 (s, 2H), 3.33 (q, J=6.8 Hz, 4H), 2.55 (s, 6H), 2.20 (s, 6H), 1.63-1.60 (m, 4H), 1.45-1.43 (m, 4H)

Production Example 31: Synthesis of Methyl Ethyl Ketoxime Blocked Diisocyanate (B2)

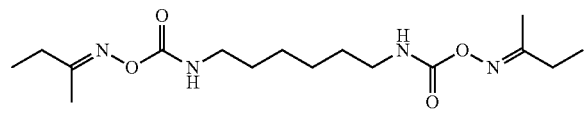 [SMILES: CC/C(C)=N/OC(=O)NCCCCCCNC(=O)O/N=C(\C)CC]

12.1 g (0.14 mol) of methyl ethyl ketoxime and 11.7 g of toluene were placed in a 200-mL three-necked flask purged with nitrogen. While stirring the mixture, a solution of 11.7 g (0.070 mol) of hexamethylene diisocyanate and 11.8 g of toluene was added thereto dropwise, followed by stirring at 50° C. for 2 hours. The obtained reaction mixture was dried under reduced pressure, thereby obtaining 20.9 g of methyl ethyl ketoxime blocked diisocyanate (B2) represented by the above formula (hereinafter abbreviated as "the MEKO blocked diisocyanate") (yield: 88%). The $^1$H-NMR analysis results of the compound represented by the above formula are shown below. The $^1$H-NMR analysis results revealed that this compound was a mixture of structural isomers.

$^1$H-NMR (CDCl$_3$) δ (ppm)=6.33 (br, 2H), 3.28 (q, J=6.8 Hz, 4H), 2.48 (q, J=7.7 Hz, 1.0H), 2.32 (q, J=7.5 Hz, 3.0H), 2.01 (s, 4.4H), 1.96 (s, 1.6H), 1.58 (m, 4H), 1.38 (m, 4H), 1.14 (t, J=7.6 Hz, 4.4H), 1.11 (t, J=7.6 Hz, 1.6H) (Z-form/E-form=74/26)

Production Example 32: Synthesis of ε-Caprolactam Blocked Diisocyanate (B3)

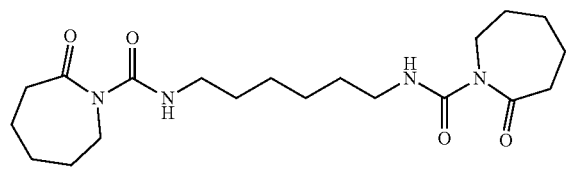 [SMILES: O=C1CCCCCN1C(=O)NCCCCCCNC(=O)N1CCCCCC1=O]

11.8 g (0.10 mol) of ε-caprolactam and 8.9 g of toluene were placed in a 200-mL three-necked flask purged with nitrogen. While stirring the mixture, a solution of 11.7 g (0.070 mol) of hexamethylene diisocyanate and 11.8 g of toluene was added thereto dropwise, followed by stirring at 80° C. for 17 hours. The obtained reaction mixture was dried under reduced pressure, thereby obtaining 20.4 g of ε-caprolactam blocked diisocyanate (B3) represented by the above formula (hereinafter abbreviated as "the E-CAP blocked diisocyanate") (yield: 74%). The $^1$H-NMR analysis results of the compound represented by the above formula are shown below.

$^1$H-NMR (CDCl$_3$) δ (ppm)=9.24 (br, 2H), 3.99-3.97 (m, 4H), 3.30-3.25 (m, 4H), 2.71-2.69 (m, 4H), 1.78-1.72 (m, 12H), 1.57-1.54 (m, 4H), 1.38-1.34 (m, 4H)

Production Example 33: Synthesis of ε-Caprolactam Blocked Polyisocyanate (B4)

11.3 g (0.10 mol) of ε-caprolactam and 40.5 g of toluene were placed in a 200-mL three-necked flask purged with nitrogen. While stirring the mixture, 20.1 g (0.10 mol as isocyanate groups) of TAKENATE D170N (polyisocyanate, isocyanate content: 21.0%, produced by Mitsui Chemicals, Inc.) was added thereto dropwise, followed by stirring at 80° C. for 5 hours. 0.25 g of the obtained reaction mixture was sampled and mixed with a solution of 0.12 g (0.93 mmol) of di-n-butylamine in 10 mL of toluene. A small amount of bromocresol green was added thereto, and the mixture was titrated with a 0.2 mol/L ethanolic hydrochloric acid solution. As a result, at an amount of 4.65 mL (0.93 mmol) of the ethanolic hydrochloric acid solution, the color of the solution turned from blue to yellow, which confirmed that there was no residual isocyanate groups. Thereafter, the remaining reaction mixture was dried under reduced pressure, thereby obtaining 32.8 g of ε-caprolactam blocked polyisocyanate (B4) (hereinafter abbreviated as "the E-CAP blocked polyisocyanate") (effective isocyanate: 13.5%, solids content: 95%). The effective isocyanate (%) and solids content (%) were calculated from the results of the $^1$H-NMR measurements by the following methods.

Effective Isocyanate (%):
16.4 mg of the obtained E-CAP blocked polyisocyanate (B4) and 11.8 mg of N,N-dimethyl-4-aminopyridine (purity 99.85 g, 94.8 μmol) as an internal standard sample were dissolved in deuterated chloroform, and the $^1$H-NMR was measured. Then, the effective isocyanate was calculated from the integration values of the 2H peak (δ=3.27 ppm) of the caprolactam moiety of E-CAP blocked polyisocyanate (B4) and the 6H peak (δ=3.00 ppm) of the methyl groups of N,N-dimethyl-4-aminopyridine.

Solids Content (%):
The residual ratio of toluene (%) in the E-CAP blocked polyisocyanate (B4) was obtained from the above $^1$H-NMR measurement results, and the solids content was calculated by the following equation:

Solids content (%)=100−residual toluene (%).

Catalyst Performance Evaluation

Example 1

According to the composition shown in Table 1, the DMP blocked diisocyanate (B1) obtained in Production Example 30, N-methylpyrrolidone (hereinafter abbreviated as "NMP"), the blocking agent dissociation catalyst (C10) obtained in Production Example 19, 3,3-iminobis(propylamine) (hereinafter abbreviated as "IBPA") were placed in a test tube, followed by stirring for 30 minutes, thereby preparing a thermosetting composition.

The mixing ratio of the thermosetting composition was calculated by the following equation:

Amount of IBPA (g)=the amount of blocked isocyanate (g)/the molecular weight of blocked isocyanate (g/mol)×2×the molecular weight of IBPA (g/mol)/3/1.05

Amount of blocking agent dissociation catalyst (g)=the amount of blocked isocyanate (g)×0.05

Amount of NMP (g)=the amount of blocked isocyanate (g)×2.00

0.6 mL of the thermosetting composition immediately after the preparation was collected and added to the hot plate of the automatic curing time measuring device, and heating was performed at a rate of 10° C./min while stirring. At this time, the curing temperature was measured taking a temperature at which the stirring torque exceeded 2% as the curing temperature. Table 1 shows the results.

The fluidity of the thermosetting composition after storage at 30° C. for one week under a nitrogen atmosphere was visually observed, and the storage stability was evaluated. Table 1 shows the results.

0.6 mL of the thermosetting composition after storage at 30° C. for one week under a nitrogen atmosphere was collected and added to the hot plate of the automatic curing time measuring device, and heating was performed at a rate of 10° C./min while stirring. At this time, the curing temperature was measured taking a temperature at which the stirring torque exceeded 2% as the curing temperature. Table 1 shows the results.

Examples 2 to 20

Thermosetting compositions were obtained in the same manner as in Example 1, except that the blocking agent dissociation catalyst (C10) was changed to the blocking agent dissociation catalysts shown in Table 1. Table 1 shows the compositions.

The measurement of the curing temperature immediately after the preparation was performed in the same manner as in Example 1. Table 1 shows the results.

Comparative Example 1

A thermosetting composition was obtained in the same manner as in Example 1, except that the thermosetting composition was prepared without adding the blocking agent dissociation catalyst (C10). Table 1 shows the composition.

The measurement of the curing temperature immediately after the preparation and the evaluation of the storage stability were performed in the same manner as in Example 1. Table 1 shows the results.

Comparative Example 2

A thermosetting composition was obtained in the same manner as in Example 1, except that the blocking agent dissociation catalyst (C10) was changed to dibutyltin dilaurate (hereinafter abbreviated as "DBTL"). Table 1 shows the composition.

The measurement of the curing temperature immediately after the preparation, the evaluation of storage stability, and the measurement of the curing temperature after storage for one week were performed in the same manner as in Example 1. Table 1 shows the results.

Comparative Example 3

A thermosetting composition was obtained in the same manner as in Example 1, except that the blocking agent dissociation catalyst (C10) was changed to 1,5,7-triazabicyclo[4.4.0]dec-5-ene (hereinafter abbreviated as "TBD"). Table 1 shows the compositions.

The measurement of the curing temperature immediately after the preparation and the evaluation of the storage stability were performed in the same manner as in Example 1. Table 1 shows the results.

TABLE 1

| | Thermosetting composition | | | | | Curing temperature[5] | | Fluidity[6] |
|---|---|---|---|---|---|---|---|---|
| | B1[1] | IBPA[2] | NMP[3] | Catalyst[4] | | Immediately after preparation | After one week | After one week |
| Ex. 1 | 1.00 g | 0.23 g | 2.00 g | C10 | 0.05 g | 100° C. | 106° C. | ○ |
| Ex. 2 | 1.00 g | 0.23 g | 2.00 g | C1 | 0.05 g | 123° C. | — | — |
| Ex. 3 | 1.00 g | 0.23 g | 2.00 g | C2 | 0.05 g | 122° C. | — | — |
| Ex. 4 | 1.00 g | 0.23 g | 2.00 g | C3 | 0.05 g | 103° C. | — | — |
| Ex. 5 | 1.00 g | 0.23 g | 2.00 g | C4 | 0.05 g | 112° C. | — | — |
| Ex. 6 | 1.00 g | 0.23 g | 2.00 g | C5 | 0.05 g | 114° C. | — | — |
| Ex. 7 | 1.00 g | 0.23 g | 2.00 g | C6 | 0.05 g | 111° C. | — | — |
| Ex. 8 | 1.00 g | 0.23 g | 2.00 g | C7 | 0.05 g | 98° C. | — | — |
| Ex. 9 | 1.00 g | 0.23 g | 2.00 g | C8 | 0.05 g | 95° C. | — | — |
| Ex. 10 | 1.00 g | 0.23 g | 2.00 g | C9 | 0.05 g | 99° C. | — | — |
| Ex. 11 | 1.00 g | 0.23 g | 2.00 g | C11 | 0.05 g | 102° C. | — | — |
| Ex. 12 | 1.00 g | 0.23 g | 2.00 g | C12 | 0.05 g | 123° C. | — | — |
| Ex. 13 | 1.00 g | 0.23 g | 2.00 g | C13 | 0.05 g | 104° C. | — | — |
| Ex. 14 | 1.00 g | 0.23 g | 2.00 g | C14 | 0.05 g | 105° C. | — | — |
| Ex. 15 | 1.00 g | 0.23 g | 2.00 g | C15 | 0.05 g | 107° C. | — | — |
| Ex. 16 | 1.00 g | 0.23 g | 2.00 g | C16 | 0.05 g | 107° C. | — | — |
| Ex. 17 | 1.00 g | 0.23 g | 2.00 g | C17 | 0.05 g | 114° C. | — | — |
| Ex. 18 | 1.00 g | 0.23 g | 2.00 g | C18 | 0.05 g | 109° C. | — | — |
| Ex. 19 | 1.00 g | 0.23 g | 2.00 g | C19 | 0.05 g | 112° C. | — | — |
| Ex. 20 | 1.00 g | 0.23 g | 2.00 g | C20 | 0.05 g | 107° C. | — | — |
| Comp. Ex. 1 | 1.00 g | 0.23 g | 2.00 g | None | 0 g | 128° C. | — | ○ |
| Comp. Ex. 2 | 1.00 g | 0.23 g | 2.00 g | DBTL[7] | 0.05 g | 128° C. | 127° C. | ○ |
| Comp. Ex. 3 | 1.00 g | 0.23 g | 2.00 g | TBD[8] | 0.05 g | 112° C. | x | x |

[1]B1 denotes the DMP blocked diisocyanate obtained in Production Example 30.
[2]Iminobispropylamine produced by Tokyo Chemical Industry Co., Ltd.
[3]N-Methylpyrrolidone produced by Junsei Chemical Co., Ltd.
[4]C1 to C20 denote the blocking agent dissociation catalysts obtained in Production Examples 10 to 29.
[5]The numerical figures represent curing temperatures, "x" indicates that the evaluation could not be performed with curing being completed, and "—" indicates that the evaluation was not performed.
[6]○ indicates the presence of fluidity, "x" indicates the absence of fluidity with curing being completed, and "—" indicates that the evaluation was not performed.
[7]Dibutyltin dilaurate produced by Tokyo Chemical Industry Co., Ltd.
[8]1,5,7-Triazabicyclo[4.4.0]dec-5-ene produced by Tokyo Chemical Industry Co., Ltd.

In Table 1, IBPA, which is an amine compound, is used as an isocyanate reactive group-containing compound. The reaction of isocyanates and amines usually proceeds quickly without a catalyst; thus, when the blocking agent of blocked isocyanate dissociates, the regenerated isocyanate groups are expected to react with IBPA quickly to achieve curing. Therefore, the curing temperature shown in Table 1 is considered to be synonymous with the dissociation temperature of the blocking agent.

The results shown in Table 1 revealed that the thermosetting compositions comprising the blocking agent dissociation catalysts (C1 to 20) of the present invention were cured at lower temperatures, compared to the thermosetting composition comprising DBTL, which is a known blocking agent dissociation catalyst. These results revealed that the blocking agent dissociation catalysts of the present invention achieve excellent curability at low temperatures with respect to blocked isocyanate and IBPA, i.e., excellent low-temperature dissociation of the blocking agent. The results also revealed that the thermosetting composition obtained by using the blocking agent dissociation catalyst (C10) of the present invention exhibited excellent storage stability more than that of the thermosetting composition obtained by using TBD, which is a known blocking agent dissociation catalyst.

Example 21

A thermosetting composition was obtained in the same manner as in Example 2, except that the DMP blocked diisocyanate (B1) was changed to the MEKO blocked diisocyanate (B2) obtained in Production Example 31. Table 2 shows the composition.

0.6 mL of the thermosetting composition immediately after the preparation was collected and added to the hot plate of the automatic curing time measuring device, and heating was performed at a rate of 10° C./min while stirring. At this time, the curing temperature was measured taking a temperature at which the stirring torque exceeded 2% as the curing temperature. Table 2 shows the results.

The fluidity of the thermosetting composition after storage at 30° C. for one month under a nitrogen atmosphere was visually observed, and the storage stability was evaluated. Table 2 shows the results.

0.6 mL of the thermosetting composition after storage at 30° C. for one month under a nitrogen atmosphere was collected and added to the hot plate of the automatic curing time measuring device, and heating was performed at a rate of 10° C./min while stirring. At this time, the curing temperature was measured taking a temperature at which the stirring torque exceeded 2% as the curing temperature. Table 2 shows the results.

Examples 22 to 25 and Comparative Examples 5 and 6

Thermosetting compositions were obtained in the same manner as in Example 21, except that the blocking agent dissociation catalyst (C1) was changed to the blocking agent dissociation catalysts shown in Table 2. Table 2 shows the compositions.

The measurement of the curing temperature immediately after the preparation, the evaluation of storage stability, and the measurement of the curing temperature after storage for one month were performed in the same manner as in Example 21. Table 2 shows the results. In the evaluation of storage stability, the curing temperature after storage for one month was not measured when the thermosetting composition was cured after one month.

Comparative Example 4

A thermosetting composition was obtained in the same manner as in Example 21, except that the thermosetting composition was prepared without adding the blocking agent dissociation catalyst (C1). Table 2 shows the composition.

The measurement of the curing temperature immediately after the preparation, the evaluation of storage stability, and the measurement of the curing temperature after storage for one month were performed in the same manner as in Example 21. Table 2 shows the results.

TABLE 2

| | Thermosetting composition | | | | Curing temperature[5] | | Fluidity[6] |
|---|---|---|---|---|---|---|---|
| | B2[1] | IBPA[2] | NMP[3] | Catalyst[4] | Immediately after preparation | After one month | After one month |
| Ex. 21 | 1.00 g | 0.24 g | 2.00 g | C1      0.05 g | 129° C. | 149° C. | o |
| Ex. 22 | 1.00 g | 0.24 g | 2.00 g | C3      0.05 g | 109° C. | 135° C. | o |
| Ex. 23 | 1.00 g | 0.24 g | 2.00 g | C10     0.05 g | 110° C. | 148° C. | o |
| Ex. 24 | 1.00 g | 0.24 g | 2.00 g | C11     0.05 g | 110° C. | 138° C. | o |
| Ex. 25 | 1.00 g | 0.24 g | 2.00 g | C15     0.05 g | 114° C. | 155° C. | o |
| Comp. Ex. 4 | 1.00 g | 0.24 g | 2.00 g | None    0 g | 178° C. | 173° C. | o |
| Comp. Ex. 5 | 1.00 g | 0.24 g | 2.00 g | DBTL[7] 0.05 g | 178° C. | 176° C. | o |
| Comp. Ex. 6 | 1.00 g | 0.24 g | 2.00 g | TBD[8]  0.05 g | 118° C. | x | x |

[1]B2 denotes the MEKO blocked diisocyanate obtained in Production Example 31.
[2]Iminobispropylamine produced by Tokyo Chemical Industry Co., Ltd.
[3]N-Methylpyrrolidone produced by Junsei Chemical Co., Ltd.
[4]C1, C3, C10, C11, and C15 denote the blocking agent dissociation catalysts obtained in Production Examples 10, 12, 19, 20, and 24.
[5]The numerical figures represent curing temperatures, and "x" indicates that the evaluation could not be performed with curing being completed.
[6]o indicates the presence of fluidity, and "x" indicates the absence of fluidity with curing being completed.
[7]Dibutyltin dilaurate produced by Tokyo Chemical Industry Co., Ltd.
[8]1,5,7-Triazabicyclo[4.4.0]dec-5-ene produced by Tokyo Chemical Industry Co, Ltd.

Example 26

A thermosetting composition was obtained in the same manner as in Example 2, except that the DMP blocked diisocyanate (B1) was changed to the E-CAP blocked diisocyanate (B3) obtained in Production Example 32. Table 3 shows the composition.

The measurement of the curing temperature immediately after the preparation, the evaluation of storage stability, and the measurement of the curing temperature after storage for one month were performed in the same manner as in Example 21. Table 3 shows the results.

Examples 27 to 30 and Comparative Examples 8 and 9

Thermosetting compositions were obtained in the same manner as in Example 26, except that the blocking agent dissociation catalyst (C1) was changed to the blocking agent dissociation catalysts shown in Table 3. Table 3 shows the composition.

The measurement of the curing temperature immediately after the preparation, the evaluation of storage stability, and the measurement of the curing temperature after storage for one month were performed in the same manner as in Example 21. Table 3 shows the results. In the evaluation of storage stability, the curing temperature after storage for one month was not measured when the thermosetting composition was cured after one month.

Comparative Example 7

A thermosetting composition was obtained in the same manner as in Example 26, except that the thermosetting composition was prepared without adding the blocking agent dissociation catalyst (C1). Table 3 shows the composition.

The measurement of the curing temperature immediately after the preparation, the evaluation of storage stability, and the measurement of the curing temperature after storage for one month were performed in the same manner as in Example 21. Table 3 shows the results.

TABLE 3

| | Thermosetting composition | | | | | Curing temperature[5] | | Fluidity[6] |
|---|---|---|---|---|---|---|---|---|
| | B3[1] | IBPA[2] | NMP[3] | Catalyst[4] | | Immediately after preparation | After one month | After one month |
| Ex. 26 | 1.00 g | 0.21 g | 2.00 g | C1 | 0.05 g | 154° C. | 158° C. | ○ |
| Ex. 27 | 1.00 g | 0.21 g | 2.00 g | C3 | 0.05 g | 130° C. | 180° C. | ○ |
| Ex. 28 | 1.00 g | 0.21 g | 2.00 g | C10 | 0.05 g | 158° C. | 185° C. | ○ |
| Ex. 29 | 1.00 g | 0.21 g | 2.00 g | C11 | 0.05 g | 144° C. | 181° C. | ○ |
| Ex. 30 | 1.00 g | 0.21 g | 2.00 g | C15 | 0.05 g | 168° C. | 177° C. | ○ |
| Comp. Ex. 7 | 1.00 g | 0.21 g | 2.00 g | None | 0 g | 245° C. | 210° C. | ○ |
| Comp. Ex. 8 | 1.00 g | 0.21 g | 2.00 g | DBTL[7] | 0.05 g | 225° C. | 210° C. | ○ |
| Comp. Ex. 9 | 1.00 g | 0.21 g | 2.00 g | TBD[8] | 0.05 g | 167° C. | x | x |

[1] B3 denotes the E-CAP blocked diisocyanate obtained in Production Example 32.
[2] Iminobispropylamine produced by Tokyo Chemical Industry Co., Ltd.
[3] N-Methylpyrrolidone produced by Junsei Chemical Co., Ltd.
[4] C1, C3, C10, C11, and C15 denote the blocking agent dissociation catalysts obtained in Production Examples 10, 12, 19, 20, and 24.
[5] The numerical figures represent curing temperatures, and "x" indicates that the evaluation could not be performed with curing being completed.
[6] ○ indicates the presence of fluidity, and "x" indicates the absence of fluidity with curing being completed.
[7] Dibutyltin dilaurate produced by Tokyo Chemical Industry Co., Ltd.
[8] 1,5,7-Triazabicyclo[4.4.0]dec-5-ene produced by Tokyo Chemical Industry Co, Ltd.

The results shown in Tables 1, 2, and 3 revealed that the blocking agent dissociation catalysts of the present invention achieved excellent low-temperature dissociation for the blocked isocyanate in which the isocyanate groups are blocked by 3,5-dimethylpyrazole, methyl ethyl ketoxime, or ε-caprolactam. The results also revealed that the thermosetting compositions comprising the blocking agent dissociation catalysts of the present invention exhibit excellent storage stability.

Example 31

According to the composition shown in Table 4, TRIXENE BI7982 (Baxenden Chemicals Ltd., 3,5-dimethylpyrazole blocked polyisocyanate (hereinafter abbreviated as "the DMP blocked polyisocyanate"), effective isocyanate: 10.2%, solids content: 70%), NMP, the blocking agent dissociation catalyst (C1) obtained in Production Example 10, and SANNIX HD-402 (produced by Sanyo Chemical Industries, Ltd., polyoxyalkylene polyol, hydroxyl value: 392) were added so that the effective isocyanate group/alcohol group=1.05, followed by stirring for 30 minutes, thereby obtaining a thermosetting composition.

The mixing ratio of the thermosetting composition was calculated by the following equation.

Amount of SANNIX HD-402 (mol)={the amount of blocked isocyanate (g)×effective isocyanate (%)/100/42 (g/mol)}/1.05

Amount of SANNIX HD-402 (g)=the amount of SANNIX HD-402 (mol)/{hydroxyl value (mg KOH/g)/56.1 (g/mol)/1000}

Amount of blocking agent dissociation catalyst (g)=blocked isocyanate solids content (g)×0.05

Amount of NMP (g)=blocked isocyanate solids content (g)×2.00−{the amount of blocked isocyanate (g)−blocked isocyanate solids content (g)}

The measurement of the curing temperature immediately after preparation, the evaluation of storage stability, and the measurement of the curing temperature after storage for one month were performed in the same manner as in Example 21. Table 4 shows the results.

Examples 32 to 35 and Comparative Example 11

Thermosetting compositions were obtained in the same manner as in Example 31, except that the blocking agent dissociation catalyst (C1) was changed to the blocking agent dissociation catalysts shown in Table 4. Table 4 shows the compositions.

The measurement of the curing temperature immediately after the preparation, the evaluation of storage stability, and the measurement of the curing temperature after storage for one month were performed in the same manner as in Example 21. Table 4 shows the results.

Comparative Example 10

A thermosetting composition was obtained in the same manner as in Example 31, except that the thermosetting composition was prepared without adding the blocking agent dissociation catalyst (C1). Table 4 shows the composition.

The measurement of the curing temperature immediately after the preparation, the evaluation of storage stability, and the measurement of the curing temperature after storage for one month were performed in the same manner as in Example 21. Table 4 shows the results.

TABLE 4

| | Thermosetting composition | | | | Curing temperature[5] | | Fluidity[6] |
|---|---|---|---|---|---|---|---|
| | TRIXENE BI 7989[1] | SANNIX HD-402[2] | NMP[3] | Catalyst[4] | Immediately after preparation | After one month | After one month |
| Ex. 31 | 1.43 g | 0.47 g | 1.57 g | C1    0.05 g | 132° C. | 122° C. | ○ |
| Ex. 32 | 1.43 g | 0.47 g | 1.57 g | C3    0.05 g | 143° C. | 128° C. | ○ |
| Ex. 33 | 1.43 g | 0.47 g | 1.57 g | C10   0.05 g | 150° C. | 130° C. | ○ |
| Ex. 34 | 1.43 g | 0.47 g | 1.57 g | C11   0.05 g | 140° C. | 126° C. | ○ |
| Ex. 35 | 1.43 g | 0.47 g | 1.57 g | C15   0.05 g | 139° C. | 130° C. | ○ |
| Comp. Ex 10 | 1.43 g | 0.47 g | 1.57 g | None    0 g | 220° C. | 244° C. | ○ |
| Comp. Ex. 11 | 1.43 g | 0.47 g | 1.57 g | DBTL[7] 0.05 g | 167° C. | 167° C. | ○ |

[1]DMP blocked polyisocyanate produced by Baxenden Chemicals Ltd.

[2]Polyoxyalkylene polyol produced by Sanyo Chemical Industries, Ltd.

[3]N-Methylpyrrolidone produced by Junsei Chemical Co, Ltd.

[4]C1, C3, C10, C11, and C15 denote the blocking agent dissociation catalysts obtained in Production Examples 10, 12, 19, 20, and 24.

[5]The numerical figures represent curing temperatures, "x" indicates that the evaluation could not be performed with curing being completed, and "—" indicates that the evaluation was not performed.

[6]○ indicates the presence of fluidity, "x" indicates the absence of fluidity with curing being completed, and "—" indicates that the evaluation was not performed.

[7]Dibutyltin dilaurate produced by Tokyo Chemical Industry Co., Ltd.

Example 36

A thermosetting composition was obtained in the same manner as in Example 31, except that the blocked isocyanate was changed to Duranate TPA-B80E (produced by Asahi Kasei Corporation, methyl ethyl ketoxime blocked polyisocyanate (hereinafter abbreviated as "the MEKO blocked polyisocyanate"), effective isocyanate: 12.4%, solids content: 81%). Table 5 shows the composition.

The measurement of the curing temperature immediately after the preparation, the evaluation of storage stability, and the measurement of the curing temperature after storage for one month were performed in the same manner as in Example 21. Table 5 shows the results.

Examples 37 to 40 and Comparative Example 13

Thermosetting compositions were obtained in the same manner as in Example 36, except that the blocking agent dissociation catalyst (C1) was changed to the blocking agent dissociation catalysts shown in Table 5. Table 5 shows the compositions.

The measurement of the curing temperature immediately after the preparation, the evaluation of storage stability, and the measurement of the curing temperature after storage for one month were performed in the same manner as in Example 21. Table 5 shows the results.

Comparative Example 12

A thermosetting composition was obtained in the same manner as in Example 36, except that the thermosetting composition was prepared without adding the blocking agent dissociation catalyst (C1). Table 5 shows the composition.

The measurement of the curing temperature immediately after the preparation, the evaluation of storage stability, and the measurement of the curing temperature after storage for one month were performed in the same manner as in Example 21. Table 5 shows the results.

TABLE 5

|  | Thermosetting composition | | | | | Curing temperature[5] | | Fluidity[6] |
| --- | --- | --- | --- | --- | --- | --- | --- | --- |
|  | Duranate TPA-B80E[1] | SANNIX HD-402[2] | NMP[3] | Catalyst[4] | | Immediately after preparation | After one month | After one month |
| Ex. 36 | 1.24 g | 0.50 g | 1.76 g | C1 | 0.05 g | 149° C. | 148° C. | o |
| Ex. 37 | 1.24 g | 0.50 g | 1.76 g | C3 | 0.05 g | 157° C. | 157° C. | o |
| Ex. 38 | 1.24 g | 0.50 g | 1.76 g | C10 | 0.05 g | 162° C. | 162° C. | o |
| Ex. 39 | 1.24 g | 0.50 g | 1.76 g | C11 | 0.05 g | 160° C. | 158° C. | o |
| Ex. 40 | 1.24 g | 0.50 g | 1.76 g | C15 | 0.05 g | 166° C. | 164° C. | o |
| Comp. Ex. 12 | 1.24 g | 0.50 g | 1.76 g | None | 0 g | 237° C. | 236° C. | o |
| Comp. Ex. 13 | 1.24 g | 0.50 g | 1.76 g | DBTL[7] | 0.05 g | 177° C. | 177° C. | o |

[1]MEKO blocked polyisocyanate produced by Asahi Kasei Corporation

[2]Polyoxyalkylene polyol produced by Sanyo Chemical Industries, Ltd.

[3]N-Methylpyrrolidone produced by Junsei Chemical Co., Ltd.

[4]C1, C3, C10, C11, and C15 denote the blocking agent dissociation catalysts obtained in Production Examples 10, 12, 19, 20, and 24.

[5]The numerical figures represent curing temperatures, "x" indicates that the evaluation could not be performed with curing being completed, and "—" indicates that the evaluation was not performed.

[6]o indicates the presence of fluidity, "x" indicates the absence of fluidity with curing being completed, and "—" indicates that the evaluation was not performed.

[7]Dibutyltin dilaurate produced by Tokyo Chemical Industry Co., Ltd.

Example 41

A thermosetting composition was obtained in the same manner as in Example 31, except that blocked isocyanate was changed to the E-CAP blocked polyisocyanate (B4) obtained in Production Example 33. Table 6 shows the composition.

The measurement of the curing temperature immediately after the preparation, the evaluation of storage stability, and the measurement of the curing temperature after storage for one month were performed in the same manner as in Example 21. Table 6 shows the results.

Examples 42 to 45 and Comparative Example 15

Thermosetting compositions were obtained in the same manner as in Example 41, except that the blocking agent dissociation catalyst (C1) was changed to the blocking agent dissociation catalysts shown in Table 6. Table 6 shows the compositions.

The measurement of the curing temperature immediately after the preparation, the evaluation of storage stability, and the measurement of the curing temperature after storage for one month were performed in the same manner as in Example 21. Table 6 shows the results.

Comparative Example 14

A thermosetting composition was obtained in the same manner as in Example 41, except that the thermosetting composition was prepared without adding the blocking agent dissociation catalyst (C1). Table 6 shows the composition.

The measurement of the curing temperature immediately after the preparation, the evaluation of storage stability, and the measurement of the curing temperature after storage for one month were performed in the same manner as in Example 21. Table 6 shows the results.

TABLE 6

| | Thermosetting composition | | | | | Curing temperature[5] | | Fluidity[6] |
|---|---|---|---|---|---|---|---|---|
| | B4[1] | SANNIX HD-402[2] | NMP[3] | Catalyst[4] | | Immediately after preparation | After one month | After one month |
| Ex. 41 | 1.05 g | 0.46 g | 1.95 g | C1 | 0.05 g | 179° C. | 180° C. | ○ |
| Ex. 42 | 1.05 g | 0.46 g | 1.95 g | C3 | 0.05 g | 180° C. | 184° C. | ○ |
| Ex. 43 | 1.05 g | 0.46 g | 1.95 g | C10 | 0.05 g | 189° C. | 188° C. | ○ |
| Ex. 44 | 1.05 g | 0.46 g | 1.95 g | C11 | 0.05 g | 181° C. | 186° C. | ○ |
| Ex. 45 | 1.05 g | 0.46 g | 1.95 g | C15 | 0.05 g | 187° C. | 191° C. | ○ |
| Comp. Ex. 14 | 1.05 g | 0.46 g | 1.95 g | None | 0 g | 230° C. | 230° C. | ○ |
| Comp. Ex. 15 | 1.05 g | 0.46 g | 1.95 g | DBTL[7] | 0.05 g | 205° C. | 208° C. | ○ |

[1] B4 denotes the E-CAP blocked polyisocyanate obtained in Production Example 33.
[2] Polyoxyalkylene polyol produced by Sanyo Chemical Industries, Ltd.
[3] N-Methylpyrrolidone produced by Junsei Chemical Co., Ltd.
[4] C1, C3, C10, C11, and C15 denote the blocking agent dissociation catalysts obtained in Production Examples 10, 12, 19, 20, and 24.
[5] The numerical figures represent curing temperatures, "x" indicates that the evaluation could not be performed with curing being completed, and "—" indicates that the evaluation was not performed.
[6] ○ indicates the presence of fluidity, "x" indicates the absence of fluidity with curing being completed, and "—" indicates that the evaluation was not performed.
[7] Dibutyltin dilaurate produced by Tokyo Chemical Industry Co., Ltd.

The results shown in Tables 4 to 6 revealed that the blocking agent dissociation catalysts of the present invention also exhibited low-temperature curability and excellent storage stability in the thermosetting compositions obtained by using alcohol as the isocyanate reactive group-containing compound.

The invention claimed is:

1. A blocking agent dissociation catalyst for blocked isocyanates comprising a nitrogen-containing compound represented by Formula (1b):

Formula (1b)

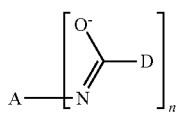

(1b)

wherein A represents a substituted or unsubstituted hydrocarbon group, n is an integer of 1 or more, and D is a nitrogen-containing organic group represented by Formula (2):

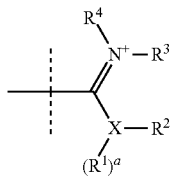

(2)

wherein $R^1$, $R^2$, $R^3$, and $R^4$ are the same or different, and each represents a hydrocarbon group that optionally contains a heteroatom; some or all of $R^1$, $R^2$, $R^3$, and $R^4$ are optionally bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom.

2. The blocking agent dissociation catalyst for blocked isocyanates according to claim 1, wherein A is an unsubstituted hydrocarbon group, or a hydrocarbon group having at least one substituent selected from a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group.

3. The blocking agent dissociation catalyst for blocked isocyanates according to claim 1, wherein n is an integer of 1 to 6.

4. The blocking agent dissociation catalyst for blocked isocyanates according to claim 1, wherein the nitrogen-containing compound represented by Formula (1b) is a nitrogen-containing compound represented by the following Formula (1b-1), (1b-2), or (1b-3):

Formula (1b-1)

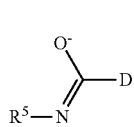

(1b-1)

wherein $R^5$ represents a substituted or unsubstituted hydrocarbon group, and D is as defined above;

Formula (1b-2)

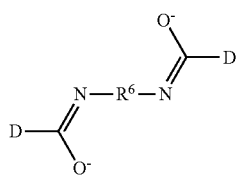

(1b-2)

wherein $R^6$ represents a substituted or unsubstituted hydrocarbon group, and D is as defined above: or Formula (1b-3)

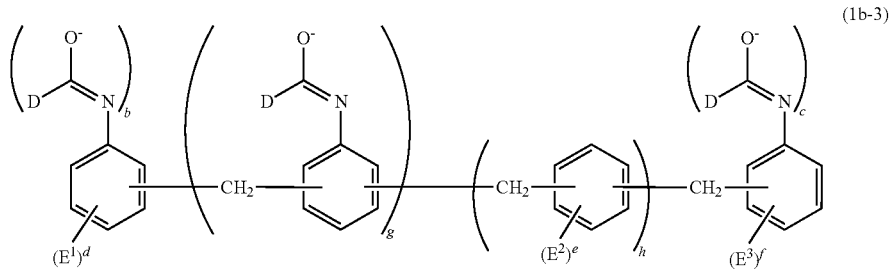

(1b-3)

wherein $E^1$, $E^2$, and $E^3$ each independently represent a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; g and h each independently represent an integer of 0 to 4, b and c are 0 or 1, and d, e, and f each independently represent an integer of 0 to 4, provided that at least one of b and c is 1 when g is 0; and D is as defined above.

5. An amidate compound represented by the following Formula (1b-3):

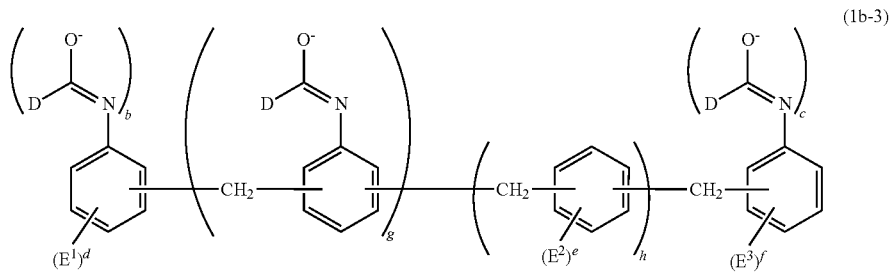

wherein $E^1$, $E^2$, and $E^3$ each independently represent a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; g and h each independently represent an integer of 0 to 4, b and c are 0 or 1, d and f each independently represent an integer of 0 to 4, and e is an integer of 1 to 4, provided that at least one of b and c is 1 when g is 0, and at least one of d and f is 1 when h is 0; and D is as defined above a nitrogen-containing organic group represented by Formula (2):

wherein $R^1$, $R^2$, $R^3$, and $R^4$ are the same or different, and each represents a hydrocarbon group that optionally contains a heteroatom; some or all of $R^1$, $R^2$, $R^3$, and $R^4$ are optionally bonded together to form a ring structure; X represents a nitrogen atom, an oxygen atom, or a sulfur atom; and a represents 0 or 1, wherein a is 1 when X represents a nitrogen atom, and a is 0 when X represents an oxygen atom or a sulfur atom.

* * * * *